United States Patent
Eisenbach-Schwartz et al.

(10) Patent No.: US 9,982,048 B2
(45) Date of Patent: *May 29, 2018

(54) REDUCING SYSTEMIC REGULATORY T CELL LEVELS OR ACTIVITY FOR TREATMENT OF ALZHEIMER'S DISEASE

(71) Applicant: Yeda Research and Development Co. Ltd., Rehovot (IL)

(72) Inventors: Michal Eisenbach-Schwartz, Rehovot (IL); Kuti Baruch, Rehovot (IL); Neta Rosenzweig, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/821,595

(22) Filed: Nov. 22, 2017

(65) Prior Publication Data

US 2018/0111997 A1 Apr. 26, 2018

Related U.S. Application Data

(63) Continuation of application No. 14/797,894, filed on Jul. 13, 2015, now Pat. No. 9,856,318, which is a continuation-in-part of application No. PCT/IL2015/050265, filed on Mar. 12, 2015.

(60) Provisional application No. 61/951,783, filed on Mar. 12, 2014, provisional application No. 62/030,164, filed on Jul. 29, 2014.

(51) Int. Cl.
| | |
|---|---|
| *C07K 16/28* | (2006.01) |
| *A61K 39/395* | (2006.01) |
| *A61K 38/16* | (2006.01) |
| *A61K 31/7068* | (2006.01) |
| *A61K 45/06* | (2006.01) |
| *A61K 38/18* | (2006.01) |
| *A61K 38/14* | (2006.01) |
| *A61K 38/00* | (2006.01) |
| *A61K 38/20* | (2006.01) |
| *A61K 33/36* | (2006.01) |
| *A61K 31/404* | (2006.01) |
| *A61K 31/4155* | (2006.01) |
| *A61K 39/00* | (2006.01) |

(52) U.S. Cl.
CPC ........ *C07K 16/2803* (2013.01); *A61K 31/404* (2013.01); *A61K 31/4155* (2013.01); *A61K 31/7068* (2013.01); *A61K 33/36* (2013.01); *A61K 38/00* (2013.01); *A61K 38/005* (2013.01); *A61K 38/14* (2013.01); *A61K 38/168* (2013.01); *A61K 38/18* (2013.01); *A61K 38/208* (2013.01); *A61K 39/395* (2013.01); *A61K 39/39541* (2013.01); *A61K 45/06* (2013.01); *C07K 16/2818* (2013.01); *C07K 16/2827* (2013.01); *A61K 2039/505* (2013.01); *A61K 2039/507* (2013.01); *A61K 2039/545* (2013.01); *A61K 2039/572* (2013.01); *A61K 2121/00* (2013.01); *C07K 2317/21* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,563,869 B2 | 7/2009 | Honjo et al. |
| 8,008,449 B2 | 8/2011 | Korman et al. |
| 8,552,154 B2 | 10/2013 | Freeman et al. |
| 8,629,098 B2 | 1/2014 | Fahmy et al. |
| 8,709,416 B2 | 4/2014 | Langermann et al. |
| 8,735,553 B1 | 5/2014 | Li et al. |
| 8,779,105 B2 | 7/2014 | Korman et al. |
| 8,900,587 B2 | 12/2014 | Carven et al. |
| 8,927,697 B2 | 1/2015 | Davis et al. |
| 8,945,561 B2 | 2/2015 | Davis et al. |
| 8,952,136 B2 | 2/2015 | Carven et al. |
| 8,993,731 B2 | 3/2015 | Tyson et al. |
| 9,085,625 B2 | 7/2015 | Labrijn et al. |
| 9,394,365 B1 | 7/2016 | Eisenbach-Schwartz et al. |
| 9,512,225 B2 | 12/2016 | Eisenbach-Schwartz et al. |
| 9,512,227 B2 | 12/2016 | Eisenbach-Schwartz et al. |
| 9,534,052 B2 | 1/2017 | Eisenbach-Schwartz et al. |

(Continued)

FOREIGN PATENT DOCUMENTS

| | | |
|---|---|---|
| EP | 1575484 B1 | 5/2003 |
| EP | 2320940 B1 | 11/2009 |

(Continued)

OTHER PUBLICATIONS

Jin, et al., Role of PD-1 in Regulating T-Cell Immunity, Curr. Top. Microbiol. Immunol. 350: 17-37 (2011).
ADAPT-FS Research Group, Follow-Up Evaluation of Cognitive Function in the Randomized Alzheimer's Disease Anti-inflammatory Prevention Trial and its Follow-Up Study, Alzheimer's & Dementia 11: 216-225 (2015).
ADAPT-FS Research Group, Naproxen and Celecoxib do not Prevent AD in Early Results from Randomized Controlled Trial, Neural. 68: 1800-1808 (2007).

(Continued)

*Primary Examiner* — Ilia I Ouspenski
(74) *Attorney, Agent, or Firm* — Ultimatedge Law Group, P.C.; Dean G. Stathakis

(57) ABSTRACT

A pharmaceutical composition comprising an active agent that causes reduction of the level of systemic immunosuppression in an individual for use in treating a disease, disorder, condition or injury of the CNS that does not include the autoimmune neuroinflammatory disease, relapsing-remitting multiple sclerosis (RRMS), is provided. The pharmaceutical composition is for administration by a dosage regimen comprising at least two courses of therapy, each course of therapy comprising in sequence a treatment session followed by an interval session.

26 Claims, 20 Drawing Sheets

(56) References Cited

U.S. PATENT DOCUMENTS

| | | |
|---|---|---|
| 9,856,318 B2 | 1/2018 | Eisenbach-Schwartz et al. |
| 2010/0061992 A1 | 3/2010 | Anderson et al. |
| 2014/0004081 A1 | 1/2014 | Cobbold et al. |
| 2014/0023614 A1 | 1/2014 | Barawkar et al. |
| 2014/0044738 A1 | 2/2014 | Langermann et al. |
| 2014/0093511 A1 | 4/2014 | Lonberg et al. |
| 2014/0099254 A1 | 4/2014 | Chang et al. |
| 2014/0127227 A1 | 5/2014 | Chang et al. |
| 2014/0212446 A1 | 7/2014 | Riley et al. |
| 2014/0220021 A1 | 8/2014 | Shibayama et al. |
| 2014/0227180 A1 | 8/2014 | Govindan et al. |
| 2014/0234296 A1 | 8/2014 | Sharma et al. |
| 2014/0234331 A1 | 8/2014 | Korman et al. |
| 2014/0271540 A1 | 9/2014 | Stogniew et al. |
| 2014/0271677 A1 | 9/2014 | Palese et al. |
| 2014/0294759 A1 | 10/2014 | Chu et al. |
| 2014/0294765 A1 | 10/2014 | Cojocaru et al. |
| 2014/0294852 A1 | 10/2014 | Korman et al. |
| 2014/0302070 A1 | 10/2014 | Chen et al. |
| 2014/0314714 A1 | 10/2014 | Honjo et al. |
| 2014/0328833 A1 | 11/2014 | Korman et al. |
| 2014/0335048 A1 | 11/2014 | Stogniew et al. |
| 2014/0335093 A1 | 11/2014 | Olive |
| 2014/0341920 A1 | 11/2014 | Noelle |
| 2014/0348743 A1 | 11/2014 | Korman et al. |
| 2014/0348786 A1 | 11/2014 | Berzofsky et al. |
| 2014/0356363 A1 | 12/2014 | Zhou et al. |
| 2014/0377250 A1 | 12/2014 | Bantia |
| 2014/0377253 A1 | 12/2014 | Harding et al. |
| 2014/0377334 A1 | 12/2014 | Irvine et al. |
| 2015/0004175 A1 | 1/2015 | Kaech et al. |
| 2015/0017194 A1 | 1/2015 | Akahata et al. |
| 2015/0018516 A1 | 1/2015 | Govindan et al. |
| 2015/0079109 A1 | 3/2015 | Li et al. |
| 2015/0086584 A1 | 3/2015 | Gilboa et al. |
| 2015/0118222 A1 | 4/2015 | Levy et al. |
| 2015/0118234 A1 | 4/2015 | Honjo et al. |
| 2015/0132290 A1 | 5/2015 | Fuchs et al. |
| 2015/0152180 A1 | 6/2015 | Davis et al. |
| 2015/0165021 A1 | 6/2015 | Mashal et al. |
| 2015/0166661 A1 | 6/2015 | Chen et al. |
| 2015/0183875 A1 | 7/2015 | Cobbold et al. |
| 2015/0203560 A1 | 7/2015 | Grewal et al. |
| 2015/0203579 A1 | 7/2015 | Papadopoulos et al. |
| 2015/0210769 A1 | 7/2015 | Freeman et al. |
| 2015/0216970 A1 | 8/2015 | Grogan et al. |
| 2015/0218274 A1 | 8/2015 | Sabatos-Peyton et al. |
| 2016/0000909 A1 | 1/2016 | Eisenbach-Schwartz et al. |
| 2016/0008463 A1 | 1/2016 | Eisenbach-Schwartz et al. |
| 2017/0029508 A1 | 2/2017 | Eisenbach-Schwartz et al. |
| 2017/0240634 A1 | 8/2017 | Eisenbach-Schwartz et al. |
| 2018/0009893 A1* | 1/2018 | Eisenbach-Schwartz ... C07K 16/2827 |

FOREIGN PATENT DOCUMENTS

| | | |
|---|---|---|
| WO | 2014045305 A1 | 3/2014 |
| WO | 2014059251 A1 | 4/2014 |
| WO | 2014066527 A2 | 5/2014 |
| WO | 2014071402 A1 | 5/2014 |
| WO | 2014074852 A1 | 5/2014 |
| WO | 2014127917 A1 | 8/2014 |
| WO | 2014134355 A1 | 9/2014 |
| WO | 2014144791 A2 | 9/2014 |
| WO | 2014144885 A2 | 9/2014 |
| WO | 2014179664 A2 | 11/2014 |
| WO | 2014183066 A2 | 11/2014 |
| WO | 2014186035 A1 | 11/2014 |
| WO | 2014206107 A1 | 12/2014 |
| WO | 2014209804 A1 | 12/2014 |
| WO | 2015009856 A2 | 1/2015 |
| WO | 2015018528 A1 | 2/2015 |
| WO | 2015024042 A1 | 2/2015 |
| WO | 2015024060 A1 | 2/2015 |
| WO | 2015026684 A1 | 2/2015 |
| WO | 2015036394 A1 | 3/2015 |
| WO | 2015058573 A1 | 4/2015 |
| WO | 2015063187 A1 | 5/2015 |
| WO | 2015082499 A2 | 6/2015 |
| WO | 2015084721 A1 | 6/2015 |
| WO | 2015085210 A1 | 6/2015 |
| WO | 2015085847 A1 | 6/2015 |
| WO | 2015095895 A1 | 6/2015 |
| WO | 2015103072 A1 | 7/2015 |
| WO | 2015103602 A1 | 7/2015 |
| WO | 2015117002 A1 | 8/2015 |
| WO | 2015136541 A1 | 9/2015 |
| WO | 2017009829 A1 | 1/2017 |
| WO | 2017042633 A1 | 3/2017 |

OTHER PUBLICATIONS

Aisen, et al., Effects of Rofecoxib or Naproxen vs Placebo on Alzheimer Disease Progression, A Randomized Controlled Trial, JAMA 289(21): 2819-2826 (2003).

Anderson, et al., Lag-3, Tim-3, and TIGIT: Co-Inhibitory Receptors with Specialized Functions in Immune Regulation, Immun. Rev. 44: 989-1004 (2016).

Angelov, et al., Therapeutic Vaccine for Acute and Chronic Motor Neuron Diseases: Implications for Amyotrophic Lateral Sclerosis, PNAS 100(8): 4790-4795 (2013).

Arvanitakis, et al., Relation of NSAIDs to Incident AD, Change in Cognitive Function, and AD Pathology, Neurol. 70: 2219-2225 (2008).

Avidan, et al., Vaccination with Autoantigen Protects Against Aggregated [beta]-Amyloid and Glutamate Toxicity by Controlling Microglia: Effect of CD4 +CD25 + T cells, Eur. J. Immunol. 34(12): 3434-3445 (2004).

Bai, et al., All-trans Retinoic Acid Down-Regulates Inflammatory Responses by Shifting the Treg/Th17 Profile in Human Ulcerative and Murine Colitis, J. Leukoc. Biol. 86: 959-969 (2009).

Baruch, et al., Therapeutic potential of PD-1 immune checkpoint blockade in Alzheimer's disease, manuscript, Dept. of Neurobiology, Weizmann Institute of Science, 1-12.

Baruch, et al., CNS-Specific T Cells Shape Brain Function via the Choroid Plexus, Brain Behav. Immun. 34: 11-16 (2013).

Baruch, et al., CNS-Specific Immunity at the Choroid Plexus Shifts toward Destructive Th2 Inflammation in Brain Aging, PNAS 110(6): 2264-2269 (2013).

Baruch, et al., Aging-Induced Type 1 Interferon Response at the Choroid Plexus Negatively Affects Brain Function, Science 346(1): 89-93 (2014).

Baruch, et al., Cerebral Nitric Oxide Represses Choroid Plexus NFkB-Dependent Gateway Activity for Leukocyte Trafficking, EMBO J. 34(13): 1816-1828 (2015).

Baruch, et al., Breaking Immune Tolerance by Targeting Foxp3+ Regulatory T Cells Mitigates Alzheimer's Disease Pathology, Nat. Commun. 6(7967): 1-12 (2015).

Baruch, et al., PD-1 Immune Checkpoint Bblockade Reduces Pathology and Improves Memory in Mouse Models of Alzheimer's Disease, Nat. Med. 22(2): 135-139 (2016).

Bodhankar, et al., PD-L 1 Enhances CNS Inflammation and Infarct Volume Following Experimental Stroke in Mice in Opposition to PD-1 , J. Neuroinflam. 10(1): 1-15 (2013).

Bodhankar, et al., Targeting Immune Co-Stimulatory Effects of PD-L1 and PD-L2 Might Represent an Effective Therapeutic Strategy in Stroke, Frontiers Cell. Neurosci. 8(228): 1-14 (2014).

Bowers, et al., Virtual Ligand Screening of the p300/CBP Histone Acetyltransferase: Identification of a Selective Small Molecule Inhibitor, Chem. Biol. 17: 471-482 (2010).

Brestoff, et al., Commensal Bacteria at the Interface of Host Metabolism and the Immune System, Nat. Immunol. 14(7): 676-684 (2013).

Butovsky, et al., Glatiramer Acetate Fights Against Alzheimer's Disease by Inducing Dendritic-Like Microglia Expressing Insulin-Like Growth Factor 1, PNAS 103(31): 11784-11789 (2006).

(56) References Cited

OTHER PUBLICATIONS

Butovsky, et al., Selective Ablation of Bone Marrow-Derived Dendritic Cells Increases Amyloid Plaques in a Mouse Alzheimer's Disease Model, Eur. J. Neurosci. 26(2): 413-416 (2007).
Colombo, et al., Regulatory-T-cell Inhibition Versus Depletion: The Right Choice in Cancer Immunotherapy, Nat. Rev. Cancer 7: 880-887 (2007).
Coyne, et al., Adding Fuel to the Fire: Immunogenic Intensification, Hum. Vacc. Immunother. 10: 3306-3312 (2014).
Dalotto-Moreno, et al., Targeting Galectin-1 Overcomes Breast Cancer-Associated Immunosuppression and Prevents Metastatic Disease, Cancer Res. 73(3): 1107-1117 (2013).
Duraiswamy, et al., Dual Blockade of PD-1 and CTLA-4 Combined with Tumor Vaccine Effectively Restores T-cell Rejection Function in Tumors—Response, Cancer Res. 74(2): 633-634 (2014).
Francisco, et al., The PD-1 Pathway in Tolerance and Autoimmunity, Immunol. Rev. 236: 219-242 (2010).
Galvin, et al., Blocking Retinoic Acid Receptor-alpha Enhances the Efficacy of a Dendritic Cell Vaccine Against Tumours by Suppressing the Induction of Regulatory T Cells, Cancer Immunol. Immunother. 62: 1273-1282 (2013).
Ghiringhelli, et al., Production of Adenosine by Ectonucleotidases: A Key Factor in Tumor Immunoescape, J. Biomed. Biotech. 2012(473712): 1-9 (2012).
Guo, et al., Alzheimer's Disease and Retinal Neurodegeneration, Cur. Alzheimer Res. 7: 1-12 (2010).
He, et al., The Role of Regulatory T Cells in Neurodegenerative Diseases, WIREs Syst. Biol. Med. 5: 153-180 (2013).
Heylmann, et al., Human CD4+CD25+ Regulatory T Cells are Sensitive to Low Dose Cyclophosphamide: Implications for the Immune Response, PLoS ONE, 8(12): e83384, pp. 1-10 (2013).
Hirayama, et al., Overcoming Regulatory T-cell Suppression by a Lyophilized Preparation of *Streptococcus* Pyogenes, Eur. J. Immunol. 43: 989-1000 (2013).
Joller, et al., Immune Checkpoints in Central Nervous System Autoimmunity, Immunol. Rev. 248: 122-139 (2012).
Kawamoto, et al., Expression and Function of Inducible Co-Stimulator in Patients with Systemic Lupus Erythematosus: Possible Involvement in Excessive Interferon-γ and Anti-Double-Stranded DNA Antibody Production, Arthritis Res. Ther. 8(3): 1-14 (2006).
Keimowitz, Dementia Improvement With Cytotoxic Chemotherapy a Case of Alzheimer Disease and Multiple Myeloma, Arch. Neurol. 54(4): 485-488 (1997).
Kim, et al., Pan-Bcl-2 Inhibitor, GX15-070 (Obatoclax), Decreases Human T Regulatory lymphocytes while Preserving Effector T Lymphocytes: A Rationale for its Use in Combination Immunotherapy, J. Immunol. 192: 2622-2633 (2014).
Kroner, et al., PD-1 Regulates Neural Damage in Oligodendroglia-Induced Inflammation, PLoS ONE 4(2): e4405, pp. 1-9 (2009).
Kunis, et al., IFN-gamma-Dependent Activation of the Brain's Choroid Plexus for CNS Immune Surveillance and Repair, Brain 136: 3427-3440 (2013).
Kunis, et al., Immunization with a Myelin-Derived Antigen Activates the Brain's Choroid Plexus for Recruitment of Immunoregulatory Cells to the CNS and Attenuates Disease Progression in a Mouse Model of ALS, J. Neurosci. 35 (16): 6381-6393 (2015).
Liu et al. Inhibition of p300 Impairs Foxp3(+) T Regulatory Cell Function and Promotes Antitumor Immunity, Nat. Med. 19(9): 1173-1177 (2013).
Mellman, et al., Immunotherapy Comes of Age, Nature 480: 480-489 (2011).
Nebbia, et al., Upregulation of the Tim-3/Galectin-9 Pathway of T Cell Exhaustion in Chronic Hepatitis B Virus Infection, PLoS ONE 7(10): e47648, pp. 1-15 (2012).
Newell, et al., Imaging Resolution and Transient Clinical Improvement Following Cyclophosphamide Treatment of a Cerebral Amyloid Angiopathy-Related Lesion, Alzheimer's & Dementia 8(4): S775-S776 (2012).
Ohaegbulam, et al., Human Cancer Immunotherapy with Antibodies to the PD-1 and PD-L1 Pathway, Trends Mol. Med. 21(1): 24-33 (2015).
Pardoll, et al., The Blockade of Immune Checkpoints in Cancer Immunotherapy, Nat. Rev. Cancer 12: 252-264 (2012).
Peng, et al., PD-1 Blockade Enhances T-Cell Migration to Tumors by Elevating IFN-gamma Inducible Chemokines, Cancer Res. 72(20): 5209-5218 (2012).
Pere, et al., A CCR4 Antagonist Combined with Vaccines Induces Antigen-Specific CD8+ T Cells and Tumor Immunity Against Self Antigens, Blood 118: 4853-4862 (2011).
Qin, et al., MicroRNA-126 Regulates the Induction and Function of CD4(+) Foxp3(+) Regulatory T Cells through PI3K/AKT Pathway, J. Cell. Mol. Med. 17: 252-264 (2013).
Quiroga, et al., Inducible Costimulator: A Modulator of IFN-gamma Production in Human Tuberculosis, J. Immunol. 176: 5965-5974 (2006).
Raynor, et al., Homeostasis and Function of Regulatory T Cells in Aging, Curr. Opin. Immunol. 24: 482-487 (2012).
U.S. Appl. No. 14/797,894, filed Jul. 13, 2015, Mar. 12, 2014, 2016/0000909, U.S. Pat. No. 9,856,318.
U.S. Appl. No. 14/957,065, filed Dec. 2, 2015, Mar. 12, 2014, U.S. Pat. No. 9,394,365.
U.S. Appl. No. 15/190,160, filed Jun. 22, 2016, Mar. 12, 2014, U.S. Pat. No. 9,512,225.
U.S. Appl. No. 15/202,493, filed Jul. 5, 2016, Mar. 12, 2014, U.S. Pat. No. 9,512,227.
U.S. Appl. No. 15/212,231, filed Jul. 16, 2016, Mar. 12, 2014, 2016/0319021, U.S. Pat. No. 9,534,052.
U.S. Appl. No. 15/125,249, filed Sep. 12, 2016, Mar. 12, 2014, 2017/0240634.
U.S. Appl. No. 15/821,570, filed Nov. 22, 2017, Mar. 12, 2014.
U.S. Appl. No. 15/821,603, filed Nov. 22, 2017, Mar. 12, 2014.
U.S. Appl. No. 15/821,672, filed Nov. 22, 2017, Mar. 12, 2014.
U.S. Appl. No. 15/850,794, filed Sep. 10, 2015, Mar. 12, 2014, 2016/0008463.
U.S. Appl. No. 15/821,678, filed Nov. 22, 2017, Mar. 12, 2014.
U.S. Appl. No. 15/261,945, filed Sep. 10, 2016, Mar. 12, 2014, 2017/0029508.
U.S. Appl. No. 15/698,800, filed Sep. 8, 2017, Mar. 12, 2014.
Intlekofer, et al., Preclinical Rationale for CTLA-4 and PD-1 Blockage as Cancer Immunotherapy, J. Leukoc. Biol. 94(1): 25-39 (2013).
Leung, et al., The CD28-B7 Family in Anti-Tumor Immunity: Emerging Concepts in Cancer Immunitherapy, Immune Network 14(6): 265-276 (2014).
McDermott, et al., PD-1 as a Potential Target in Cancer Therapy, Cancer Med. 2(5): 662-673 (2013).
Sakthivel, et al., Attenuation of Immune-Mediated Influenza Pneumonia by Targeting the Inducible Co-Stimulator (ICOS) Molecule on T Cells, PLoS ONE 9(7): e100970, pp. 1-11 (2014).
Simpson, et al., Regulation of CD4 T Cell Activation and Effector Function by Inducible Costimulator (ICOS), Curr. Opin. Immunol. 22: 326-332 (2010).
Reines, et al., Rofecoxib No Effect on Alzheimer's Disease in a 1-Year, Randomized, Blinded, Controlled Study, Neurol. 62: pp. 66-71 (2004).
Reiss et al., Harnessing the Power of the Immune System via Blockade of PD-1 and PD-L1: A Promising New Anticancer Strategy, Immunother. 6(4): 459-475 (2014).
Ren, et al., Programmed Death-1 Pathway Limits Central Nervous System Inflammation and Neurologic Deficits in Murine Experimental Stroke, Stroke 42: 2578-2583 (2011).
Rosenkranz, et al., Higher Frequency of Regulatory T cells in the Elderly and Increased Suppressive Activity in Neurodegeneration, J. Neuroimmunol. 188: 117-127 (2007).
Sakuishi, et al., Targeting Tim-3 and PD-1 Pathways to Reverse T cell Exhaustion and Restore Anti-Tumor Immunity, J. Exp. Med. 207: 2187-2194 (2010).
Salama, et al., Critical Role of the Programmed Death-1 (PD-1) Pathway in Regulation of Experimental Autoimmune Encephalomyelitis, J. Exp. Med. 198(1): 71-78 (2003).

(56) References Cited

OTHER PUBLICATIONS

Saresella, et al., PD1 Negative and PD1 Positive CD4+ T Regulatory Cells in Mild Cognitive Impairment and Alzheimer's Disease, J. Alzheimers Dis. 21: 927-938 (2010).
Saresella, et al., A Potential Role for the PD1/PD-L1 Pathway in the Neuroinflammation of Alzheimer's Disease, Neurobiol. Aging 33: 624.e11-624e22 (2012).
Schreiber, et al., Cancer Immunoediting: Integrating Immunity's Roles in Cancer Suppression and Promotion, Science 331: 1565-1570 (2011).
Schwartz, et al., Therapeutic T Cell-Based Vaccination for Neurodegenerative Disorders, The Role of CD4+ CD25+ Regulatory T cells, Ann. NY Acad. Sci. 1051: 701-708 (2005).
Schwartz, et al., Breaking Peripheral Immune Tolerance to CNS Antigens in Neurodegenerative Diseases: Boosting Autoimmunity to Fight-Off Chronic Neuroinflammation, J. Autoimmun. 54: 8-14 (2014).
Schwartz, et al., The Resolution of Neuroinflammation in Neurodegeneration: Leukocyte Recruitment via the Choroid Plexus, EMBO J. 33(1): 7-22.(2014).
Sharpe, et al., The B7-CD28 Superfamily, Nat. Rev. Immunol. 2: 116-126 (2002).
Shecter, et al., Infiltrating Blood-Derived Macrophages are Vital Cells Playing an Anti-inflammatory Role in Recovery from Spinal Cord Injury in Mice, PLoS Med, 6(1): e1000113, pp. 1-17 (2009).
Shevchenko, et al., Low-Dose Gemcitabine Depletes Regulatory T Cells and Improves Survival in the Orthotopic Panc02 Model of Pancreatic Cancer, Int. J. Cancer 133: 98-107 (2013).
Simpson, et al., Fc-Dependent Depletion of Tumor-Infiltrating Regulatory T Cells Co-Defines the Efficacy of Anti-CTLA-4 Therapy Against Melanoma, J. Exp. Med. 210: 1695-1710 (2013).
Smith, et al., The Microbial Metabolites, Short-Chain Fatty Acids, Regulate Colonic Treg Cell Homeostasis, Science 341: 569-573 (2013).
Terme, et al., Modulation of Immunity by Antiangiogenic Molecules in Cancer, Clin. Develop. Imunol. 2012(492920): 1-8 (2012).
Thomas-Schoemann, et al., Arsenic Trioxide Exerts Antitumor Activity through Regulatory T cell Depletion Mediated by Oxidative Stress in a Murine Model of Colon Cancer, J. Immunol. 189: 5171-5177 (2012).
Voo, et al., Antibodies Targeting Human OX40 Expand Effector T Cells and Block Inducible and Natural Regulatory T Cell Function, J. Immunol. 191: 3641-3650 (2013).
Wainwright, et al., Targeting Tregs in Malignant Brain Cancer: Overcoming IDO, Frontiers Immunol. 4(16): 1-17 (2013).
Wang, et al., PD1 Blockade Reverses the Suppression of Melanoma Antigen-Specific CTL by CD4+CD25 Hi Regulatory T Cells, Int. Immunol. 21(9): 1065-1077 (2009).
Wang, et al., Down-Modulation of Programmed Death 1 Alters Regulatory T Cells and Promotes Experimental Autoimmune Encephalomyelitis, J. Neurosci. Res. 88: 7-15 (2010).
Ward, et al., The Soluble Isoform of CTLA-4 as a Regulator of T-Cell Responses, Eur. J. Immunol. 43: 1274-1285 (2013).
Webster, et al., Frontiers in Genetics, 5(88): 1-23 (2014).
Weiskopf, et al., Improving Macrophage Responses to Therapeutic Antibodies by Molecular Engineering of SIRPalpha Variants, Oncoimmunol. 2(9): e25773-1-e25773-3 (2013).
WIPO, PCT Form ISA210 International Search Report for PCT/IL2015/050265, dated Sep. 28, 2015.
WIPO, PCT Form ISA237 Written Opinion of the International Searching Authority for PCT/IL2015/050265, dated Sep. 28, 2015.
WIPO, PCTForm IB373 International Preliminary Report on Patentability for PCT/IL2015/050265, dated Sep. 22, 2016.
WIPO, PCT Form ISA210 International Search Report for PCT/IL2016/050750, dated Nov. 4, 2016.
WIPO, PCT Form ISA237 Written Opinion of the International Searching Authority for PCT/IL2016/050750, dated Nov. 4, 2016.
WIPO, PCT Form ISA210 International Search Report for PCT/IB2016/001433, dated May 26, 2017.
WIPO, PCT Form ISA237 Written Opinion of the International Searching Authority for PCT/IB2016/001433, dated May 26, 2017.
Zha, et al., Chronic Thoracic Spinal Cord Injury Impairs CD8+ T-Cell Function by Up-Regulating Programmed Cell Death-1 Expression, J. Neuroinflamm. 11(65): 1-18 (2014).
Zhao, et al., Regulation of Neuroinflammation through Programmed Death-1/Programed Death Ligand Signaling in - Neurological Disorders, Frontiers Cell. Neurosci. 8(271): 1-7 (2014).
Zheng, et al., New Approaches to Treating Alzheimer's Disease, Pers. Med. Chem. 7: 1-8 (2015).
Zhu, et al., p300 Exerts an Epigenetic Role in Chronic Neuropathic Pain through its Acetyltransferase Activity in Rats Following Chronic Constriction Injury (CCI), Mol. Pain 8(84): 1-11 (2012).
Zhu, et al., TIM-3 and Its Regulatory Role in Immune Responses, Curr. Top. Microbiol. Immunol. 350: 1-15 (2010).
Ziv, et al., Immune Cells Contribute to the Maintenance of Neurogenesis and Spatial Learning Abilities in Adulthood, Nat. Neurosci. 9(2): 268-275 (2006).

\* cited by examiner

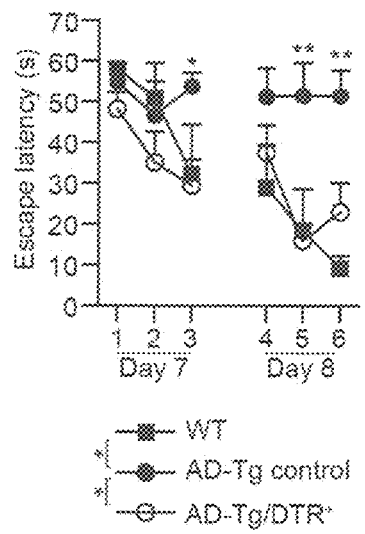
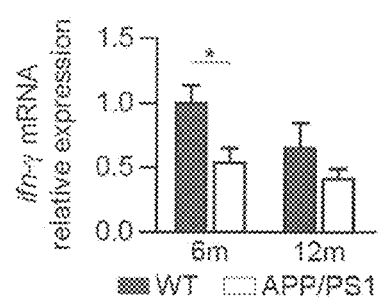
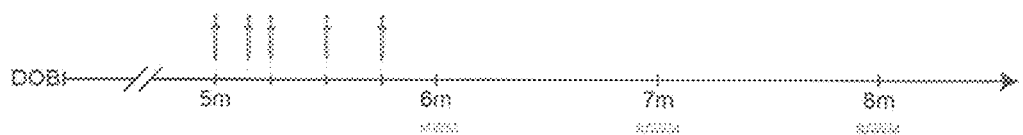

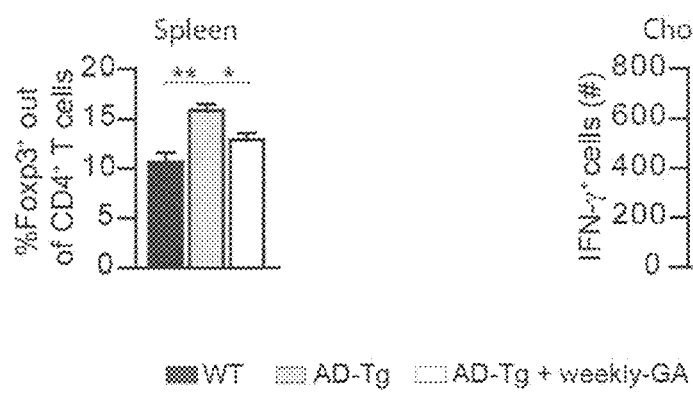
Fig. 9A
Fig. 9B
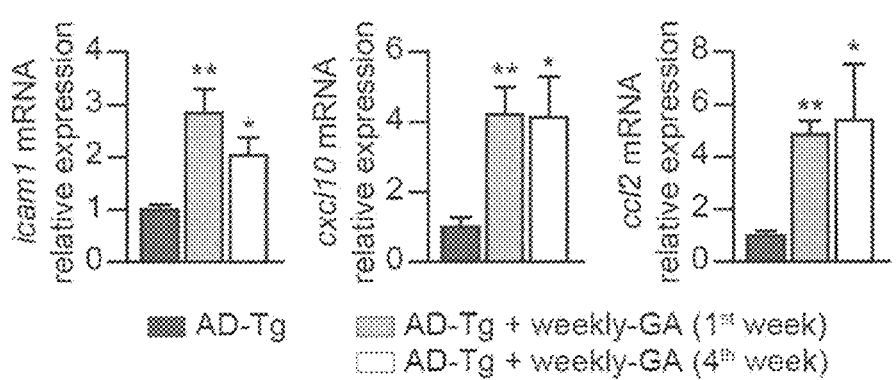
Fig. 9C

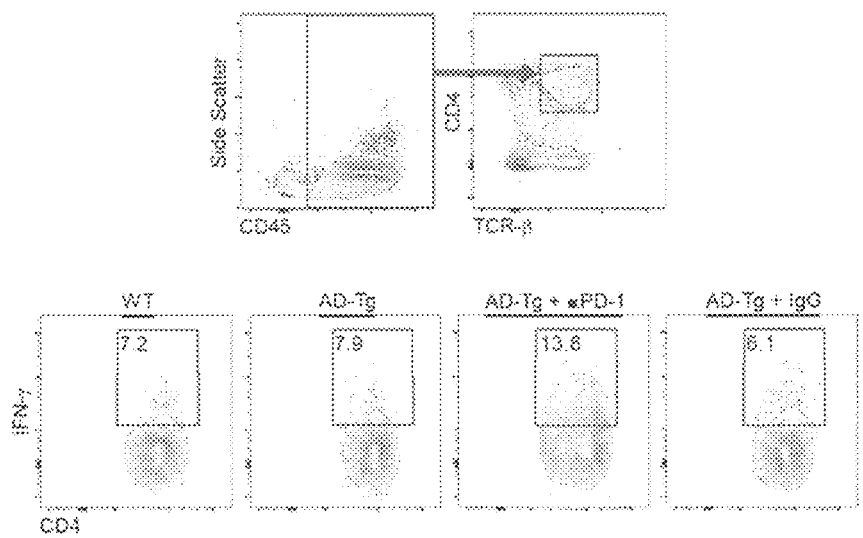
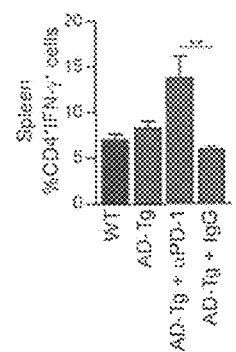
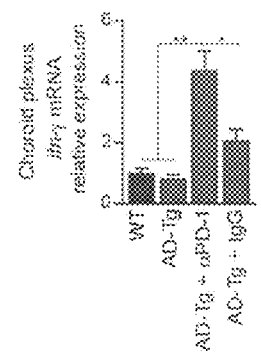
Figure 11A
Figure 11B
Figure 11C

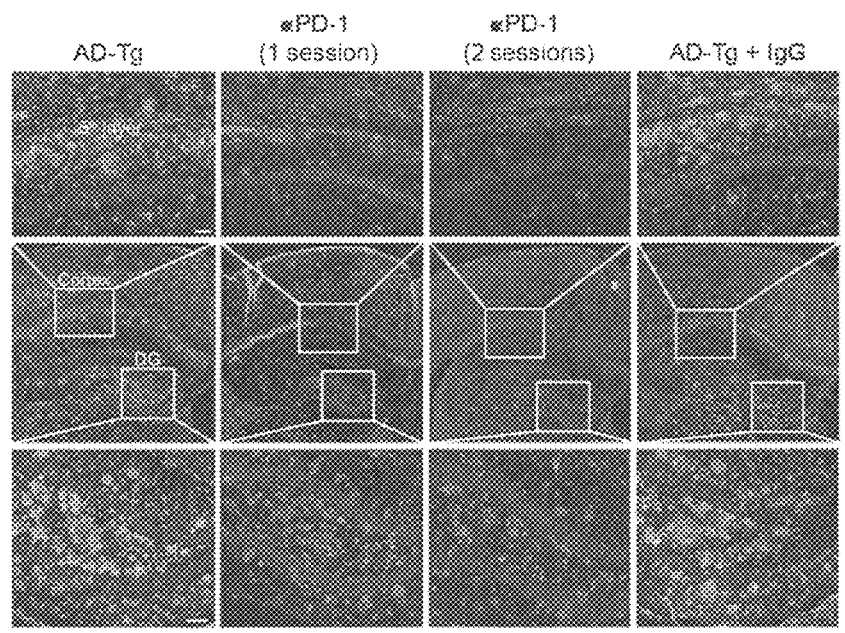

REDUCING SYSTEMIC REGULATORY T CELL LEVELS OR ACTIVITY FOR TREATMENT OF ALZHEIMER'S DISEASE

CROSS-REFERENCE TO RELATED APPLICATIONS

The present application is a continuation that claims priority pursuant to 35 U.S.C. § 120 to U.S. patent application Ser. No. 14/797,894, filed on Jul. 13, 2015, a Continuation-in-Part application that claims priority to International Application No. PCT/IL2015/050265, filed Mar. 12, 2015, in which the United States is designated, and claims the benefit of priority from U.S. Provisional Patent Application No. 61/951,783 filed Mar. 12, 2014 and U.S. Provisional Patent Application No. 62/030,164 filed Jul. 29, 2014, the entire contents of each and all these applications being hereby incorporated by reference herein in their entirety as if fully disclosed herein.

FIELD OF THE INVENTION

The present invention relates in general to methods and compositions for treating disease, disorder, condition or injury of the Central Nervous System (CNS) by transiently reducing the level of systemic immunosuppression in the circulation.

BACKGROUND OF THE INVENTION

Most central nervous system (CNS) pathologies share a common neuroinflammatory component, which is part of disease progression, and contributes to disease escalation. Among these pathologies is Alzheimer's disease (AD), an age-related neurodegenerative disease characterized by progressive loss of memory and cognitive functions, in which accumulation of amyloid-beta (Aβ) peptide aggregates was suggested to play a key role in the inflammatory cascade within the CNS, eventually leading to neuronal damage and tissue destruction (Akiyama et al, 2000; Hardy & Selkoe, 2002; Vom Berg et al, 2012). Despite the chronic neuroinflammatory response in neurodegenerative diseases, clinical and pre-clinical studies over the past decade, investigating immunosuppression-based therapies in neurodegenerative diseases, have raised the question as to why anti-inflammatory drugs fall short (Breitner et al, 2009; Group et al, 2007; Wyss-Coray & Rogers, 2012). We provide a novel answer that overcomes the drawbacks of existing therapies of AD and similar diseases and injuries of the CNS; this method is based on our unique understanding of the role of the different components of systemic and central immune system in CNS maintenance and repair.

SUMMARY OF INVENTION

In one aspect, the present invention provides a pharmaceutical composition comprising an active agent that causes reduction of the level of systemic immunosuppression in an individual for use in treating a disease, disorder, condition or injury of the CNS that does not include the autoimmune neuroinflammatory disease, relapsing-remitting multiple sclerosis (RRMS), wherein said pharmaceutical composition is for administration by a dosage regimen comprising at least two courses of therapy, each course of therapy comprising in sequence a treatment session followed by an interval session of non-treatment.

In another aspect, the present invention provides a method for treating a disease, disorder, condition or injury of the Central Nervous System (CNS) that does not include the autoimmune neuroinflammatory disease relapsing-remitting multiple sclerosis (RRMS), said method comprising administering to an individual in need thereof a pharmaceutical composition comprising an active agent that causes reduction of the level of systemic immunosuppression according to the present invention, wherein said pharmaceutical composition is administered by a dosage regime comprising at least two courses of therapy, each course of therapy comprising in sequence a treatment session followed by an interval session of a non-treatment period.

BRIEF DESCRIPTION OF DRAWINGS

FIGS. 6A-E show the effect of transient depletion of Tregs on Aβ plaques learning/memory performance. (A) Representative microscopic images and (B) quantitative analysis of the brains of 5-month old DTx-treated AD-Tg/Foxp3-DTR$^+$ and AD-Tg/Foxp3-DTR$^-$ control mice, 3 weeks after the last DTx injection, immunostained for Aβ plaques and Hoechst nuclear staining (scale bar, 250 μm). Mean Aβ plaque area and numbers in the hippocampal dentate gyms (DG) and the 5$^{th}$ layer of the cerebral cortex were quantified (in 6 μm brain slices; n=5-6 per group; Student's t test). FIGS. 6C-E) show Morris water maze (MWM) test performance of 6-month old DTx-treated AD-Tg/Foxp3-DTR$^+$ and control mice, 3 weeks after the last DTx injection. Following transient Treg depletion, AD-Tg mice showed better spatial learning/memory performance in the (C) acquisition, (D) probe and (E) reversal phases of the MWM, relative to AD-Tg controls (n=7-9 per group; two-way repeated measures ANOVA followed by Bonferroni post-hoc analysis for individual pair comparisons; *, $P<0.05$ for overall acquisition, probe, and reversal). In all panels, error bars represent mean±s.e.m.; *, $P<0.05$; , $P<0.01$; *, $P<0.001$.

FIG. 7 shows mRNA expression levels of ifn-y, measured by RT-qPCR, in CPs isolated from 6- and 12-month old APP/PS1 AD-Tg mice (a mouse model for Alzheimer's disease (see Materials and Methods)), compared to age-matched WT controls (n=5-8 per group; Student's t test). Error bars represent mean±s.e.m.; *, $P<0.05$.

FIGS. 8A-I show the therapeutic effect of administration of weekly Glatiramer acetate (GA) in AD-Tg mice. (A) Schematic representation of weekly-GA treatment regimen. Mice (5-month old) were s.c. injected with GA (100 μg), twice during the first week (on day 1 and 4), and once every week thereafter, for an overall period of 4 weeks. The mice were examined for cognitive performance, 1 week (MWM), 1 month (RAWM) and 2 months (RAWM, using different experimental spatial settings) after the last injection, and for hippocampal inflammation. FIGS. 8B-D show mRNA expression levels of genes in the hippocampus of untreated AD-Tg mice, and AD-Tg mice treated with weekly-GA, at the age of 6 m, showing (B) reduced expression of pro-inflammatory cytokines such as TNF-α, IL-1β and IL-12p40, (C) elevation of the anti-inflammatory cytokines IL-10 and TGF-β, and of (D) the neurotropic factors, IGF-1 and BDNF, in weekly-GA treated mice (n=6-8 per group; Student's t test). In FIGS. 8E-G, AD-Tg mice (5 months old) were treated with either weekly-GA or with vehicle (PBS), and compared to age-matched WT littermates in the MWM task at the age of 6 m. Treated mice showed better spatial learning/memory performance in the acquisition (E), probe (F) and reversal (G) phases of the MWM, relative to controls (n=6-9 per group; two-way repeated measures ANOVA followed by Bonferroni post-hoc for individual pair comparisons; WT mice, black circles; AD-Tg controls, white circles; treated AD-Tg, grey circles). FIGS. 8H-I show cognitive performance of the same mice in the RAWM task, 1 month (H) or 2 months (I) following the last GA injection (n=6-9 per group; two-way repeated measures ANOVA followed by Bonferroni post-hoc for individual pair comparisons). Data are representative of at least three independent experiments. In all panels, error bars represent mean±s.e.m.; *, $P<0.05$; , $P<0.01$; *, $P<0.001$.

FIGS. 9A-H show further therapeutic effects of administration of weekly-GA in AD-Tg mice. A-B shows 5XFAD AD-Tg mice that were treated with either weekly-GA, or vehicle (PBS), and were examined at the end of the 1$^{st}$ week of the administration regimen (after a total of two GA injections). Flow cytometry analysis for CD4$^+$Foxp3$^+$ splenocyte frequencies (A), and CP IFN-γ-expressing immune cells (B; intracellularly stained and pre-gated on CD45), in treated 6-month old AD-Tg mice, compared to age-matched WT controls (n=4-6 per group; one-way ANOVA followed by Newman-Keuls post hoc analysis). (C) mRNA expression levels for the genes icam1, cxcl10 and ccl2, measured by RT-qPCR, in CPs of 4-month old AD-Tg mice, treated with either weekly-GA or vehicle, and examined either at the end of the 1$^{st}$ or 4$^{th}$ week of the weekly-GA regimen (n=6-8 per group; one-way ANOVA followed by Newman-Keuls post hoc analysis). FIGS. 9D-E show representative images of brain sections from 6-month old AD-Tg/CX$_3$CR1$^{GFP/+}$ BM chimeras following weekly-GA. CX$_3$CR1$^{GFP}$ cells were localized at the CP of the third ventricle (3V; i), the adjacent ventricular spaces (ii), and the CP of the lateral ventricles (LV; iii) in AD-Tg mice treated with weekly-GA (D; scale bar, 25 μm). Representative orthogonal projections of confocal z-axis stacks, showing co-localization of GFP$^+$ cells with the myeloid marker, CD68, in the CP of 7-month old AD-Tg/CX$_3$CR1$^{GFP/+}$ mice treated with weekly-GA, but not in control PBS-treated AD-Tg/CX$_3$CR1$^{GFP/+}$ mice (E; scale bar, 25 μm). (F) CX$_3$CR1$^{GFP}$ cells are co-localized with the myeloid marker IBA-1 in brains of GA-treated AD-Tg/CX$_3$CR1$^{GFP/+}$ mice in the vicinity of Aβ plaques, and co-expressing the myeloid marker, IBA-1 (scale bar, 25 μm). FIGS. 9G-H show representative flow cytometry plots of cells isolated from the hippocampus of 4-month old WT, untreated AD-Tg, and AD-Tg mice, on the 2$^{nd}$ week of the weekly-GA regimen. CD11b$^{high}$/CD45$^{high}$ mo-MΦ were gated (G) and quantified (H; n=4-5 per group; one-way ANOVA followed by Newman-Keuls post hoc analysis). In all panels, error bars represent mean±s.e.m.; *, $P<0.05$; , $P<0.01$; *, $P<0.001$.

In FIGS. 10A-B, aged mice (18 months) were treated with either p300i or vehicle (DMSO) for a period of 1 week, and examined a day after cessation of treatment. Representative flow cytometry plots showing elevation in the frequencies of CD4$^+$ T cells expressing IFN-γ in the spleen (A), and IFN-γ-expressing immune cell numbers in the CP (B), following p300i treatment. FIGS. 10C-E show representative microscopic images (C), and quantitative analysis, of Aβ plaque burden in the brains of 10-month old AD-Tg mice, which received either p300i or vehicle (DMSO) for a period of 1 week, and were subsequently examined after 3 additional weeks. Brains were immunostained for Aβ plaques and by Hoechst nuclear staining (n=5 per group; Scale bar, 250 μm). Mean Aβ plaque area and plaque numbers were quantified in the hippocampal DG (D) and the $5^{th}$ layer of the cerebral cortex (E) (in 6 μm brain slices; n=5-6 per group; Student's t test). (F) Schematic representation of the p300i treatment (or DMSO as vehicle) administration regimen to the different groups of AD-Tg mice at the age of 7 months, in either 1 or 2 sessions. FIGS. 10G-H show the change mean of Aβ plaque percentage coverage of the cerebral cortex ($5^{th}$ layer) (G), and the change in mean cerebral soluble $Aβ_{1-40}$ and $Aβ_{1-42}$ protein levels (H), relative to the untreated AD-Tg group ($Aβ_{1-40}$ and $Aβ_{1-42}$ mean level in untreated group, 90.5±11.2 and 63.8±6.8 pg/mg total portion, respectively; n=5-6 per group; one-way ANOVA followed by Newman-Keuls post hoc analysis). In all panels, error bars represent mean±s.e.m.; *, $P<0.05$; , $P<0.01$; *, $P<0.001$.

FIGS. 13A-D depict representative microscopic images showing that PD-1 blockade mitigates AD pathology (A), and quantitative analyses (B, C, D), of Aβ plaque burden and astrogliosis in the brains of AD-Tg mice, which were treated at the age of 10-months with either anti-PD-1 (in 1 or 2 sessions, as depicted in FIG. 12a-b) or IgG control, and subsequently examined at the age of 12 months. Brains were immunostained for Aβ plaques (in red), GFAP (marking astrogliosis, in green), and by Hoechst nuclear staining (n=4-5 per group; Scale bar, 50 μm). Mean Aβ plaque area and plaque numbers were quantified in the hippocampal dentate gyrus (DG) and the $5^{th}$ layer of the cerebral cortex, and GFAP immunoreactivity was measured in the hippocampus (in 6 μm brain slices; n=5-6 per group; Student's t test). In all panels, error bars represent mean±s.e.m.; *, $P<0.05$; , $P<0.01$; *, $P<0.001$.

DETAILED DESCRIPTION

Figure 1A:
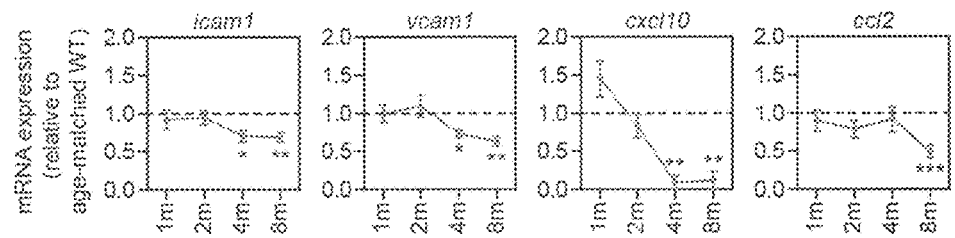
FIGS. 1A-B depict the choroid plexus (CP) activity along disease progression in the 5XFAD transgenic mouse model of AD (AD-Tg). (A) mRNA expression levels for the genes icam1, vcam1, cxcl10 and cc12, measured by RT-qPCR, in CPs isolated from 1, 2, 4 and 8-month old AD-Tg mice, shown as fold-change compared to age-matched WT controls (n=6-8 per group; Student's t test for each time point). (B) Representative microscopic images of CPs of 8-month old AD-Tg mice and age-matched WT controls, immunostained for the epithelial tight junction molecule Claudin-1, Hoechst nuclear staining, and the integrin lignad, ICAM-1 (scale bar, 50 μm). In all panels, error bars represent mean±s.e.m.; *, $P<0.05$; , $P<0.01$; *, $P<0.001$.

Immune checkpoint mechanisms, which include cell-intrinsic downregulation of activated T cell responsiveness and effector function by inhibitory receptors, maintain systemic immune homeostasis and autoimmune tolerance (Joller et al, 2012; Pardoll, 2012). In recent years, blockade of these immune checkpoints, such as the programmed death-1 (PD-1) pathway (Francisco et al, 2010), has demonstrated notable anti-tumor efficacy, highlighting the potential of unleashing the power of the immune system in fighting various malignancies (Postow et al, 2015). Similarly, the findings disclosed herein (Example 5) provide the first evidence of the therapeutic potential of immune checkpoint blockade in a neurodegenerative disease, such as AD. Though breaking tolerance is now widely accepted in cancer immunotherapy (Lesokhin et al, 2015; Mellman et al, 2011; Schreiber et al, 2011), this approach in treating chronic neurodegenerative diseases has been overlooked. It is disclosed herein that in AD-Tg mice, breaking immune tolerance by PD-1 blockade resulted in a systemic IFN-γ-associated response, as was described in cancer immunotherapy (Lesokhin et al, 2015; Peng et al, 2012). The inventors also found that PD-1 blockade had a tissue-specific effect of IFN-γ response at the CP. Such response was previously shown by the inventors to be essential for driving CNS repair processes through an immunological mechanism involving enhanced CNS immune surveillance in mouse models of acute (Kunis et al, 2013; Shechter et al, 2013) and chronic (Baruch et al, 2015; Kunis et al, 2015) neurodegeneration. Testing the effect on cerebral Aβ plaque pathology, it is disclosed herein that a single treatment session utilizing PD-1 blockade led to a significant reduction in plaque burden that lasted for at least 2 months, the last time point tested. Notably, an additional treatment session with anti-PD-1, a month after the initial treatment, was necessary to maintain the effect on cognitive performance. These findings suggest that for long-term efficacy, repeated treatment sessions should be considered, at intervals to be determined in further studies.

Relief of systemic immune suppression may be achieved by means other than release of immune checkpoints, for example by a decrease in systemic regulatory T cells, or attenuating their activity. Thus, it has further been found in accordance with the present invention that a short-term transient depletion of $Foxp3^+$ regulatory T cells (Tregs) in a mouse model of Alzheimer's disease (AD-Tg mice) results in improved recruitment of leukocytes to the CNS through the brain's choroid plexus, elevated numbers of CNS-infiltrating anti-inflammatory monocyte-derived macrophages mo-MΦ and $CD4^+$ T cells, and a marked enrichment of $Foxp3^+$ Tregs that accumulates within the brain. Furthermore, the long-term effect of a single session of treatment lead to a reduction in hippocampal gliosis and reduced mRNA expression levels of pro-inflammatory cytokines within the brain. Importantly, the effect on disease pathology includes reduced cerebral amyloid beta (Aβ) plaque burden in the hippocampal dentate gyrus, and the cerebral cortex ($5^{th}$ layer), two brain regions exhibiting robust Aβ plaque pathology in the AD-Tg mice. Most importantly, the short-term transient depletion of Tregs is followed by a dramatic improvement in spatial learning and memory, reaching cognitive performance similar to that of wild type mice (Examples 2 and 3). Taken together, these findings demonstrate that a short session of Treg depletion, followed by a period of no intervention, results in transiently breaking Treg-mediated systemic immune suppression in AD-Tg mice, which enables recruitment of inflammation-resolving cells, mo-MΦ and Tregs, to the brain, and lead to resolution of the neuroinflammatory response, clearance of Aβ, and reversal of cognitive decline.

These findings strongly argue against the common wisdom in this field of research, according to which increasing systemic immune suppression would result in mitigation of the neuroinflammatory response. On the contrary, our findings show that boosting of the systemic response, by a short-term, brief and transient, reduction in systemic Treg-mediated suppression or release of restraints on the immune system in the form of immune checkpoints, is needed in order to achieve inflammation-resolving immune cell accumulation, including Tregs themselves, within the brain, thus fighting off AD pathology.

The specificity of the inventors approach presented herein has been substantiated by using several independent experimental paradigms, as detailed below. Briefly, first the inventors used an immunomodulatory compound in two different administration regimens that led to opposite effects on peripheral Treg levels, on CP activation, and on disease pathology; a daily administration regimen that augments peripheral Treg levels (Weber et al, 2007), and a weekly administration regimen, which they found to reduce peripheral Treg levels (Example 3). The inventors also provide a direct functional linkage between peripheral Treg levels and disease pathology when demonstrating in AD-Tg mice, by either transient in vivo genetic depletion of Tregs (Example 2), or by pharmacologic inhibition of their Foxp3 function (Examples 3 and 4), that these manipulations result in activation of the CP for facilitating leukocyte trafficking to the CNS, inflammation-resolving immune cell accumulation at sites of pathology, clearance of cerebral Aβ plaques, and skewing of the immunological milieu of the brain parenchyma towards the resolution of inflammation.

It has further been found in accordance with the present invention that infrequent administration of a universal antigen, Copolymer-1, for a limited period of time (representing one session of treatment) reduces Treg-mediated systemic immune suppression, and improves selective infiltration of leukocytes into the CNS by increasing the brain's choroid plexus gateway activity, leading to dramatic beneficial effect in Alzheimer's disease pathology (Example 3), while daily administration of Copolymer 1, that enhance Treg immune suppression (Hong et al, 2005; Weber et al, 2007), showed no beneficial effect, or even some modest detrimental effect, on disease pathology (Example 5 in PCT/IL2015/050265). The inventors of the present invention further show herein that direct interference with Foxp3 Treg activity, either by inhibition of p300 with a specific small molecule inhibitor (p300i), or interaction with the PD-1 receptor by an anti-PD-1 antibody, improves choroid plexus gateway activity in AD-Tg mice, and mitigates Alzheimer's disease pathology (Example 4).

Importantly, each of these examples provided by the inventors, demonstrate a different intervention which causes short term reduction in systemic immune suppression: Copolymer-1 acts as an immunomodulatory compound, p300i as a small molecule which decreases Foxp3 acetylation and Treg function, and anti-PD-1 is used as a neutralizing antibody for PD-1 expressed on Tregs and as a immune checkpoint blocker. These therapeutic approaches were used for a short session of treatment that transiently augmented immune response in the periphery, mainly by elevation of peripheral IFN-γ levels and IFN-γ-producing cells, thus activating the brain's choroid plexus allowing selective infiltration of T cells and monocytes into the CNS, and homing of these cells to sites of pathology and neuroinflammation. It was also found herein that repeated sessions of treatment interrupted by interval sessions of non-treatment dramatically improve the efficacy of the treatment relative to a single session of treatment (Example 4). The following time interval of non-treatment allowed transient augmentation in Treg levels and activities within the brain, facilitating the resolution of neuroinflammation, and inducing environmental conditions in favor of CNS healing and repair, subsequently leading to tissue recovery. In each of these cases the effect on brain pathology was robust, involving the resolution of the neuroinflammatory response, amyloid beta plaque clearance from AD mice brains, and reversal of cognitive decline. The specificity of the current approach has further been substantiated using a genetic model of transient depletion of Foxp3$^+$ regulatory T cells, in transgenic mouse model of AD (Example 2).

Thus, it has been found in accordance with the present invention that systemic immunosuppression interferes with ability to fight off AD pathology, acting at least in part, by inhibiting IFN-γ-dependent activation of the CP, needed for orchestrating recruitment of inflammation-resolving leukocytes to the CNS (Schwartz & Baruch, 2014b). Systemic Tregs are crucial for maintenance of autoimmune homeostasis and protection from autoimmune diseases (Kim et al, 2007). However, our findings suggest that under neurodegenerative conditions, when a reparative immune response is needed in the brain, the ability to mount this response is interfered with by systemic Tregs or some other factor that can be overcome by immune checkpoint blockade. Nevertheless according to our results, Tregs are needed within the brain, home to sites of neuropathology, and perform locally an anti-inflammatory activity. The present invention represents a unique and unexpected solution for the apparent contradictory needs in fighting off progressive neuronal death as in AD; transiently reducing/inhibiting Tregs in the circulation on behalf of increasing Tregs in the diseased brain. Hence, a short-term and transient reduction in peripheral immune suppression, which allows the recruitment of anti-inflammatory cells, including Tregs and mo-MΦ, to sites of cerebral plaques, leads to a long-term effect on pathology. Notably, however, a transient reduction of systemic Treg levels or activities or transient immune checkpoint blockade may contribute to disease mitigation via additional mechanisms, including supporting a CNS-specific protective autoimmune response (Schwartz & Baruch, 2014a), or augmenting the levels of circulating monocytes that play a role in clearance of vascular Aβ (Michaud et al, 2013).

Though neurodegenerative diseases of different etiology, share a common local neuroinflammatory component, our results strongly argue against simplistic characterization of all CNS pathologies as diseases that would uniformly benefit from systemic anti-inflammatory therapy. Thus, while autoimmune inflammatory brain pathologies, such as Relapsing-Remitting Multiple Sclerosis (RRMS), benefit from continuous systemic administration of anti-inflammatory and immune-suppressive drugs to achieve long lasting peripheral immune suppression, it will either be ineffective or detrimentally affect (Example 5 in PCT/IL2015/050265) pathology in chronic neurodegenerative diseases such as in the case of AD, primary progressive multiple sclerosis (PP-MS) and secondary-progressive multiple sclerosis (SP-MS). Moreover, our findings shed light on the misperception regarding the role of systemic vs. tissue-associated Tregs in these pathologies (He & Balling, 2013). Since the immune-brain axis is part of life-long brain plasticity (Baruch et al, 2014), and neurodegenerative diseases are predominantly age-related, our present findings also point to a more general phenomenon, in which systemic immune suppression interferes with brain function. Accordingly, short-term periodic courses of reducing systemic immune suppression may represent a therapeutic or even preventive approach, applicable to a wide range of brain pathologies, including AD and age-associated dementia.

Importantly, the inventors approach and findings present herein in AD mouse models, do not directly target any disease-specific factor in AD, such as amyloid beta or tau pathology, but rather demonstrate a novel approach which is expected to be clinically applicable in a wide range of CNS pathologies—transient reduction of systemic Treg-mediated immune suppression or release of systemic immune suppression by blockade of immune checkpoints—in order to augment recruitment of inflammation-resolving immune cells to sites of pathology within the CNS.

In view of the unexpected results described above, the present invention provides a method for treating a disease, disorder, condition or injury of the Central Nervous System (CNS) that does not include the autoimmune neuroinflammatory disease relapsing-remitting multiple sclerosis (RRMS), said method comprising administering to an individual in need thereof an active agent that causes reduction of the level of systemic immunosuppression, wherein said active agent is administered by a dosage regime comprising at least two courses of therapy, each course of therapy comprising in sequence a treatment session followed by an interval.

In another aspect, the present invention is directed to an active agent that causes reduction of the level of systemic immunosuppression in an individual, or a pharmaceutical composition comprising the active agent, for use in treating a disease, disorder, condition or injury of the CNS that does not include the autoimmune neuroinflammatory disease, relapsing-remitting multiple sclerosis (RRMS), wherein said pharmaceutical composition is for administration by a dosage regimen comprising at least two courses of therapy, each course of therapy comprising in sequence a treatment session followed by an interval session of non-treatment.

In certain embodiments, the dosage regimen is calibrated such that the level of systemic immunosuppression is transiently reduced.

The term "treating" as used herein refers to means of obtaining a desired physiological effect. The effect may be therapeutic in terms of partially or completely curing a disease and/or symptoms attributed to the disease. The term refers to inhibiting the disease, i.e. arresting or slowing its development; or ameliorating the disease, i.e. causing regression of the disease.

The term "non-treatment session" is used interchangeably herein with the term "period of no treatment" and refers to a session during which no active agent is administered to the individual being treated.

The term "systemic presence" of regulatory or effector T cells as used herein refers to the presence of the regulatory or effector T cells (as measured by their level or activity) in the circulating immune system, i.e. the blood, spleen and lymph nodes. It is a well-known fact in the field of immunology that the cell population profile in the spleen is reflected in the cell population profile in the blood (Zhao et al, 2007).

The present treatment is applicable to both patients that show elevation of systemic immune suppression, as well as to patients that do not show such an elevation. Sometimes the individual in need for the treatment according to the present invention has a certain level of peripheral immunosuppression, which is reflected by elevated frequencies or numbers of Tregs in the circulation, and/or their enhanced functional activity and/or a decrease in IFNγ-producing leukocytes and/or decreased proliferation of leukocytes in response to stimulation. The elevation of frequencies or numbers of Tregs can be in total numbers or as percentage of the total CD4 cells. For example, it has been found in accordance with the present invention that an animal model of Alzheimer's disease has higher frequencies of Foxp3 out of CD4 cells as compared with wild-type mice. However, even if the levels of systemic Treg cells is not elevated, their functional activity is not enhanced, the level of IFNγ-producing leukocytes is not reduced or the proliferation of leukocytes in response to stimulation is not decreased, in said individual, the method of the present invention that reduces the level or activity of systemic immunosuppression is effective in treating disease, disorder, condition or injury of the CNS that does not include the autoimmune neuroinflammatory disease RRMS. Importantly, said systemic immune suppression can also involve additional immune cell types except of Tregs, such as myeloid-derived suppressor cells (MDSCs) (Gabrilovich & Nagaraj, 2009).

The level of systemic immunosuppression may be detected by various methods that are well known to those of ordinary skill in the art. For example, the level of Tregs may be measured by flow cytometry analysis of peripheral blood mononuclear cells or T lymphocytes, immunostained either for cellular surface markers or nuclear intracellular markers of Treg (Chen & Oppenheim, 2011), CD45, TCR-β, or CD4 markers of lymphocytes, and measuring the amount of antibody specifically bound to the cells. The functional activity of Tregs may be measured by various assays; For example the thymidine incorporation assay is being commonly used, in which suppression of anti-CD3 mAb stimulated proliferation of $CD4^+$ $CD25^-$ T cells (conventional T cells) is measured by [$^3$H]thymidine incorporation or by using CFSE (5-(and 6)-carboxyfluorescein diacetate succinimidyl ester, which is capable of entering the cells; cell division is measured as successive halving of the fluorescence intensity of CFSE). The number of IFNγ-producing leukocytes or their activity or their proliferation capacity can easily be assessed by a skilled artisan using methods known in the art; For example, the level of IFNγ-producing leukocytes may be measured by flow cytometry analysis of peripheral blood mononuclear cells, following short ex-vivo stimulation and golgi-stop, and immunostaining by IFNγ intracellular staining (using e.g., BD Biosciences Cytofix/Cytoperm™ fixation/permeabilization kit), by collecting the condition media of these cells and quantifying the level of secreted cytokines using ELISA, or by comparing the ratio of different cytokines in the condition media, for example IL2/IL10, IL2/IL4, INFγ/TGFβ, etc. The levels of MDSCs in the human peripheral blood easily can be assessed by a skilled artisan, for example by using flow cytometry analysis of frequency of $DR^-/LIN^-/CD11b+$, $DR^-/LIN^-/CD15+$, $DR^-/LIN^-/CD33+$ and DR(-/low)/CD14+ cells, as described (Kotsakis et al, 2012).

In humans, the peripheral/systemic immunosuppression may be considered elevated when the total number of Tregs in the circulation is higher than 10, 20, 30, 40, 50, 60, 70, 80, 90, or 100% or more than in a healthy control population, the percentage of Treg cells out of the total CD4+ cells is elevated by 10, 20, 30, 40, 50, 60, 70, 80, 90, or 100% or more than in a healthy control population, or the functional activity of Tregs is elevated by 10, 20, 30, 40, 50, 60, 70, 80, 90, or 100% or more than in a healthy control population. Alternatively, the peripheral/systemic immunosuppression may be considered elevated when the level of IFNγ-producing leukocytes or their activity is reduced relative to that of a healthy control population by 10, 20, 30, 40, 50, 60, 70, 80, 90 or 100%; or the proliferation of leukocytes in response to stimulation is reduced relative to that of a healthy control population by 10, 20, 30, 40, 50, 60, 70, 80, 90 or 100%.

An agent may be considered an agent that causes reduction of the level of systemic immunosuppression when, upon administration of the agent to an individual, the total number of Tregs in the circulation of this individual is reduced by 10, 20, 30, 40, 50, 60, 70, 80, 90 or 100% as compared with the level before administration of the agent, the percentage of Treg cells out of the total CD4+ cells drops by 10, 20, 30, 40, 50, 60, 70, 80, 90 or 100% relative to that of a healthy control population or the functional activity of Tregs is reduced by 10, 20, 30, 40, 50, 60, 70, 80, 90 or 100% as compared with the level before administration of the agent. Alternatively, an agent may be considered an agent that causes reduction of the level of systemic immunosuppression when, upon administration of the agent to an individual, the total number of IFNγ-producing leukocytes or their activity is increased by 10, 20, 30, 40, 50, 60, 70, 80, 90, or 100% or more; or the proliferation of leukocytes in response to stimulation is increased relative to that of a healthy control population by 10, 20, 30, 40, 50, 60, 70, 80, 90 or 100% or more.

In certain embodiments, the active agent causes reduction of the level of systemic immunosuppression by release of a restraint imposed on the immune system by one or more immune checkpoints, for example by blockade of the one or more immune checkpoints.

In certain embodiments, the reduction of the level of systemic immunosuppression is associated with an increase in systemic presence or activity of IFNγ-producing leukocytes.

In certain embodiments, the active agent causes reduction of the level of systemic immunosuppression and thereby an increase in the systemic presence or activity of effector T cells.

The checkpoints that may be manipulated to release the systemic immunosuppression are referred to herein as a pair of an immune check point receptor and its native ligand, except when one partner of the pair is unknown, in which case only the known partner is referred to. For example, PD1, which has two known ligands is referred to herein as "PD1-PDL1" or "PD1-PDL2", while B7H3, the ligand of which has not yet been identified, is referred to simply by "B7H3".

The checkpoints that may be manipulated to release the systemic immunosuppression in accordance with the present invention may be selected from the group consisting of PD1-PDL1, PD1-PDL2, CD28-CD80, CD28-CD86, CTLA4-CD80, CTLA4-CD86, ICOS-B7RP1, B7H3, B7H4, B7H7, B7-CD28-like molecule, BTLA-HVEM, KIR-MHC class I or II, LAG3-MHC class I or II, CD137-CD137L, OX40-OX40L, CD27-CD70, CD40L-CD40, TIM3-GAL9, V-domain Ig suppressor of T cell activation (VISTA), STimulator of INterferon Genes (STING), T cell immunoglobulin and immunoreceptor tyrosine-based inhibitory motif domain (TIGIT), A2aR-Adenosine and indoleamine-2,3-dioxygenase (IDO)-L-tryptophan.

Agents capable of blocking immune checkpoints are known in the art (Colombo & Piconese, 2007) and these agents can be used in accordance with the present invention. Each one of the cited publications below, and Pardoll, 2012, is incorporated by reference as if fully disclosed herein.

In certain embodiments, the active agent that may be used according to the present invention may be selected from the group consisting of:

(i) an antibody selected from the group consisting of: (a) anti-PD-1, (b) anti-PD-L1, (c) anti-PD-L2 (Coyne & Gulley, 2014; Duraiswamy et al, 2014; Zeng et al, 2013); (d) anti-CTLA-4 (Simpson et al, 2013; Terme et al, 2012); (e) anti-CD80; (f) anti-CD86; (g) anti-B7RP1; (h) anti-B7-H3; (i) anti-B7-H4; (j) anti-BTLA; (k) anti-HVEM; (l) anti-CD137; (m) anti-CD137L; (n) anti-CD-27; (o) anti-CD70; (p) anti-CD40; (q) anti-CD40L; (r) anti-OX40 (Voo et al, 2013); (s) anti-OX40L; (t) anti-TIM-3/Galectin9; (u) anti-killer-cell immunoglobulin-like receptor (Ju et al, 2014); (v) anti-LAG-3; and (w) any combination of (a) to (v);

(ii) any combination of (a) to (v) in combination with an adjuvant, such as anti-CTLA-4 antibody in combination with anti OX40 antibody and a TLR9 ligand such as CpG (Marabelle et al, 2013);

(iii) a small molecule selected from the group consisting of: (a) a p300 inhibitor (Liu et al, 2013), such as gemcitabine (low dose) (Shevchenko et al, 2013), or C646 or analogs thereof, i.e. a compound of the formula I:

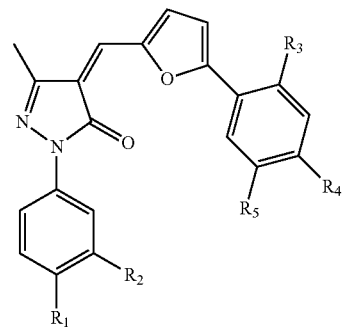

wherein
$R_1$ is selected from H, —$CO_2R_6$, —$CONR_6R_7$, —$SO_3H$, or —$SO_2NR_6R_7$;
$R_2$ is selected from H, —$CO_2R_6$, or halogen, preferably Cl;
$R_3$ is selected from halogen, preferably F, —$NO_2$, —CN, —$CO_2R_6$, preferably $CO_2CH_3$ or $CO_2CH_2CH_3$, or —$CH_2OH$;
$R_4$ and $R_5$ each independently is H or —$C_1$-$C_6$ alkyl, preferably methyl;
$R_6$ is H or —$C_1$-$C_6$ alkyl, preferably H, methyl or ethyl; and
$R_7$ is H or —$C_1$-$C_6$ alkyl, preferably H or methyl (see (Bowers et al, 2010));

(b) Sunitinib (Terme et al, 2012); (c) Polyoxometalate-1 (POM-1) (Ghiringhelli et al, 2012); (d) α,β-methyleneadenosine 5'-diphosphate (APCP) (Ghiringhelli et al, 2012); (e) arsenic trioxide ($As_2O_3$) (Thomas-Schoemann et al, 2012); (f) GX15-070 (Obatoclax) (Kim et al, 2014); (g) a retinoic acid antagonist such as Ro 41-5253 (a synthetic retinoid and selective small molecule antagonist) (Galvin et al, 2013) or LE-135 (Bai et al, 2009); (h) an SIRPα (CD47) antagonist, such as CV1-hIgG4 (SIRPα variant) as sole agent or in combination with anti-CD47 antibody (Weiskopf et al, 2013); (i) a CCR4 antagonist, such as AF399/420/18025 as sole agent or in combination with anti-CCR4 antibody (Pere et al, 2011); (j) an adenosine receptor antagonist; (k) an adenosine A1 receptor antagonist; an adenosine A2a receptor; (m) an adenosine A2b receptor antagonist; (n) an A3 receptor antagonist; (o) an antagonist of indoleamine-2,3-dioxygenase; and (p) an HIF-1 regulator;

(iv) any combination of (iii) (a-p) and (i) (a-v);

(v) a protein selected from the group consisting of: (a) Neem leaf glycoprotein (NLGP; (Roy et al, 2013)); and (b) sCTLA-4 (soluble isoform of CTLA-4) (Ward et al, 2013);

(vi) a silencing molecule selected from the group consisting of miR-126 antisense (Qin et al, 2013) and anti-galectin-1 (Gal-1; (Dalotto-Moreno et al, 2013));

(vii) OK-432 (lyophilized preparation of Streptococcus pyogenes) (Hirayama et al, 2013);

(viii) a combination of IL-12 and anti-CTLA-4;

(ix) an antibiotic agent such as vancomycin (Brestoff & Artis, 2013; Smith et al, 2013); or (x) any combination of (i) to (viii).

In certain embodiments, the agent is an anti-PD-1 antibody, i.e. an antibody specific for PD-1.

Many anti-PD-1 antibodies are known in the art. For example, the anti-PD-1 antibody used in accordance with the present invention may be selected from those disclosed in Ohaegbulam et al. (Ohaegbulam et al, 2015), the entire contents of which being hereby incorporated herein by reference, i.e. CT-011 (pidilizumab; Humanized IgG1; Curetech), MK-3475 (lambrolizumab, pembrolizumab; Humanized IgG4; Merck), BMS-936558 (nivolumab; Human IgG4; Bristol-Myers Squibb), AMP-224 (PD-L2 IgG2a fusion protein; AstraZeneca), BMS-936559 (Human IgG4; Bristol-Myers Squibb), MEDI4736 (Humanized IgG; AstraZeneca), MPDL3280A (Human IgG; Genentech), MSB0010718C (Human IgG1; Merck-Serono); or the antibody used in accordance with the present invention may be MEDI0680 (AMP-514; AstraZeneca) a humanized IgG4 mAb.

In certain embodiments, the CT-011 antibody may be administered to a human at a dosage of 0.2-6 mg/kg or between 1.5-6 mg/kg; the MK-3475 antibody may be administered to a human at a dosage of 1-10 mg/kg; BMS-936558 may be administered to a human at a dosage of 0.3-20 mg/kg, 0.3-10 mg/kg, 1-10 mg/kg or at 1 or 3 mg/kg; BMS-936559 may be administered to a human at a dosage of 0.3-10 mg/kg; MPDL3280A may be administered to a human at a dosage of 1-20 mg/kg; MEDI4736 may be administered to a human at a dosage of 0.1-15 mg/kg; and MSB0010718C may be administered to a human at a dosage of 1-20 mg/kg.

The anti-CTLA4 antibody may be Tremelimumab (Pfizer), a fully human IgG2 monoclonal antibody; or ipilimumab, a fully human human IgG1 monoclonal antibody.

The anti-killer-cell immunoglobulin-like receptors (KIR) antibody may be Lirilumab (BMS-986015; developed by Innate Pharma and licensed to Bristol-Myers Squibb), a fully human monoclonal antibody.

The anti-LAG-3 antibody is directed against lymphocyte activation gene-3. One such antibody that may be used according to the present invention is the monoclonal antibody BMS-986016 (pembrolizumab; Humanized IgG4; Merck).

TABLE 1*

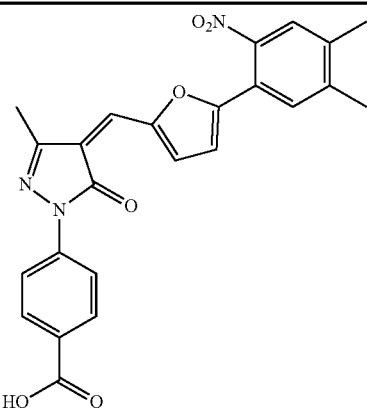

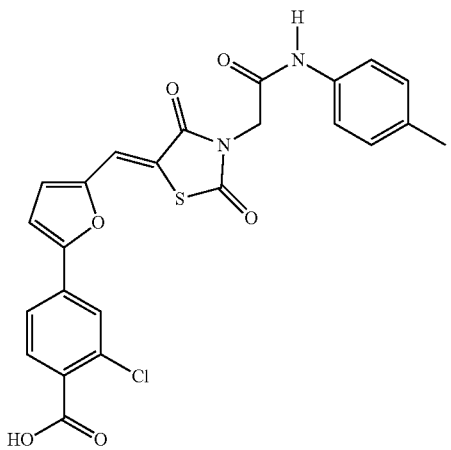 [SMILES: Cc1ccc(NC(=O)CN2C(=O)S/C(=C\c3ccc(-c4ccc(C(=O)O)c(Cl)c4)o3)C2=O)cc1]

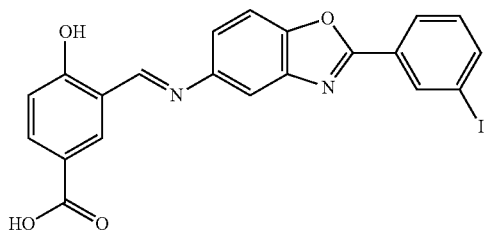 [SMILES: O=C(O)c1ccc(O)c(/C=N/c2ccc3oc(-c4cccc(I)c4)nc3c2)c1]

*Based on Bowers et al. (2010)

In certain embodiments, combinations of antibodies may be used such as but not limited to: CT-011 in combination with Rituximab (trade names Rituxan, MabThera and Zytux) a chimeric monoclonal antibody against the protein CD20, for example, each at 3 mg/kg; BMS-936558 (for example 1 mg/kg) in combination with ipilimumab; for example at 3 mg/kg); or BMS-936558 (e.g. 1-10 mg/kg) in combination with a an HLA-A*0201-restricted multipeptide vaccine (Weber et al, 2013).

In certain embodiments, the agent is a p300 inhibitor, which formulas are listed in Table 1, i.e. C646 (4-(4-((5-(4, 5-dimethyl-2-nitrophenyl)furan-2-yl)methylene)-3-methyl-5-oxo-4,5-dihydro-1H-pyrazol-1-yl)benzoic acid), C146 (4-hydroxy-3-(((2-(3 odophenyl)benzo[d]oxazol-5-yl) imino)methyl)benzoic acid) or C375 (2-chloro-4-(5-((2,4-dioxo-3-(2-oxo-2-(p-tolylamino)ethyl)thiazolidin-5-ylidene)methyl)furan-2-yl)benzoic acid). In particular, the p300 inhibitor is C646.

In certain embodiments, the adenosine receptor antagonist may be CGS15943 (9-Chloro-2-(2-furanyl)-[1,2,4]triazolo [1,5-c]quinazolin-5-amine); the adenosine A1 receptor antagonist may be PSB 36 (1-Butyl-8-(hexahydro-2,5-methanopentalen-3a(1H)-yl)-3,7-dihydro-3-(3-ydroxypropyl)-1H-purine-2,6-dione); the adenosine A2a receptor antagonist may be SCH58261 (5-Amino-7-(2-phenylethyl)-2-(2-furyl)-pyrazolo(4,3-e)-1,2,4-triazolo(1,5-c)pyrimidine), SYN115 (4-Hydroxy-N-[4-methoxy-7-(4-morpholinyl)-2-benzothiazolyl]-4-methyl-1-piperidinecarboxamide), SPTP (also called SCH58261 (5-amino-7-[2-(4-fluorosulfonyl)phenylethyl]-2-(2-furyl)-pryazolo[4,3-ε]-1,2,4-triazolo [1,5-c]pyrimidine), SCH442416 (2-(2-Furanyl)-7-[3-(4-methoxyphenyl)propyl]-7H-pyrazolo[4,3-e][1,2,4]triazolo [1,5-c]pyrimidin-5-amine), or ZM241385 (also called tozadenant (4-Hydroxy-N-(4-methoxy-7-morpholinobenzo [d]thiazol-2-yl)-4-methylpiperidine-1-carboxamide); the adenosine A2b receptor antagonist may be PSB 603 (8-{4-[4-(4-chlorophenyl)piperazine-1-sulfonyl]phenyl}-1-propyl-2,3,6,7-tetrahydro-1H-purine-2,6-dione (Nakatsukasa et al, 2011)); and the A3 receptor antagonist may be MRS3777 (2-Phenoxy-6-(cyclohexylamino)purine hemioxalate).

In certain embodiments, the small molecule inhibitor of the indoleamine-2,3-dioxygenase pathway may be Indoximod (NSC-721782/NLG-9189 (1-Methyl-D-tryptophan), NewLink Genetics), INCB024360 ((4E)-4-[(3-chloro-4-fluoroanilino)-nitrosomethylidene]-1,2,5-oxadiazol-3-amine, Incyte) or NLG-919 (1-Cyclohexyl-2-(5H-imidazo [5,1-a]isoindol-5-yl)ethanol), NewLink Genetics).

The HIF-1 regulator may be M30, (5-[N-methyl-N-propargylaminomethyl]-8-hydroxyquinoline) described in Zheng et al. (Zheng et al, 2015).

In certain embodiments, the agent can be derived from a broad spectrum of antibiotics which targets gram-positive and gram-negative bacteria, and thereby facilitating immunomodulation of Tregs, e.g. vancomycin which targets gram-positive bacteria and has been shown to reduce Treg levels/activity (Brestoff & Artis, 2013; Smith et al, 2013).

As stated above, the active agent is administered by a dosage regime comprising at least two courses of therapy, each course of therapy comprising in sequence a treatment session followed by an interval session. The dosage regime may be determined in a number of ways. For example, the level of immunosuppression may be calibrated to a desired level for each patient who is being treated (personalized medicine), by monitoring the level or activity of IFN-γ-producing leukocytes or proliferation rate of leukocytes in response to stimulation individually, and adjusting the treatment session, the frequency of administration and the interval session empirically and personally as determined from the results of the monitoring.

Thus, the treatment session may comprise administering the active agent or pharmaceutical composition to the individual and the treatment session is maintained at least until the systemic presence or level of IFN-γ-producing leukocytes, or the rate of proliferation of leukocytes in response to stimulation rises above a reference, the administering is paused during the interval session, and the interval session is maintained as long as the level is above the reference, wherein the reference is selected from (a) the level of systemic presence or activity of IFN-γ-producing leukocytes, or the rate of proliferation of leukocytes in response to stimulation, measured in the most recent blood sample obtained from said individual before said administering; or (b) the level of systemic presence or activity of IFN-γ-producing leukocytes, or the rate of proliferation of leukocytes in response to stimulation, characteristic of a population of individuals afflicted with a disease, disorder, condition or injury of the CNS.

The length of the treatment and interval sessions may be determined by physicians in clinical trials directed to a certain patient population and then applied consistently to this patient population, without the need for monitoring the level of immunosuppression on a personal basis.

In certain embodiments, the treatment session comprises administering the active agent to the individual and the treatment session is maintained at least until the systemic presence of the active agent reaches therapeutic levels, the administering is paused during the interval session, and the interval session is maintained as long as the level is above about 95%, 90%, 80%, 70%, 60% or 50% of said therapeutic level. The term "therapeutic level" as used herein refers to generally accepted systemic levels of drugs used to block immune checkpoints in known therapies, such as cancer therapy (see above).

In certain embodiments, the treatment session may be between 3 days and four weeks long, for example between one and four weeks long.

In certain embodiments, the interval session may be between one week and six months, for example between two weeks and six months long, in particular between 3 weeks and six months long.

In the treatments session, the administration of the active agent or pharmaceutical composition may be repeated administration, for example the active agent or pharmaceutical composition may be administered daily, or once every two, three, four, five or six days, once weekly, once every two weeks, once every three weeks or once every four weeks. These frequencies are applicable to any active agent, may be based on commonly used practices in the art, and may finally be determined by physicians in clinical trials. Alternatively, the frequency of the repeated administration in the treatment session could be adapted according to the nature of the active agent, wherein for example, a small molecule may be administered daily and an antibody may be administered once every 3 days. It should be understood that when an agent is administered during a treatment session at a relatively low frequency, for example once per week during a treatment session of one month, or once per month during a treatment session of six months, this treatment session is followed by a non-treatment interval session, the length of which is longer than the period between the repeated administrations during the treatment session (i.e. longer than one week or one month, respectively, in this example). The pause of one week or one month between the administrations during the treatment session in this example is not considered an interval session.

The lengths of the treatment session and the interval session may be adjusted to the frequency of the administration such that, for example, a frequency of administering the active agent once every 3 days may result in a treatment session of 6 or 9 days and an interval session that is commenced accordingly.

In any case, the dosage regimen, i.e. the length of the treatment session and the interval session, is calibrated such that the reduction in the level of immunosuppression, for example as measured by a reduction in the level of systemic presence or activity of regulatory T cells or the increase in the level of systemic presence or activity of IFN-γ producing leukocytes in the individual, is transient.

The method, active agent or pharmaceutical composition according to the present invention may be for treating a disease, disorder or condition of the CNS that is a neurodegenerative disease, disorder or condition selected from Alzheimer's disease, amyotrophic lateral sclerosis, Parkinson's disease Huntington's disease, primary progressive multiple sclerosis; secondary progressive multiple sclerosis, corticobasal degeneration, Rett syndrome, a retinal degeneration disorder selected from the group consisting of age-related macular degeneration and retinitis pigmentosa; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia or progressive supranuclear palsy. In certain embodiments, the condition of the CNS is aged-related dementia.

In certain embodiments, the condition of the CNS is Alzheimer's disease, amyotrophic lateral sclerosis, Parkinson's disease Huntington's disease.

The method, active agent and pharmaceutical composition according to the present invention may further be for treating an injury of the CNS selected from spinal cord injury, closed head injury, blunt trauma, penetrating trauma, hemorrhagic stroke, ischemic stroke, cerebral ischemia, optic nerve injury, myocardial infarction, organophosphate poisoning and injury caused by tumor excision As stated above, the inventors have found that the present invention improves the cognitive function in mice that emulates Alzheimer's disease. Thus, the method, active agent and pharmaceutical composition may be for use in improving CNS motor and/or cognitive function, for example for use in alleviating age-associated loss of cognitive function, which may occur in individuals free of a diagnosed disease, as well as in people suffering from neurodegenerative disease. Furthermore, the method, active agent and pharmaceutical composition may be for use in alleviating loss of cognitive function resulting from acute stress or traumatic episode. The cognitive function mentioned herein above may comprise learning, memory or both.

The term "CNS function" as used herein refers, inter alia, to receiving and processing sensory information, thinking, learning, memorizing, perceiving, producing and understanding language, controlling motor function and auditory and visual responses, maintaining balance and equilibrium, movement coordination, the conduction of sensory information and controlling such autonomic functions as breathing, heart rate, and digestion.

The terms "cognition", "cognitive function" and "cognitive performance" are used herein interchangeably and are related to any mental process or state that involves but is not limited to learning, memory, creation of imagery, thinking, awareness, reasoning, spatial ability, speech and language skills, language acquisition and capacity for judgment attention. Cognition is formed in multiple areas of the brain such as hippocampus, cortex and other brain structures. However, it is assumed that long term memories are stored at least in part in the cortex and it is known that sensory information is acquired, consolidated and retrieved by a specific cortical structure, the gustatory cortex, which resides within the insular cortex.

In humans, cognitive function may be measured by any know method, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). Cognitive function may also be measured indirectly using imaging techniques such as Positron Emission Tomography (PET), functional magnetic resonance imaging (fMRI), Single Photon Emission Computed Tomography (SPECT), or any other imaging technique that allows one to measure brain function.

An improvement of one or more of the processes affecting the cognition in a patient will signify an improvement of the cognitive function in said patient, thus in certain embodiments improving cognition comprises improving learning, plasticity, and/or long term memory. The terms "improving" and "enhancing" may be used interchangeably.

The term "learning" relates to acquiring or gaining new, or modifying and reinforcing, existing knowledge, behaviors, skills, values, or preferences.

The term "plasticity" relates to synaptic plasticity, brain plasticity or neuroplasticity associated with the ability of the brain to change with learning, and to change the already acquired memory. One measurable parameter reflecting plasticity is memory extinction.

The term "memory" relates to the process in which information is encoded, stored, and retrieved. Memory has three distinguishable categories: sensory memory, short-term memory, and long-term memory.

The term "long term memory" is the ability to keep information for a long or unlimited period of time. Long term memory comprises two major divisions: explicit memory (declarative memory) and implicit memory (non-declarative memory). Long term memory is achieved by memory consolidation which is a category of processes that stabilize a memory trace after its initial acquisition. Consolidation is distinguished into two specific processes, synaptic consolidation, which occurs within the first few hours after learning, and system consolidation, where hippocampus-dependent memories become independent of the hippocampus over a period of weeks to years.

The embodiments above that describe different features of the pharmaceutical composition of the present invention are relevant also for the method of the invention, because the method employs the same pharmaceutical composition.

In yet another aspect, the present invention provides methods for reducing Aβ-plaque burden in a patient diagnosed with Alzheimer's disease, comprising administering to said patient an active agent or pharmaceutical composition as defined herein above that causes reduction of the level of systemic immunosuppression by release of a restraint imposed on the immune system by one or more immune checkpoints.

In still another aspect, the present invention provides a method for reducing hippocampal gliosis in a patient diagnosed with Alzheimer's disease, comprising administering to said patient an active agent or pharmaceutical composition as defined herein above that causes reduction of the level of systemic immunosuppression by release of a restraint imposed on the immune system by one or more immune checkpoints.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The determination of the doses of the active ingredient to be used for human use is based on commonly used practices in the art, and will be finally determined by physicians in clinical trials. An expected approximate equivalent dose for administration to a human can be calculated based on the in vivo experimental evidence disclosed herein below, using known formulas (e.g. Reagan-Show et al. (2007) Dose translation from animal to human studies revisited. The FASEB Journal 22:659-661). According to this paradigm, the adult human equivalent dose (mg/kg body weight) equals a dose given to a mouse (mg/kg body weight) multiplied with 0.081.

The invention will now be illustrated by the following non-limiting examples.

EXAMPLES

Materials and Methods

Animals.

5XFAD transgenic mice (Tg6799) that co-overexpress familial AD mutant forms of human APP (the Swedish mutation, K670N/M671L; the Florida mutation, 1716V; and the London mutation, V717I) and PS1 (M146L/L286V) transgenes under transcriptional control of the neuron-specific mouse Thy-1 promoter (Oakley et al, 2006), and AD double transgenic B6.Cg-Tg (APPswe, PSEN1dE9) 85Dbo/J mice (Borchelt et al, 1997) were purchased from The Jackson Laboratory. Genotyping was performed by PCR analysis of tail DNA, as previously described (Oakley et al, 2006). Heterozygous mutant $cx_3cr1^{GFP/+}$ mice (Jung et al, 2000) (B6.129P-cx3cr1$^{tm1Litt}$/J, in which one of the $CX_3CR1$ chemokine receptor alleles was replaced with a gene encoding GFP) were used as donors for BM chimeras. Foxp3.LuciDTR mice (Suffner et al, 2010) were bred with 5XFAD mice to enable conditional depletion of Foxp3$^+$ Tregs. Animals were bred and maintained by the Animal Breeding Center of the Weizmann Institute of Science. All experiments detailed herein complied with the regulations formulated by the Institutional Animal Care and Use Committee (IACUC) of the Weizmann Institute of Science.

RNA Purification, cDNA Synthesis, and Quantitative Real-Time PCR Analysis.

Total RNA of the hippocampal dentate gyrus (DG) was extracted with TTI Reagent (Molecular Research Center) and purified from the lysates using an RNeasy Kit (Qiagen). Total RNA of the choroid plexus was extracted using an RNA MicroPrep Kit (Zymo Research). mRNA (1 µg) was converted into cDNA using a High Capacity cDNA Reverse Transcription Kit (Applied Biosystems). The expression of specific mRNAs was assayed using fluorescence-based quantitative real-time PCR (RT-qPCR). RT-qPCR reactions were performed using Fast-SYBR PCR Master Mix (Applied Biosystems). Quantification reactions were performed in triplicate for each sample using the standard curve method. Peptidylprolyl isomerase A (ppia) was chosen as a reference (housekeeping) gene. The amplification cycles were 95° C. for 5 s, 60° C. for 20 s, and 72° C. for 15 s. At the end of the assay, a melting curve was constructed to evaluate the specificity of the reaction. For ifn-y and ppia gene analysis, the cDNA was pre-amplified in 14 PCR cycles with non-random PCR primers, thereby increasing the sensitivity of the subsequent real-time PCR analysis, according to the manufacturer's protocol (PreAmp Master Mix Kit; Applied Biosystems). mRNA expression was determined using TaqMan RT-qPCR, according to the manufacturer's instructions (Applied Biosystems). All RT-qPCR reactions were performed and analyzed using StepOne software V2.2.2 (Applied Biosystems). The following TaqMan Assays-on-Demand™ probes were used: Mm02342430_g1 (ppia) and Mm01168134_m1 (ifn-γ). For all other genes examined, the following primers were used:

```
ppia forward
                                   (SEQ ID NO: 33)
5'-AGCATACAGGTCCTGGCATCTTGT-3'
and reverse 5'-
                                   (SEQ ID NO: 34)
CAAAGACCACATGCTTGCCATCCA-3';

icam1 forward
                                   (SEQ ID NO: 35)
5'-AGATCACATTCACGGTGCTGGCTA-3'
and reverse 5'-
                                   (SEQ ID NO: 36)
AGCTTTGGGATGGTAGCTGGAAGA-3';

vcam1 forward
                                   (SEQ ID NO: 37)
5'-TGTGAAGGGATTAACGAGGCTGGA-3'
and reverse 5'-
                                   (SEQ ID NO: 38)
CCATGTTTCGGGCACATTTCCACA-3';

cxcl10 forward
                                   (SEQ ID NO: 39)
5'-AACTGCATCCATATCGATGAC-3'
and reverse 5'-
                                   (SEQ ID NO: 40)
GTGGCAATGATCTCAACAC-3';

ccl2 forward
                                   (SEQ ID NO: 41)
5'-CATCCACGTGTTGGCTCA-3'
and reverse 5'-
                                   (SEQ ID NO: 42)
GATCATCTTGCTGGTGAATGAGT-3';

tnf-γ forward
                                   (SEQ ID NO: 43)
5'-GCCTCTTCTCATTCCTGCTT-3'
reverse
                                   (SEQ ID NO: 44)
CTCCTCCACTTGGTGGTTTG-3';

il-1β forward
                                   (SEQ ID NO: 45)
5'-CCAAAAGATGAAGGGCTGCTT-3'
and reverse 5'-
                                   (SEQ ID NO: 46)
TGCTGCTGCGAGATTTGAAG-3';

il-12p40 forward
                                   (SEQ ID NO: 47)
5'-GAAGTTCAACATCAAGAGCA-3'
and reverse 5'-
                                   (SEQ ID NO: 48)
CATAGTCCCTTTGGTCCAG-3';

il-10 forward
                                   (SEQ ID NO: 49)
5'-TGAATTCCCTGGGTGAGAAGCTGA-3'
and reverse 5'-
                                   (SEQ ID NO: 50)
TGGCCTTGTAGACACCTTGGTCTT-3';

tgfβ2 forward
                                   (SEQ ID NO: 51)
5'-AATTGCTGCCTTCGCCCTCTTTAC-3'
and reverse 5'-
                                   (SEQ ID NO: 52)
TGTACAGGCTGAGGACTTTGGTGT-3';

igf-1 forward
                                   (SEQ ID NO: 53)
5'-CCGGACCAGAGACCCTTTG
and reverse 5'-
                                   (SEQ ID NO: 54)
CCTGTGGGCTTGTTGAAGTAAAA-3';

bdnf forward
                                   (SEQ ID NO: 55)
5'-GATGCTCAGCAGTCAAGTGCCTTT-3'
and reverse 5'-
                                   (SEQ ID NO: 56)
GACATGTTTGCGGCATCCAGGTAA-3';
```

Immunohistochemistry.

Tissue processing and immunohistochemistry were performed on paraffin embedded sectioned mouse (6 μm thick) and human (10 μm thick) brains. For human ICAM-1 staining, primary mouse anti-ICAM (1:20 Abcam; ab2213) antibody was used. Slides were incubated for 10 min with 3% H2O2, and a secondary biotin-conjugated anti-mouse antibody was used, followed by biotin/avidin amplification with Vectastain ABC kit (Vector Laboratories). Subsequently, 3,3'-diaminobenzidine (DAB substrate) (Zytomed kit) was applied; slides were dehydrated and mounted with xylene-based mounting solution. For tissue stainings, mice were transcardially perfused with PBS prior to tissue excision and fixation. CP tissues were isolated under a dissecting microscope (Stemi DV4; Zeiss) from the lateral, third, and fourth ventricles of the brain. For whole mount CP staining, tissues were fixated with 2.5% paraformaldehyde (PFA) for 1 hour at 4° C., and subsequently transferred to PBS containing 0.05% sodium azide. Prior to staining, the dissected tissues were washed with PBS and blocked (20% horse serum, 0.3% Triton X-100, and PBS) for 1 h at room temperature. Whole mount staining with primary antibodies (in PBS containing 2% horse serum and 0.3% Triton X-100), or secondary antibodies, was performed for 1 h at room temperature. Each step was followed by three washes in PBS. The tissues were applied to slides, mounted with Immu-mount (9990402, from Thermo Scientific), and sealed with cover-slips. For staining of sectioned brains, two different tissue preparation protocols (paraffin embedded or microtomed free-floating sections) were applied, as previously described (Baruch et al, 2013; Kunis et al, 2013). The following primary antibodies were used: mouse anti-Aβ (1:300, Covance, #SIG-39320); rabbit anti-GFP (1:100, MBL, #598); rat anti-CD68 (1:300, eBioscience, #14-0681); rat anti-ICAM-1 (1:200, Abcam, #AB2213); goat anti-GFP (1:100, Abcam, #ab6658); rabbit anti-IBA-1 (1:300, Wako,

019-19741); goat anti-IL-10 (1:20, R&D systems, #AF519); rat anti-Foxp3 (1:20, eBioscience, #13-5773-80); rabbit anti-CD3 (1:500, Dako, #IS503); mouse anti-ZO-1, mouse anti-E-Cahedrin, and rabbit anti-Claudin-1 (all 1:100, Invitrogen, #33-9100, #33-4000, #51-9000); rabbit anti-GFAP (1:200, Dako, #Z0334). Secondary antibodies included: Cy2/Cy3/Cy5-conjugated donkey anti-mouse/goat/rabbit/rat antibodies (1:200; all from Jackson Immunoresearch). The slides were exposed to Hoechst nuclear staining (1:4000; Invitrogen Probes) for 1 min. Two negative controls were routinely used in immunostaining procedures, staining with isotype control antibody followed by secondary antibody, or staining with secondary antibody alone. For Foxp3 intracellular staining, antigen retrieval from paraffin-embedded slides was performed using Retreivagen Kit (#550524, #550527; BD Pharmingen™) Microscopic analysis, was performed using a fluorescence microscope (E800; Nikon) or laser-scanning confocal microscope (Carl Zeiss, Inc.). The fluorescence microscope was equipped with a digital camera (DXM 1200F; Nikon), and with either a 20×NA 0.50 or 40×NA 0.75 objective lens (Plan Fluor; Nikon). The confocal microscope was equipped with LSM 510 laser scanning capacity (three lasers: Ar 488, HeNe 543, and HeNe 633). Recordings were made on postfixed tissues using acquisition software (NIS-Elements, F3 [Nikon] or LSM [Carl Zeiss, Inc.]). For quantification of staining intensity, total cell and background staining was measured using ImageJ software (NIH), and intensity of specific staining was calculated, as previously described (Burgess et al, 2010). Images were cropped, merged, and optimized using Photoshop CS6 13.0 (Adobe), and were arranged using Illustrator CS5 15.1 (Adobe).

Paraffin Embedded Sections of Human CP.

Human brain sections of young and aged postmortem non-CNS-disease individuals, as well as AD patients, were obtained from the Oxford Brain Bank (formerly known as the Thomas Willis Oxford Brain Collection (TWOBC)) with appropriate consent and Ethics Committee approval (TW220). The experiments involving these sections were approved by the Weizmann Institute of Science Bioethics Committee.

Flow Cytometry, Sample Preparation and Analysis.

Mice were transcardially perfused with PBS, and tissues were treated as previously described (Baruch et al, 2013). Brains were dissected and the different brain regions were removed under a dissecting microscope (Stemi DV4; Zeiss) in PBS, and tissues were dissociated using the gentleMACS™ dissociator (Miltenyi Biotec). Choroid plexus tissues were isolated from the lateral, third and fourth ventricles of the brain, incubated at 37° C. for 45 min in PBS (with $Ca^{2+}/Mg^{2+}$) containing 400 U/ml collagenase type IV (Worthington Biochemical Corporation), and then manually homogenized by pipetting. Spleens were mashed with the plunger of a syringe and treated with ACK (ammonium chloride potassium) lysing buffer to remove erythrocytes. In all cases, samples were stained according to the manufacturers' protocols. All samples were filtered through a 70 μm nylon mesh, and blocked with anti-Fc CD16/32 (1:100; BD Biosciences). For intracellular staining of IFN-γ, the cells were incubated with para-methoxyamphetamine (10 ng/ml; Sigma-Aldrich) and ionomycin (250 ng/ml; Sigma-Aldrich) for 6 h, and Brefeldin-A (10 μg/ml; Sigma-Aldrich) was added for the last 4 h. Intracellular labeling of cytokines was done with BD Cytofix/Cytoperm™ Plus fixation/permeabilization kit (cat. no. 555028). For Treg staining, an eBioscience FoxP3 staining buffer set (cat. no. 00-5523-00) was used. The following fluorochrome-labeled monoclonal antibodies were purchased from BD Pharmingen, BioLegend, R&D Systems, or eBiosciences, and used according to the manufacturers' protocols: PE or Alexa Fluor 450-conjugated anti-CD4; PE-conjugated anti-CD25; PerCP-Cy5.5-conjugated anti-CD45; FITC-conjugated anti-TCRβ; APC-conjugated anti-IFN-γ; APC-conjugated anti-FoxP3; Brilliant-violet-conjugated anti-CD45. Cells were analyzed on an LSRII cytometer (BD Biosciences) using FlowJo software. In each experiment, relevant negative control groups, positive controls, and single stained samples for each tissue were used to identify the populations of interest and to exclude other populations.

Preparation of BM Chimeras.

BM chimeras were prepared as previously described (Shechter et al, 2009; Shechter et al, 2013). In brief, gender-matched recipient mice were subjected to lethal whole-body irradiation (950 rad) while shielding the head (Shechter et al, 2009). The mice were then injected intravenously with $5×10^6$ BM cells from $CX_3CR1^{GFP/+}$ donors. Mice were left for 8-10 weeks after BM transplantation to enable reconstitution of the hematopoietic lineage, prior to their use in experiments. The percentage of chimerism was determined by FACS analysis of blood samples according to percentages of GFP expressing cells out of circulating monocytes ($CD11b^+$). In this head-shielded model, an average of 60% chimerism was achieved, and CNS-infiltrating $GFP^+$ myeloid cells were verified to be $CD45^{high}/CD11b^{high}$, representing monocyte-derived macrophages and not microglia (Shechter et al, 2013).

Morris Water Maze.

Mice were given three trials per day, for 4 consecutive days, to learn to find a hidden platform located 1.5 cm below the water surface in a pool (1.1 m in diameter). The water temperature was kept between 21-22° C. Water was made opaque with milk powder. Within the testing room, only distal visual shape and object cues were available to the mice to aid in location of the submerged platform. The escape latency, i.e., the time required to find and climb onto the platform, was recorded for up to 60 s. Each mouse was allowed to remain on the platform for 15 s and was then removed from the maze to its home cage. If the mouse did not find the platform within 60 s, it was manually placed on the platform and returned to its home cage after 15 s. The inter-trial interval for each mouse was 10 min. On day 5, the platform was removed, and mice were given a single trial lasting 60 s without available escape. On days 6 and 7, the platform was placed in the quadrant opposite the original training quadrant, and the mouse was retrained for three sessions each day. Data were recorded using the EthoVision V7.1 automated tracking system (Noldus Information Technology). Statistical analysis was performed using analysis of variance (ANOVA) and the Bonferroni post-hoc test. All MWM testing was performed between 10 a.m. and 5 p.m. during the lights-off phase.

Radial Arm Water Maze.

The radial-arm water maze (RAWM) was used to test spatial learning and memory, as was previously described in detail (Alamed et al, 2006). Briefly, six stainless steel inserts were placed in the tank, forming six swim arms radiating from an open central area. The escape platform was located at the end of one arm (the goal arm), 1.5 cm below the water surface, in a pool 1.1 m in diameter. The water temperature was kept between 21-22° C. Water was made opaque with milk powder. Within the testing room, only distal visual shape and object cues were available to the mice to aid in location of the submerged platform. The goal arm location remained constant for a given mouse. On day 1, mice were trained for 15 trials (spaced over 3 h), with trials alternating between a visible and hidden platform, and the last 4 trials with hidden platform only. On day 2, mice were trained for 15 trials with the hidden platform. Entry into an incorrect arm, or failure to select an arm within 15 sec, was scored as an error. Spatial learning and memory were measured by counting the number of arm entry errors or the escape latency of the mice on each trial. Training data were analyzed as the mean errors or escape latency, for training blocks of three consecutive trials.

GA Administration.

Each mouse was subcutaneously (s.c.) injected with a total dose of 100 μg of GA (batch no. P53640; Teva Pharmaceutical Industries, Petah Tiqva, Israel) dissolved in 200 μl of PBS. Mice were either injected according to a weekly-GA regimen (Butovsky et al, 2006), or daily-GA administration (FIG. 8 and FIG. 16). Mice were euthanized either 1 week after the last GA injection, or 1 month after treatment, as indicated for each experiment.

Conditional Ablation of Treg.

Figure 4:
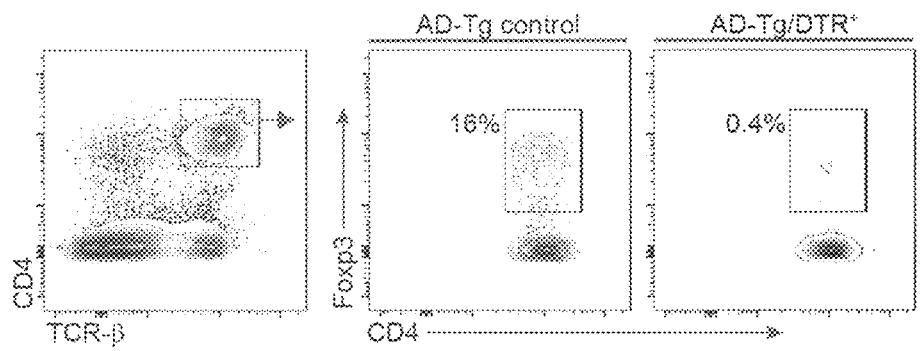
FIG. 4 shows gating strategy and representative flow cytometry plots of splenocytes from AD-Tg/Foxp3-DTR$^{+/-}$ mice, 1 day after the last injection of DTx. DTx was injected i.p. for 4 constitutive days, achieving ~99% depletion of Foxp3$^+$ cells.

Diphtheria toxin (DTx; 8 ng/g body weight; Sigma) was injected intraperitoneally (i.p.) daily for 4 consecutive days to Foxp3.LuciDTR mice (Suffner et al, 2010). The efficiency of DTx was confirmed by flow cytometry analysis of immune cells in the blood and spleen, achieving almost complete (>99%) depletion of the GFP-expressing FoxP3$^-$ CD4$^+$ Treg cells (FIG. 4).

P300 Inhibition.

Inhibition of p300 in mice was performed similarly to previously described (Liu et al, 2013). p300i (C646; Tocris Bioscience) was dissolved in DMSO and injected i.p. daily (8.9 mg kg$^{-1}$ d$^{-1}$, i.p.) for 1 week. Vehicle-treated mice were similarly injected with DMSO.

Atra Treatment.

All-trans retinoic acid (ATRA) administration to mice was performed similarly to previously described (Walsh et al, 2014). ATRA (Sigma) was dissolved in DMSO and injected i.p. (8 mg kg$^{-1}$ d$^{-1}$) every other day over the course of 1 week. Vehicle-treated mice were similarly injected with DMSO.

Soluble Aβ (sAβ) Protein Isolation and Quantification.

Tissue homogenization and sAβ protein extraction was performed as previously described (Schmidt et al, 2005). Briefly, cerebral brain parenchyma was dissected and snap-frozen and kept at −80° C. until homogenization. Proteins were sequentially extracted from samples to obtain separate fractions containing proteins of differing solubility. Samples were homogenized in 10 volumes of ice-cold tissue homogenization buffer, containing 250 mM of sucrose, 20 mM of Tris base, 1 mM of ethylenediaminetetraacetic acid (EDTA), and 1 mM of ethylene glycol tetraacetic acid (pH 7.4), using a ground glass pestle in a Dounce homogenizer. After six strokes, the homogenate was mixed 1:1 with 0.4% diethylamine (DEA) in a 100-mM NaCl solution before an additional six strokes, and then centrifuged at 135,000 g at 4° C. for 45 min. The supernatant (DEA-soluble fraction containing extracellular and cytosolic proteins) was collected and neutralized with 10% of 0.5 Mof Tris-HCl (pH 6.8). Aβ$_{1-40}$ and Aβ$_{1-42}$ were individually measured by enzyme-linked immunosorbent assay (ELISA) from the soluble fraction using commercially available kits (Biolegend; #SIG-38954 and #SIG-38956, respectively) according to the manufacturer instructions.

Aβ Plaque Quantitation.

From each brain, 6 μm coronal slices were collected, and eight sections per mouse, from four different pre-determined depths throughout the region of interest (dentate gyrus or cerebral cortex) were immunostained. Histogram-based segmentation of positively stained pixels was performed using the Image-Pro Plus software (Media Cybernetics, Bethesda, Md., USA). The segmentation algorithm was manually applied to each image, in the dentate gyms area or in the cortical layer V, and the percentage of the area occupied by total Aβ immunostaining was determined. Plaque numbers were quantified from the same 6 μm coronal brain slices, and are presented as average number of plaques per brain region. Prior to quantification, slices were coded to mask the identity of the experimental groups, and plaque burden was quantified by an observer blinded to the identity of the groups.

Statistical Analysis.

The specific tests used to analyze each set of experiments are indicated in the figure legends. Data were analyzed using a two-tailed Student's t test to compare between two groups, one-way ANOVA was used to compare several groups, followed by the Newman-Keuls post-hoc procedure for pairwise comparison of groups after the null hypothesis was rejected (P<0.05). Data from behavioral tests were analyzed using two-way repeated-measures ANOVA, and Bonferroni post-hoc procedure was used for follow-up pairwise comparison. Sample sizes were chosen with adequate statistical power based on the literature and past experience, and mice were allocated to experimental groups according to age, gender, and genotype. Investigators were blinded to the identity of the groups during experiments and outcome assessment. All inclusion and exclusion criteria were pre-established according to the IACUC guidelines. Results are presented as means±s.e.m. In the graphs, y-axis error bars represent s.e.m. Statistical calculations were performed using the GraphPad Prism software (GraphPad Software, San Diego, Calif.).

Figure 1B:
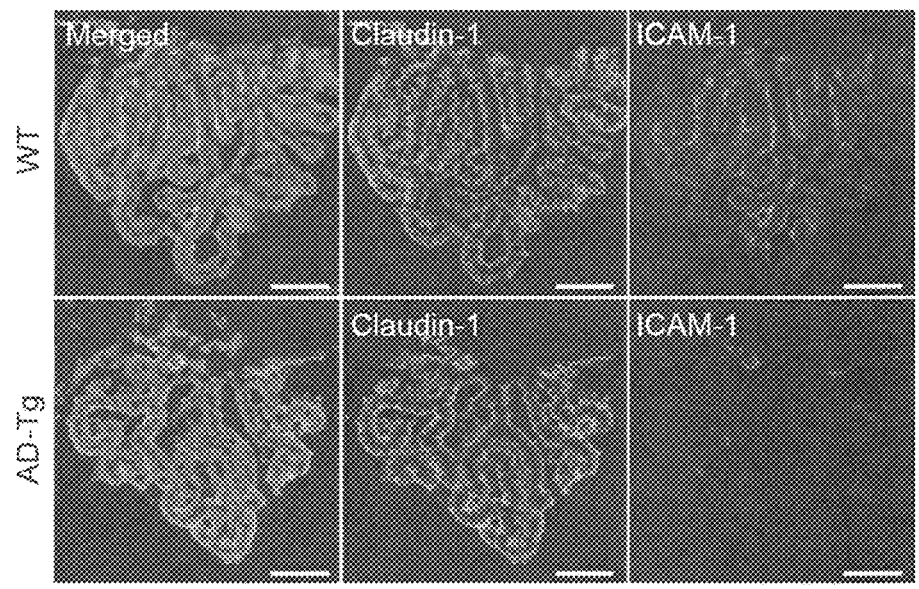
Figure 2A:
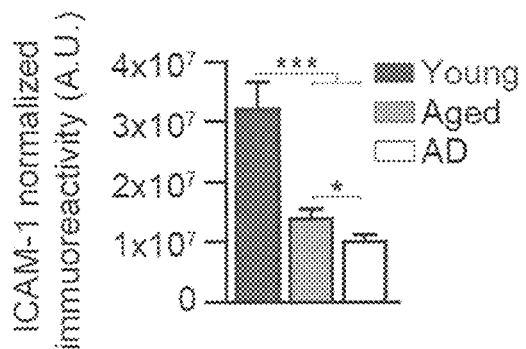
FIGS. 2A-C show (A) Quantification of ICAM-1 immunoreactivity in human postmortem CP of young and aged non-CNS diseased, and AD patients (n=5 per group; one-way ANOVA followed by Newman-Keuls post hoc analysis); (B) flow cytometry analysis for IFN-γ-expressing immune cells (intracellularly stained, and pre-gated on CD45) in CPs of 8-month old AD-Tg mice and age-matched WT controls. Shaded histogram represents isotype control (n=4-6 per group; Student's t test); and (C) mRNA expression levels of ifn-y, measured by RT-qPCR, in CP tissues isolated from 4- and 8-month old AD-Tg mice, compared to age-matched WT controls (n=5-8 per group; Student's t test for each time point). In all panels, error bars represent mean±s.e.m.; *, $P<0.05$; , $P<0.01$;*, $P<0.001$.
Figure 2B:
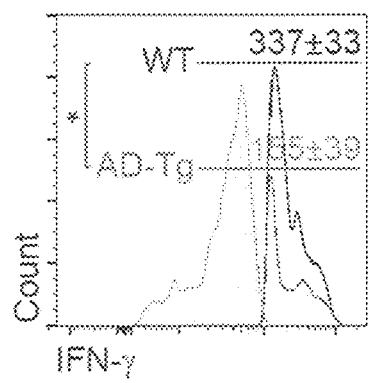
Figure 2C:
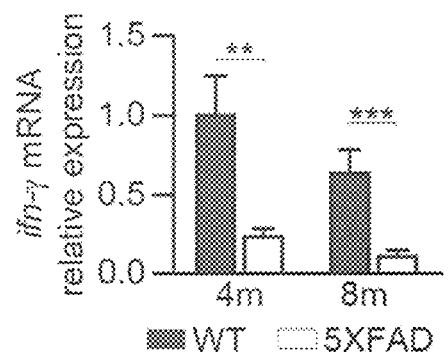

Example 1. Choroid Plexus (CP) Gateway Activity Along Disease Progression in the Mouse Model of AD We first examined CP activity along disease progression in the 5XFAD transgenic mouse model of AD (AD-Tg); these mice co-express five mutations associated with familial AD and develop cerebral Aβ pathology and gliosis as early as 2 months of age (Oakley et al, 2006). We found that along the progressive stages of disease pathology, the CP of AD-Tg mice, compared to age-matched wild-type (WT) controls, expressed significantly lower levels of leukocyte homing and trafficking determinants, including icam1, vcam1, cxcl10, and ccl2 (FIG. 1A), shown to be upregulated by the CP in response to acute CNS damage, and needed for transepithelial migration of leukocytes (Kunis et al, 2013; Shechter et al, 2013). Immunohistochemical staining for the integrin ligand, ICAM-1, confirmed its reduced expression by the CP epithelium of AD-Tg mice (FIG. 1b). In addition, staining for ICAM-1 in human postmortem brains, showed its age-associated reduction in the CP epithelium, in line with our previous observations (Baruch et al, 2014), and quantitative assessment of this effect revealed further decline in AD patients compared to aged individuals without CNS disease (FIG. 2A). Since the induction of leukocyte trafficking determinants by the CP is dependent on epithelial interferon (IFN)-γ signaling (Kunis et al, 2013), we next tested whether the observed effects could reflect loss of IFN-γ availability at the CP. Examining the CP of 5XFAD AD-Tg mice using flow cytometry intracellular staining, revealed significantly lower numbers of IFN-γ-producing cells in this compartment (FIG. 2B), and quantitative real-time PCR (RT-qPCR) analysis confirmed lower mRNA expression levels of ifn-y at the CP of AD-Tg mice compared to age-matched WT controls (FIG. 2C).

Figure 3A:
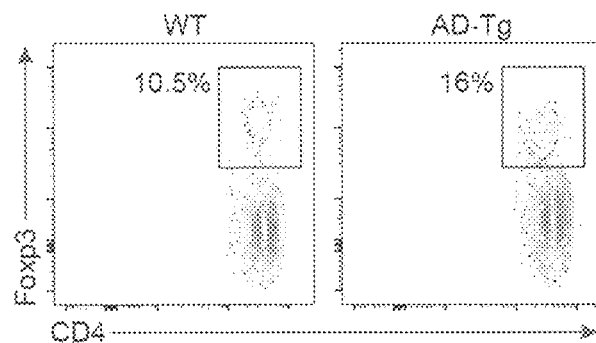
FIGS. 3A-B depict (A) representative flow cytometry plots of CD4$^+$Foxp3$^+$ splenocyte frequencies (pre-gated on TCRβ) in 8-month old AD-Tg and WT control mice; and (B) quantitative analysis of splenocytes from 1, 2, 4 and 8-month AD-Tg and WT control mice (n=6-8 per group; Student's t test for each time point). In all panels, error bars represent mean±s.e.m.; *, $P<0.05$; , $P<0.01$; *, $P<0.001$.
Figure 3B:
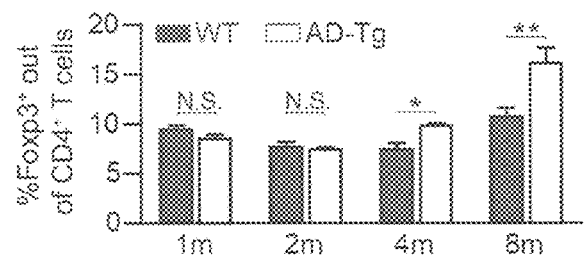
Figure 5A:
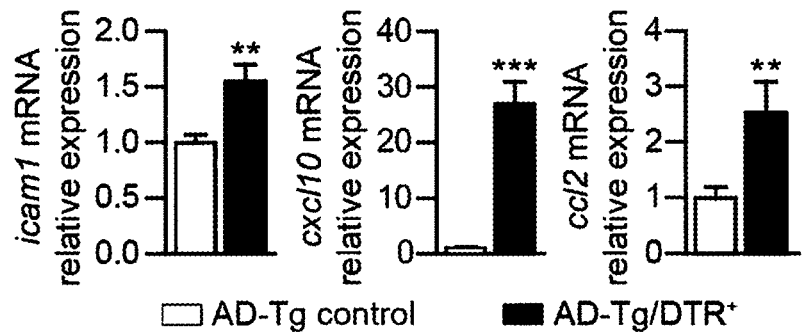
FIGS. 5A-G show the effects of transient depletion of Tregs in AD-Tg mice. (A) AD-Tg/Foxp3-DTR$^+$ (which express the DTR transgene) and a non-DTR-expressing AD-Tg littermate (AD-Tg/Foxp3-DTR$^-$) control group were treated with DTx for 4 constitutive days. CP mRNA expression levels for the genes icam1, cxcl10 and ccl2, measured by RT-qPCR, in 6-month old DTx-treated AD-Tg mice, 1 day after the last DTx injection (n=6-8 per group; Student's t test). (B-D) Flow cytometry analysis of the brain parenchyma (excluding the choroid plexus, which was separately excised) of 6-month old DTx-treated AD-Tg mice and controls, 3 weeks following the last DTx injection. Quantitative flow cytometry analysis showing increased numbers of CD11b$^{high}$/CD45$^{high}$ mo-MΦ and CD4$^+$ T cells (B), and representative flow cytometry plots (C) and quantitative analysis (D) of CD4$^+$Foxp3$^+$ Treg frequencies, in the brain parenchyma of AD-Tg/Foxp3-DTR$^+$ mice and AD-Tg/Foxp3-DTR$^-$ controls treated with DTx (n=3-7 per group; Student's t test). (E) mRNA expression levels of foxp3 and il10 in the brain parenchyma of 6-month old DTx-treated AD-Tg AD-Tg/Foxp3-DTR$^+$ and AD-Tg/Foxp3-DTR-contros, 3 weeks after the last DTx injection (n=6-8 per group; Student's t test). (F) quantitative analysis of GFAP immunostaining, showing reduced astrogliosis in hippocampal sections from 6-month old DTx-treated AD-Tg/Foxp3-DTR$^+$ and AD-Tg/Foxp3-DTR$^-$ control mice, 3 weeks following the last DTx injection (scale bar, 50 μm; n=3-5 per group; Student's t test). (G) mRNA expression levels of il-12p40 and tnf-a in the brain parenchyma, 3 weeks following the last DTx injection (n=6-8 per group; Student's t test). In all panels, error bars represent mean±s.e.m.; *, $P<0.05$; , $P<0.01$; *, $P<0.001$.
Figure 5B:
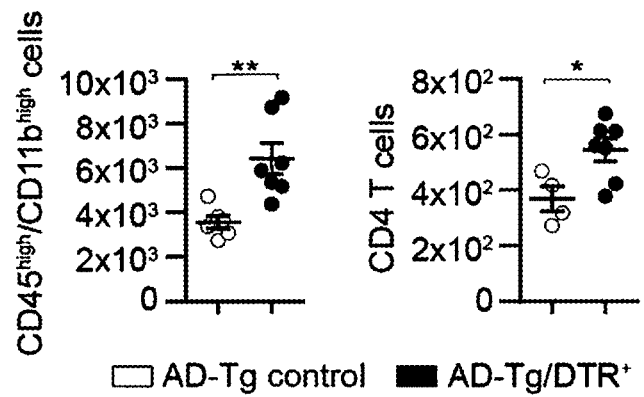
Figure 5C:
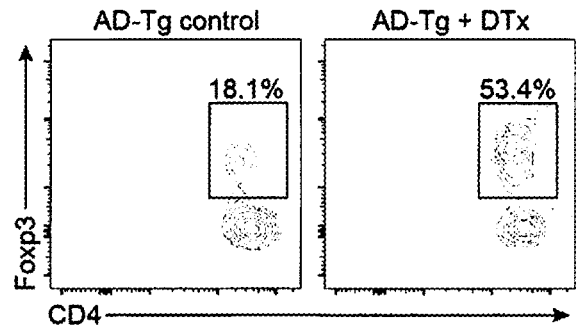
Figure 5D:
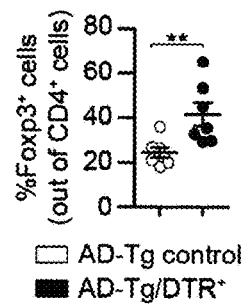
Figure 5E:
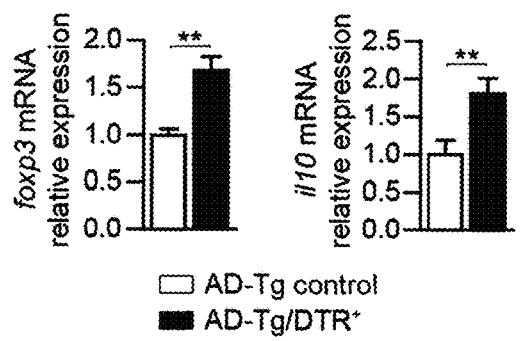

Example 2. The Functional Relationships Between Treg-Mediated Systemic Immune Suppression, CP Gateway Activity, and AD Pathology Regulatory T cells (Tregs) play a pivotal role in suppressing systemic effector immune responses (Sakaguchi et al, 2008). We envisioned that Treg-mediated systemic immune suppression affects IFN-γ availability at the CP, and therefore focused on the involvement of Tregs in AD pathology. In line with previous reports of elevated Treg levels and suppressive activities in AD patients (Rosenkranz et al, 2007; Saresella et al, 2010; Torres et al, 2013), evaluating Foxp3$^+$ Treg frequencies in splenocytes of 5XFAD AD-Tg mice, relative to their age-matched WT littermates, revealed their elevated levels along disease progression (FIG. 3A, B). To study the functional relationships between Treg-mediated systemic immune suppression, CP gateway activity, and AD pathology, we crossbred 5XFAD AD-Tg mice with Foxp3-diphtheria toxin receptor (DTR$^+$) mice, enabling transient conditional in vivo depletion of Foxp3$^-$ Tregs in AD-Tg/DTR$^+$ mice by administration of diphtheria toxin (DTx) (FIG. 4A). Transient depletion of Tregs resulted in elevated mRNA expression of leukocyte trafficking molecules by the CP of AD-Tg/DTR$^+$ mice relative to DTx-treated AD-Tg/DTR$^-$ littermates (FIG. 5A). Analysis of the long-term effect of the transient Treg depletion on the brain parenchyma (3 weeks later), revealed immune cell accumulation in the brain, including elevated numbers of CD45$^{high}$/CD11b$^{high}$ myeloid cells, representing infiltrating mo-MΦ (Shechter et al, 2013), and CD4$^+$ T cells (FIG. 5B). In addition, the short and transient depletion of Tregs resulted in a marked enrichment of Foxp3$^-$ Tregs among the CD4$^+$ T cells that accumulated within the brain, as assessed by flow cytometry (FIG. 5C, D). RT-qPCR analysis of the hippocampus showed increased expression of foxp3 and il10 mRNA (FIG. 5E).

Figure 5F:
Figure 5G:
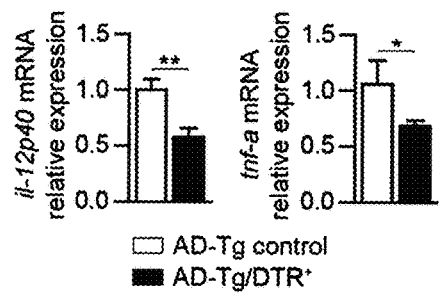
Figure 6A:
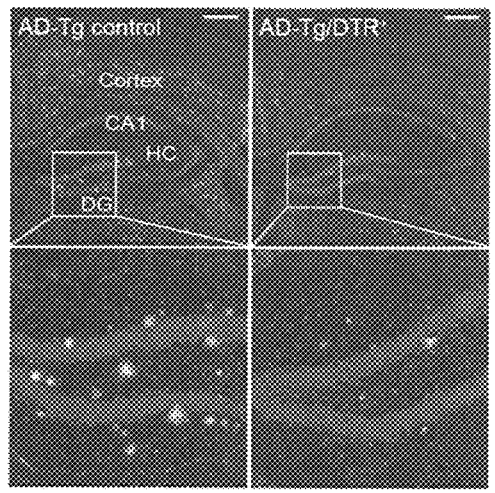
Figure 6B:
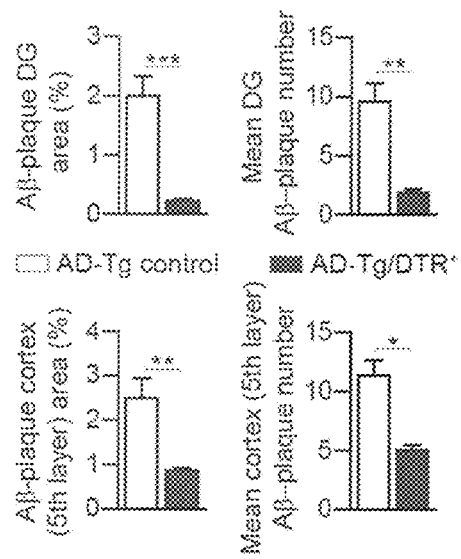
Figure 6C:
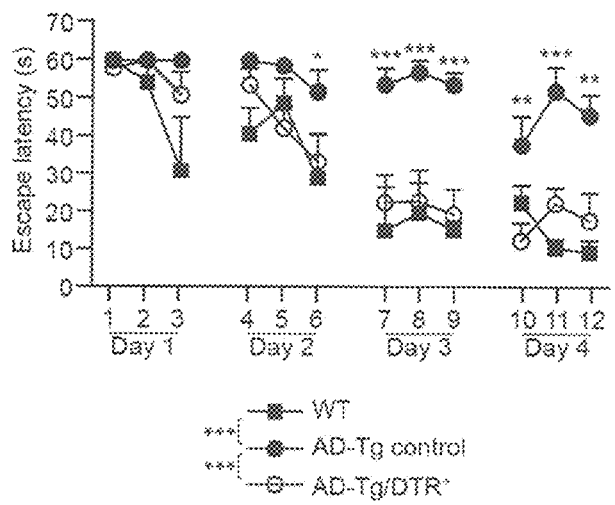
Figure 6D:
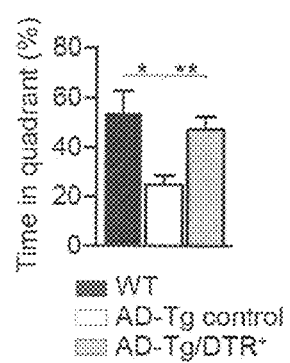
Figure 8B:
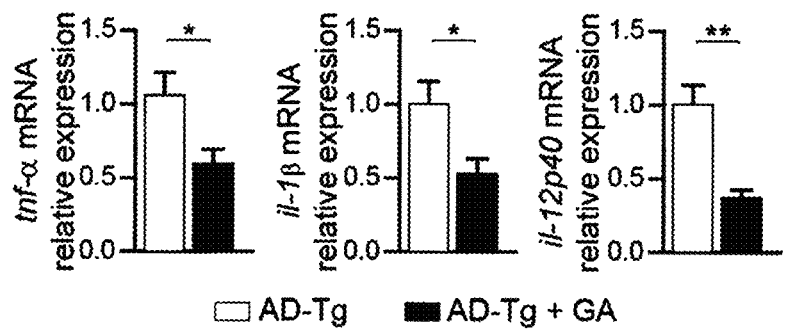
Figure 8C:
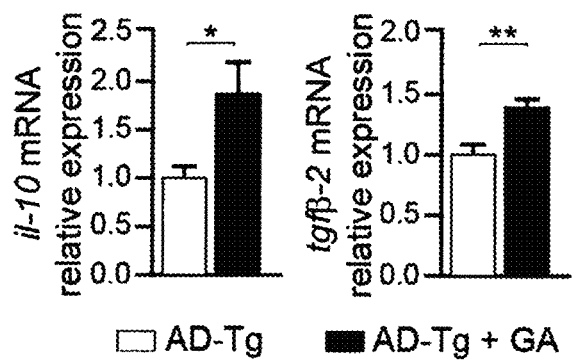
Figure 8D:
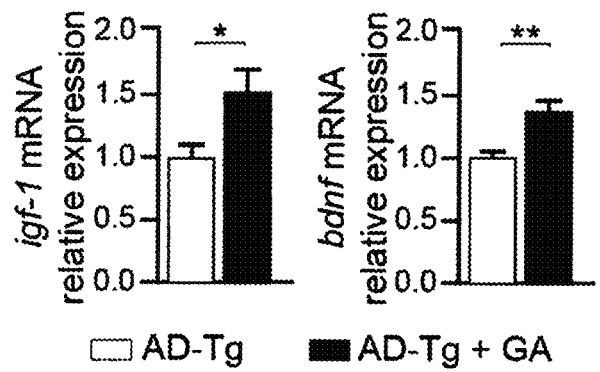
Figure 8E:
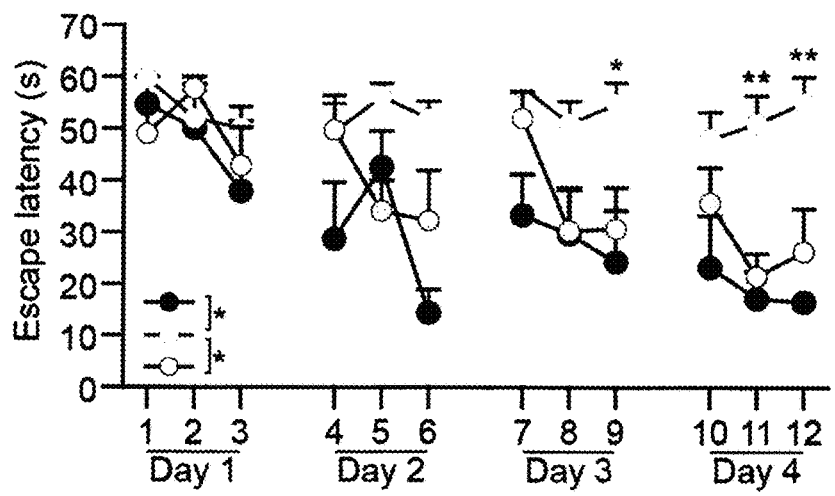
Figure 8F:
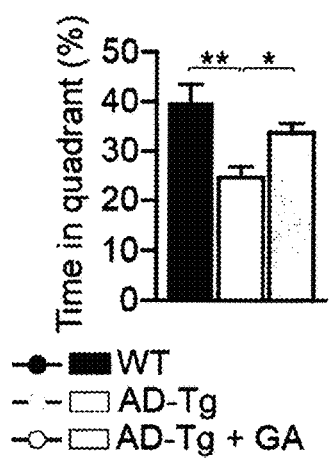
Figure 8G:
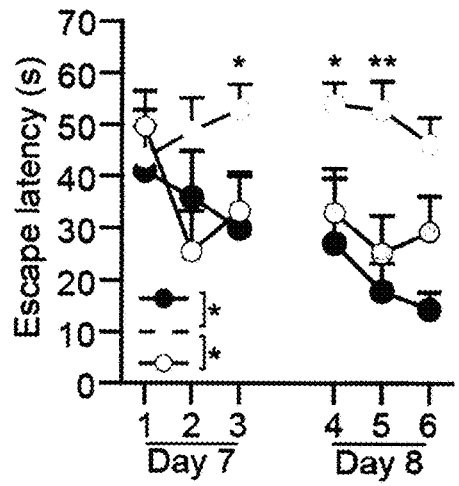
Figure 8H:
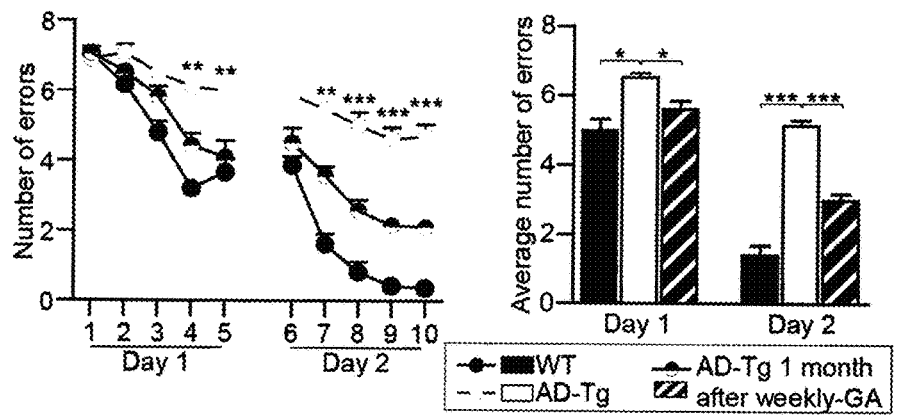
Figure 8I:
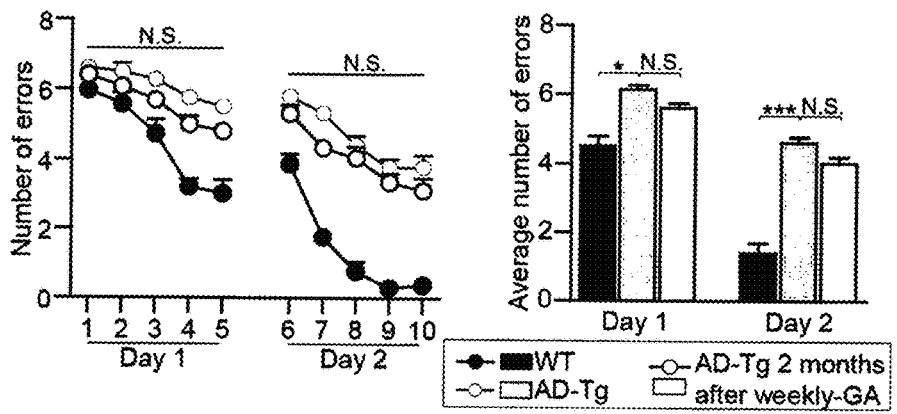

We next examined whether the short-term depletion of Tregs, which was followed by accumulation of immunoregulatory cells in sites of brain pathology, led to a long-term effect on brain function. We observed reduction in hippocampal gliosis (FIG. 5F), and reduced mRNA expression levels of pro-inflammatory cytokines, such as il-12p40 and tnf-α (FIG. 5G). Moreover, cerebral Aβ plaque burden in the hippocampal dentate gyrus, and the cerebral cortex (5$^{th}$ layer), two brain regions exhibiting robust Aβ plaque pathology in 5XFAD AD-Tg mice (Oakley et al, 2006), was reduced (FIG. 6A, B). Evaluating the effect on cognitive function, using the Morris water maze (MWM) test, revealed a significant improvement in spatial learning and memory in AD-Tg/DTR$^+$ mice following the Treg depletion, relative to DTx-treated AD-Tg/DTR$^-$ aged matched mice, reaching performance similar to that of WT mice (FIG. 6C-E). Taken together, these data demonstrated that transiently breaking Treg-mediated systemic immune suppression in AD-Tg mice resulted in accumulation of inflammation-resolving cells, including mo-Φ and Tregs, in the brain, and was followed by resolution of the neuroinflammatory response, clearance of Aβ, and reversal of cognitive decline.

Example 3. Weekly Administration of Copolymer-1 Reduces Treg-Mediated Systemic Immune Suppression, Improves CP Gateway Activity, and Mitigates AD Pathology To further substantiate the causal nature of the inverse relationship between systemic immune suppression, CP function and AD pathology, we next made use of the immunomodulatory compound, Glatiramer acetate (GA; also known as Copolymer-1, or Copaxone®), which in a weekly administration regimen was found to have a therapeutic effect in the APP/PS1 mouse model of AD (Butovsky et al, 2006); this effect was functionally associated with mo-MΦ recruitment to cerebral sites of disease pathology (Butovsky et al, 2007). Here, we first examined whether the CP in APP/PS1 AD-Tg mice, similarly to our observation in 5XFAD AD-Tg mice, is also deficient with respect to IFN-γ expression levels. We found that in APP/PS1 AD-Tg mice, IFN-γ levels at the CP were reduced relative to age-matched WT controls (FIG. 7A). These results encouraged us to test whether the therapeutic effect of weekly-GA in APP/PS1 mice (Butovsky et al, 2006), could be reproduced in 5XFAD AD-Tg mice, and if so, whether it would affect systemic Tregs, and activation of the CP for mo-MΦ trafficking. We therefore treated 5XFAD AD-Tg mice with a weekly administration regimen of GA over a period of 4 weeks (henceforth, "weekly-GA"; schematically depicted in FIG. 8A). We found that 5XFAD AD-Tg mice treated with weekly-GA, showed reduced neuroinflammation (FIG. 8B-D), and improved cognitive performance, which lasted up to 2 months after the treatment (FIG. 8E-I). Examining by flow cytometry the effect of weekly-GA on systemic immunity and on the CP, we found reduced splenocyte Foxp3$^+$ Treg levels (FIG. 9A), and an increase in IFN-γ-producing cells at the CP of the treated 5XFAD AD-Tg mice, reaching similar levels as those observed in WT controls (FIG. 9B). The elevated level of IFN-γ-expressing cells at the CP in the weekly-GA treated mice, was accompanied by upregulated epithelial expression of leukocyte trafficking molecules (FIG. 9C).

Figure 9D:
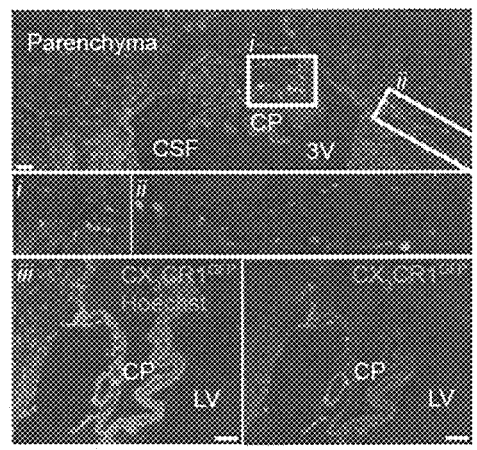
Figure 9E:
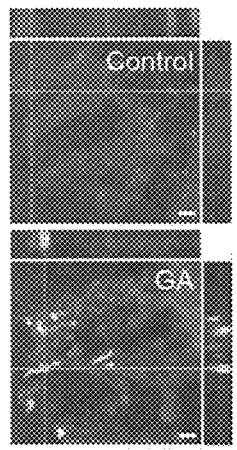
Figure 9F:
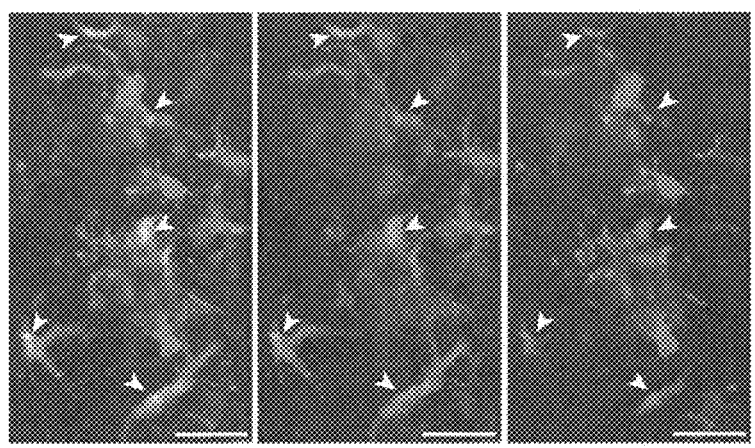
Figure 9G:
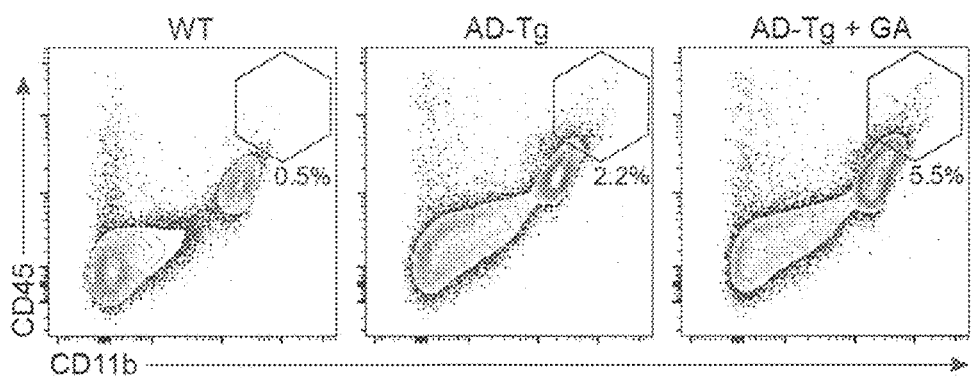
Figure 9H:
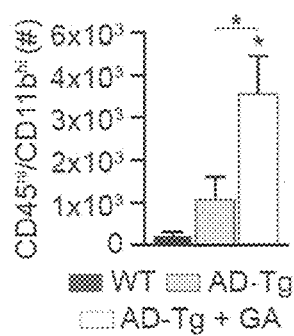

To detect infiltrating mo-MΦ entry to the CNS, we used 5XFAD AD-Tg/CX$_3$CR1$^{GFP/+}$ bone marrow (BM) chimeric mice (prepared using head protection), allowing the visualization of circulating (green fluorescent protein (GFP)$^+$ labeled) myeloid cells (Shechter et al, 2009; Shechter et al, 2013). We found increased homing of GFP$^+$ mo-Φ to the CP and to the adjacent ventricular spaces following weekly-GA treatment, as compared to vehicle-treated AD-Tg/CX$_3$CR1$^{GFP/+}$ controls (FIG. 9D-E). Immunohistochemistry of the brain parenchyma revealed the presence of GFP$^+$ mo-Φ accumulation at sites of cerebral plaque formation (FIG. 9F), and quantification of infiltrating myeloid cells, by flow cytometry analysis of the hippocampus in AD-Tg non-chimeric mice, showed increased numbers of CD11b$^{high}$CD45$^{high}$-expressing cells (FIG. 9G, H). Together, these results substantiated the functional linkage between mo-MΦ recruitment to sites of AD pathology, reduction of systemic Treg levels and IFN-γ-dependent activation of the CP.

Figure 10A:
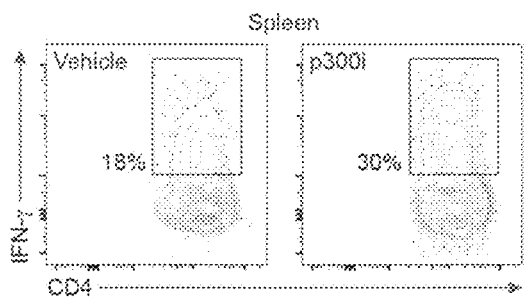
FIGS. 10A-H depict the therapeutic effect of administration of a p300 inhibitor (C646) in AD-Tg mice.
Figure 10B:
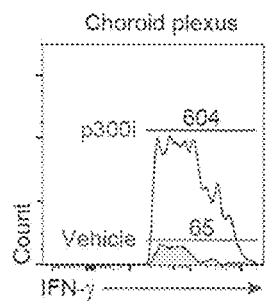
Figure 10C:
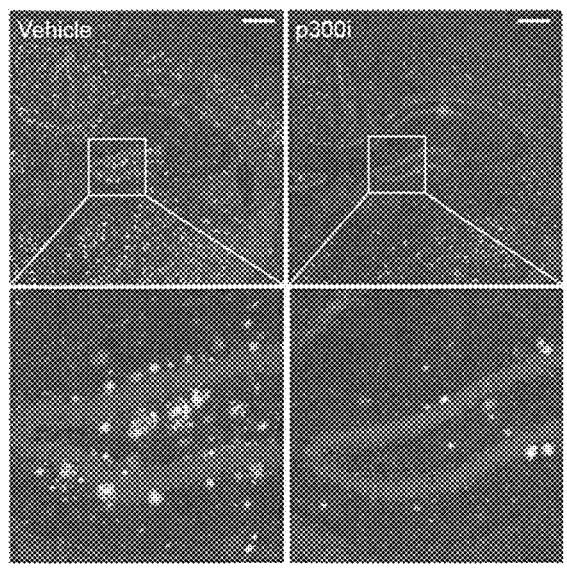
Figure 10D:
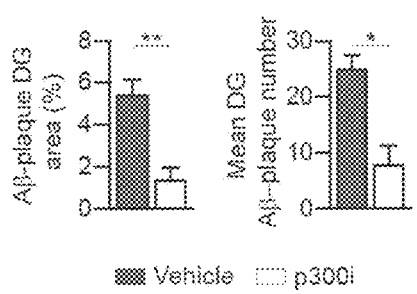
Figure 10E:
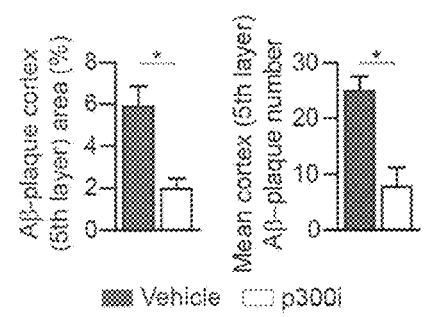
Figure 10F:
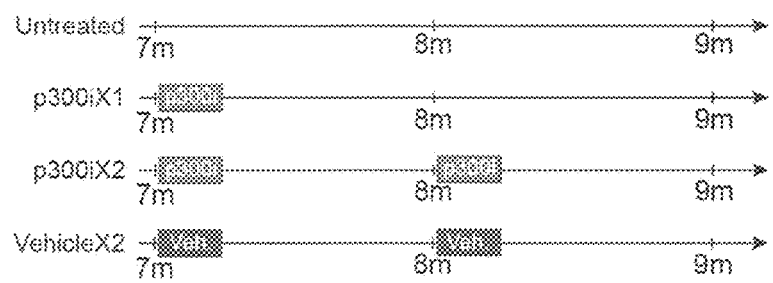
Figure 10G:
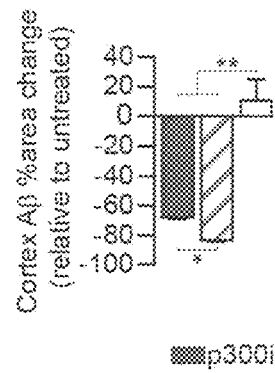
Figure 10H:
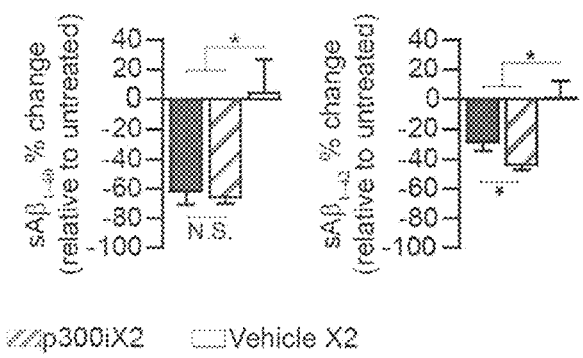

Example 4. Interference With Treg Activity Using a Small Molecule Histone Acetyltransferase Inhibitor The findings above, which suggested that Treg-mediated systemic immune suppression interferes with the ability to fight AD pathology, are reminiscent of the function attributed to Tregs in cancer immunotherapy, in which these cells hinder the ability of the immune system to mount an effective anti-tumor response (Bos & Rudensky, 2012; Nishikawa & Sakaguchi, 2010). Therefore, we considered that a treatment that directly interferes with Foxp3$^+$ Treg cell activity might be advantageous in AD. We tested p300i (C646 (Bowers et al, 2010)), a nonpeptidic inhibitor of p300, a histone acetyltransferase that regulates Treg function (Liu et al, 2013); this inhibitor was shown to affect Treg suppressive activities while leaving protective T effector cell responses intact (Liu et al, 2013). We found that mice treated with p300i, compared to vehicle (DMSO) treated controls, showed elevated levels of systemic IFN-γ-expressing cells in the spleen (FIG. 10A), as well as in the CP (FIG. 10B). We next treated AD-Tg mice with either p300i or vehicle over the course of 1 week, and examined them 3 weeks later for cerebral Aβ plaque burden. Immunohistochemical analysis revealed a significant reduction in cerebral Aβ plaque load in the p300i treated AD-Tg mice (FIG. 10C-E). We also tested whether the effect on plaque pathology following one course of treatment would last beyond the 3 weeks, and if so, whether additional courses of treatment would contribute to a long-lasting effect. We therefore compared AD-Tg mice that received a single course of p300i treatment and were examined 2 month later, to an age-matched group that received two courses of treatments during this period, with a 1-month interval in between (schematically depicted in FIG. 10F). We found that the reduction of cerebral plaque load was evident even two months after a single course of treatment, but was stronger in mice that received two courses of treatments with a 1-month interval in between (FIG. 10G). Since impaired synaptic plasticity and memory in AD is associated with elevated cerebral levels of soluble $A\beta_{1-40}/A\beta_{1-42}$ (sAβ) levels (Shankar et al, 2008), we also measured sAβ levels following a single or repeated cycles of p300i treatment. Again, we found that both one and two courses (with an interval of 1 month in between) were effective in reducing cerebral sAβ, yet this effect was stronger following repeated courses with respect to the effect on $sA\beta_{1-42}$ (FIG. 10H). These results indicated that while a single short-term course of treatment is effective, repeated courses of treatments would be advantageous to maintain a long-lasting therapeutic effect, similar to our observations following weekly-GA treatment.

Example 5. Therapeutic Potential of PD-1 Immune Checkpoint Blockade in Alzheimer's Disease We first tested whether targeting the PD-1 inhibitory pathway could affect IFN-γ-associated systemic immunity in 5XFAD AD transgenic (AD-Tg) mice, which co-expresses five mutations associated with familial AD (Oakley et al, 2006). AD-Tg mice at the age of 10 months, a time point at which cerebral pathology is advanced, were administrated with two intraperitoneal (i.p.) injections of either blocking antibodies directed at PD-1 (anti-PD-1) or IgG control antibodies, on days 1 and 4, and then examined on day 7. Flow cytometry analysis revealed that blockade of the PD-1 pathway resulted in elevated frequencies of IFN-γ-producing CD4+ T splenocytes (FIG. 11A, B).

TABLE 2

GO annotation, related to FIG. 11.

| GO term | Description | P-value | FDR q-value |
|---|---|---|---|
| GO: 0034341 | response to interferon-gamma | 2.13E−14 | 2.30E−10 |
| GO: 0048002 | antigen processing and presentation of peptide antigen | 3.05E−10 | 1.65E−06 |
| GO: 0019886 | antigen processing and presentation of exogenous peptide antigen via MHC class II | 4.11E−10 | 1.48E−06 |
| GO: 0002478 | antigen processing and presentation of exogenous peptide antigen | 5.26E−10 | 1.42E−06 |
| GO: 0034097 | response to cytokine | 5.67E−10 | 1.22E−06 |
| GO: 0002504 | antigen processing and presentation of peptide or polysaccharide antigen via MHC class II | 1.04E−09 | 1.87E−06 |
| GO: 0002495 | antigen processing and presentation of peptide antigen via MHC class II | 1.04E−09 | 1.60E−06 |
| GO: 0019884 | antigen processing and presentation of exogenous antigen | 5.82E−09 | 7.86E−06 |
| GO: 0019882 | antigen processing and presentation | 1.43E−07 | 1.71E−04 |
| GO: 0035456 | response to interferon-beta | 6.67E−07 | 7.20E−04 |
| GO: 0006955 | immune response | 1.07E−06 | 1.05E−03 |
| GO: 0002819 | regulation of adaptive immune response | 1.92E−06 | 1.73E−03 |
| GO: 0071345 | cellular response to cytokine stimulus | 2.21E−06 | 1.84E−03 |
| GO: 0071346 | cellular response to interferon-gamma | 2.21E−06 | 1.71E−03 |

Gene ontology terms enriched in the CP of AD-Tg mice treated with anti-PD-1, when compared to IgG treated and untreated AD-Tg controls. Log 10 values of all RNA sequences of the CP were ranked according to their differential expression levels and analyzed.

Figure 11D:
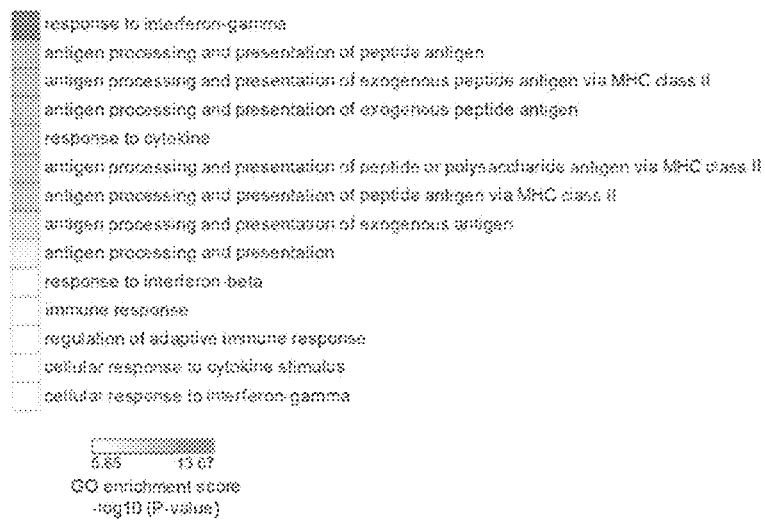
FIGS. 11 A-D show that PD-1 blockade augments IFN-γ-dependent choroid plexus activity in AD-Tg mice. 10-month old AD-Tg mice were i.p. injected on day 1 and day 4 with 250 ug of either anti-PD-1 or control IgG, and examined at days 7-10 for the effect on the systemic immune response and CP activity. (A-B) Representative flow cytometry plots (A), and quantitative analysis (B), of $CD4^+IFN-γ^+$ splenocyte frequencies (intracellularly stained and pre-gated on CD45 and TCR-β), in αPD-1 or IgG treated AD-Tg mice, and untreated AD-Tg and WT controls (n=4-6 per group; one-way ANOVA followed by Newman-Keuls post hoc analysis; **, $P<0.01$ between the indicted treated groups; error bars represent mean±s.e.m.). (C) mRNA expression levels of ifn-g, measured by RT-qPCR in the CP of AD-Tg mice treated with anti-PD-1 when compared to IgG treated and untreated AD-Tg controls (D) GO annotation terms enriched in RNA-Seq in CPs of the same mice (n=3-5 per group; one-way ANOVA followed by Newman-Keuls post hoc analysis; *, $P<0.05$) (gray scale corresponds to negative log-base 10 of P-value).

We next examined whether this systemic immune response affected the CP activity. Genome wide RNA-sequencing of the CP (Not shown; the full analysis will be disclosed in a report by the present inventors having the title of Example 5 and it can be obtained from the inventors upon request) showed an expression profile associated with response to IFN-γ (FIG. 11D and Table 2), and real-time quantitative PCR (RT-qPCR) verified elevated IFN-γ mRNA levels at the CP, when compared to IgG-treated or untreated AD-Tg controls (FIG. 11C). These findings confirmed a systemic, and CP tissue-specific, IFN-γ immune response following PD-1 blockade, and encouraged us to next test the effect on disease pathology.

To examine the functional impact of PD-1 blockade on AD pathology, we treated 10-month old AD-Tg mice with either anti-PD-1 or IgG control antibodies, and evaluated the effect on spatial learning and memory performance, using the radial arm water maze (RAWM) task.

Figure 12A:
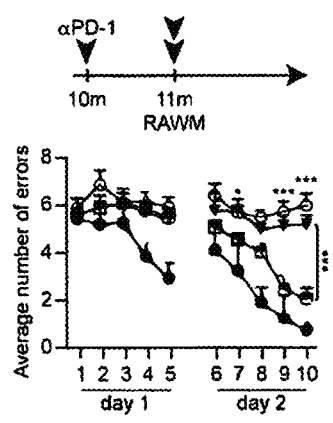
FIGS. 12A-B show that PD-1 blockade mitigates cognitive decline in AD-Tg mice. 10-month old AD-Tg mice were i.p. injected on day 1 and day 4 with 250 ug of either anti-PD-1 or control IgG, and examined 1 or 2 months later for the effect on pathology. (A-B) Scheme of the experimental design. Single arrows indicate time points of treatment, and double arrows indicate time points of cognitive testing. Cognitive performance of anti-PD-1 and IgG treated mice, compared to age-matched WT and untreated AD-Tg mice, assessed by the average number of errors per day in the RAWM learning and memory task (n=6-8 per group; two-way repeated measures ANOVA followed by Bonferroni post-hoc for individual pair comparisons). (A) Performance of AD-Tg mice in the RAWM after 1 treatment session with anti-PD-1 or IgG control. (B) Effect of single anti-PD-1 treatment session, or 2 sessions with a 1 month interval on performance.
Figure 12B:
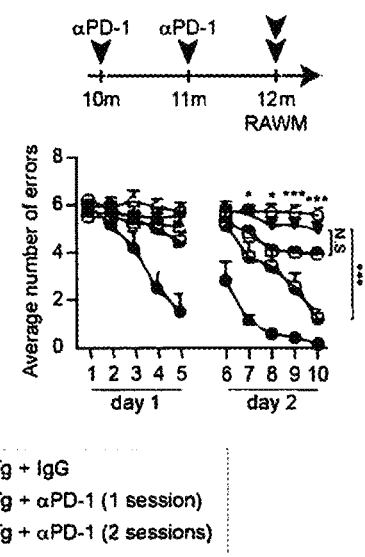

One month following treatment (two i.p. injections with 3-day interval), anti-PD1 treated AD-Tg mice exhibited a significant improvement in cognitive function relative to IgG-treated or untreated age-matched controls, reaching cognitive levels similar to that of age-matched WT mice (FIG. 12A). We next tested whether the benefit of PD-1 blockade on cognitive performance in AD-Tg mice would last beyond 1 month, and whether additional therapeutic sessions would be advantageous. We treated AD-Tg mice with anti-PD-1 at the age of 10 months ("1 session") or at both 10 and 11 months of age ("2 sessions"), and examined the outcome on cognitive performance at the age of 12 months (schematically depicted in FIG. 12B). Control groups included WT mice, untreated AD-Tg mice, and AD-Tg mice that received two sessions of IgG treatment. We found that while a single session of anti-PD-1 administration had a beneficial effect on spatial learning and memory 1 month following the treatment (FIG. 12A), no significant effect could be detected in mice that received a single session of treatment and were tested 2 months later (FIG. 12B). In contrast, AD-Tg mice that received two sessions of anti-PD-1, at a 1-month interval, displayed cognitive performance similar to that of WT mice, at the end of the 2-month timeframe (FIG. 12B).

Figure 13B:
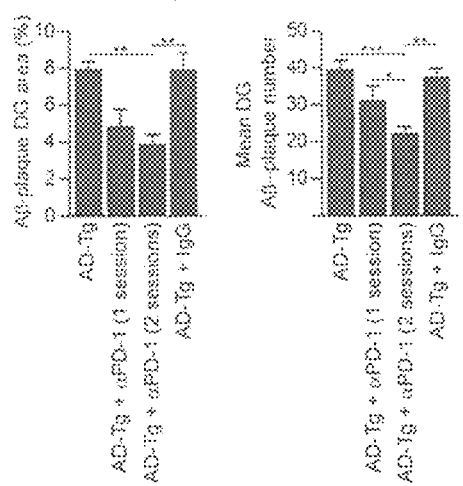
Figure 13C:
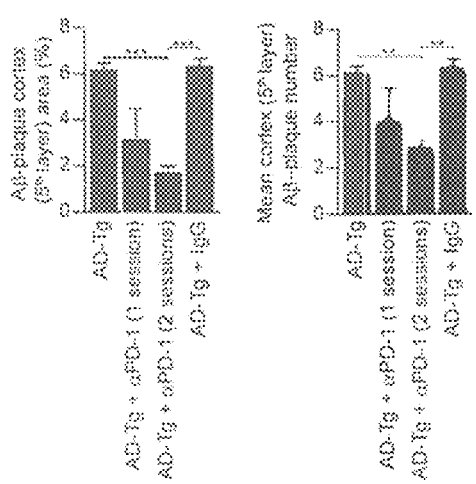
Figure 13D:
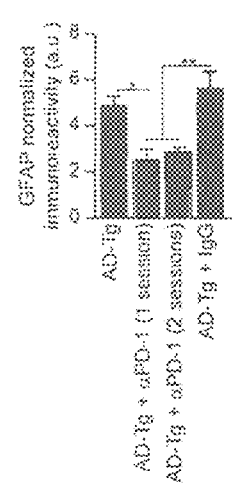

Finally, we examined whether PD-1 blockade affected AD pathology as manifested by cerebral Aβ plaque load and gliosis. Brains of AD-Tg mice that received anti-PD-1 or IgG in either one or two sessions were examined by immunohistochemistry for Aβ and glial fibrillary acid protein (GFAP). We found that cerebral Aβ plaque burden was reduced in the hippocampal dentate gyms (FIG. 13A, B), and the cerebral cortex (5th layer) (FIG. 13A, C), two brain regions exhibiting robust Aβ plaque pathology in 5XFAD mice (Oakley et al, 2006). The effect on Aβ clearance was evident following a single session of anti-PD-1 administration, and was more robust following two sessions. Quantitative analysis of GFAP immunostaining showed reduced hippocampal astrogliosis in both AD-Tg mice treated with 1 session, and those treated with 2 sessions of PD-1 blockade, relative to IgG-treated controls (FIG. 13A, D).

Example 6. Therapeutic Potential of PD-1 in Combination With CTLA4 Immune Checkpoint Blockade in Alzheimer's Disease At 10 months of age, 5XFAD Alzheimer's disease (AD) transgenic (Tg) mice are injected i.p. with either 250 μg of anti-PD1 (RMP1-14; #BE0146; Bioxcell Lifesciences Pvt. LTD.) and 250 μg anti-CTLA4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and are examined 3 weeks after for their cognitive performance by radial arm water maze (RAWM) spatial learning and memory task, as described above.

Some mice receive an additional treatment session with an interval session of 3 weeks. Control groups are either treated with IgG or untreated, and all groups of mice are tested for their cognitive performance 3 weeks later.

It is expected that the mice treated with the combination of antibodies display significant cognitive improvement in comparison to IgG-treated and untreated AD-Tg mice as well as a significant reduction of cerebral plaque load.

Example 7. Therapeutic Potential of Immune Checkpoint Blockade Approch in PTSD Pathology Severely stressful conditions or chronic stress can lead to posttraumatic stress disorder (PTSD) and depression. We adopted a physiological PTSD-like animal model in which the mice exhibit hypervigilant behaviour, impaired attention, increased risk assessment, and poor sleep (Lebow et al, 2012). In this experimental model of PTSD induction, mice are habituated for 10 days to a reverse day/night cycle, inflicted with two episodes of electrical shocks (the trauma and the trigger), referred to as a "PTSD induction", and evaluated at different time points subsequent to trauma. Following the traumatic event mice are injected with said compound which blocks immune checkpoints. The mice are treated according to one of the following regimens:
Mice are injected i.p. with either 250 μg of anti-PD1 (RMP1-14; #BE0146; Bioxcell Lifesciences Pvt. LTD.) or control IgG (IgG2a; #BE0089; Bioxcell Lifesciences Pvt. LTD.) antibodies, on day 1 and day 4 following the traumatic event, and examined after an additional interval session of two weeks; or
Mice are injected i.p. with either 250 μg of anti-PD1 (RMP1-14; #BE0146; Bioxcell Lifesciences Pvt. LTD.) and 250 μg anti-CTLA4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and examined after an interval session of two weeks;
Mice are treated with any of the other active agents disclosed herein, on day 1 and day 4 of the experiment, and examined after an interval session of two weeks.
Some mice receive an additional treatment session with an appropriate interval session.

It is expected that mice that receive the treatment do not display anxiety behavior associated with PTSD in this experimental model, as assessed by time spent exploring and risk assessing in dark/light maze or the other behavioral tasks described in (Lebow et al, 2012).

Example 8. Therapeutic Potential of Immune Checkpoint Blockade Approach in Parkinson's Disease Pathology Parkinson disease (PD) transgenic (Tg) mice are used in these experiment. The mice are treated at the progressive stages of disease according to one of the following regimens:
Mice are injected i.p. with either 250 μg of anti-PD1 (RMP1-14; #BE0146; Bioxcell Lifesciences Pvt. LTD.) or control IgG (IgG2a; #BE0089; Bioxcell Lifesciences Pvt. LTD.) antibodies, on day 1 and day 4 following the traumatic event, and examined after an additional interval session of two weeks;
Mice are injected i.p. with either 250 μg of anti-PD1 (RMP1-14; #BE0146; Bioxcell Lifesciences Pvt. LTD.) and 250 μg anti-CTLA4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and examined after an interval session of two weeks;
Mice are treated with any of the other active agents disclosed herein, on day 1 and day 4 of the experiment, and examined after an interval session of two weeks.
Some mice receive an additional treatment session with an appropriate interval session (about 3 weeks to one month).

Motor neurological functions are evaluated using for example the rotarod performance test, which assesses the capacity of the mice to stay on a rotating rod.

It is expected that PD-Tg mice treated with one treatment session show significant improved motor performance, compared to IgG-treated or vehicle treated control group, or untreated group. PD-Tg mice which receive two courses of therapy, and examined after an appropriate interval session are expected to show a long-lasting therapeutic effect. To maintain this therapeutic effect mice are subjected to an active session of treatment with an appropriate interval session between each session.

Example 9. Therapeutic Potential of PD-1 in Combination With CTLA4 Immune Checkpoint Blockade in Huntington's Disease Pathology The model used in these experiments may be the Huntington's disease (HD) R6/2 transgenic mice (Tg) test system. R6/2 transgenic mice over express the mutated human huntingtin gene that includes the insertion of multiple CAG repeats mice at the progressive stages of disease. These mice show progressive behavioral-motor deficits starting as early as 5-6 weeks of age, and leading to premature death at 10-13 weeks. The symptoms include low body weight, clasping, tremor and convulsions.

The mice are treated according to one of the following regimens when they are 45 days old:

Mice are injected i.p. with either 250 µg of anti-PD1 (RMP1-14; #BE0146; Bioxcell Lifesciences Pvt. LTD.) or control IgG (IgG2a; #BE0089; Bioxcell Lifesciences Pvt. LTD.) antibodies, on day 1 and day 4 following the traumatic event, and examined after an additional interval session of two weeks;

Mice are injected i.p. with either 250 µg of anti-PD1 (RMP1-14; #BE0146; Bioxcell Lifesciences Pvt. LTD.) and 250 µg anti-CTLA4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and examined after an interval session of two weeks.

Mice are treated with any of the other active agents disclosed herein, on day 1 and day 4 of the experiment, and examined after an interval session of two weeks.

Some mice receive an additional treatment session with an appropriate interval session (about 3 weeks to one month).

Motor neurological functions are evaluated using for example the rotarod performance test, which assesses the capacity of the mice to stay on a rotating rod.

It is expected that HD-Tg mice treated with one treatment session show significant improved motor performance, compared to IgG-treated or vehicle treated control group, or untreated group. HD-Tg mice which receive which receive two courses of therapy, and examined after an appropriate interval session are expected to show a long-lasting therapeutic effect. To maintain this therapeutic effect mice are subjected to an active session of treatment with an appropriate interval session between each session.

Example 10. Therapeutic Potential of Immune Checkpoint Blockade Approach in Amyotrophic Lateral Sclerosis Pathology The model used in this experiment may be the transgenic mice overexpressing the defective human mutant SOD1 allele containing the Gly93→Ala (G93A) gene (B6SJL-TgN (SOD1-G93A)1Gur (herein "ALS mice"). This model develop motor neuron disease and thus constitute an accepted animal model for testing ALS.

The mice are treated according to one of the following regimens when they are 75 days old:

Mice are injected i.p. with either 250 µg of anti-PD1 (RMP1-14; #BE0146; Bioxcell Lifesciences Pvt. LTD.) or control IgG (IgG2a; #BE0089; Bioxcell Lifesciences Pvt. LTD.) antibodies, on day 1 and day 4 following the traumatic event, and examined after an additional interval session of two weeks;

Mice are injected i.p. with either 250 µg of anti-PD1 (RMP1-14; #BE0146; Bioxcell Lifesciences Pvt. LTD.) and 250 µg anti-CTLA4 (InVivoMAb anti-mCD152; #BE0131; Bioxcell Lifesciences Pvt. LTD.) or control IgG (IgG2a, #BE0089 or Polyclonal Syrian Hamster IgG, #BE0087; Bioxcell Lifesciences Pvt. LTD.) antibodies, on day 1 and day 4 of the experiment, and examined after an interval session of two weeks.

Mice are treated with any of the other active agents disclosed herein, on day 1 and day 4 of the experiment, and examined after an interval session of two weeks.

Some mice receive an additional treatment session with an appropriate interval session (about 3 weeks to month).

Motor neurological functions are evaluated using for example the rotarod performance test, which assesses the capacity of the mice to stay on a rotating rod, or mice are allowed to grasp and hold onto a vertical wire (2 mm in diameter) with a small loop at the lower end. A vertical wire allows mice to use both fore- and hindlimbs to grab onto the wire. The wire is maintained in a vertically oriented circular motion (the circle radius was 10 cm) at 24 rpm. The time that the mouse is able to hang onto the wire is recorded with a timer.

It is expected that ALS mice treated with one treatment session show significant improved motor performance, compared to IgG-treated or vehicle treated control group, or untreated group. ALS mice which receive which receive two courses of therapy, and examined after an appropriate interval session are expected to show a long-lasting therapeutic effect. To maintain this therapeutic effect mice are subjected to an active session of treatment with an appropriate interval session between each session.

REFERENCES

Akiyama H, Barger S, Barnum S, Bradt B, Bauer J, Cole G M, Cooper N R, Eikelenboom P, Emmerling M, Fiebich B L, Finch C E, Frautschy S, Griffin W S, Hampel H, Hull M, Landreth G, Lue L, Mrak R, Mackenzie I R, McGeer P L, O'Banion M K, Pachter J, Pasinetti G, Plata-Salaman C, Rogers J, Rydel R, Shen Y, Streit W, Strohmeyer R, Tooyoma I, Van Muiswinkel F L, Veerhuis R, Walker D, Webster S, Wegrzyniak B, Wenk G, Wyss-Coray T (2000) Inflammation and Alzheimer's disease. *Neurobiology of aging* 21: 383-421

Alamed J, Wilcock D M, Diamond D M, Gordon M N, Morgan D (2006) Two-day radial-arm water maze learning and memory task; robust resolution of amyloid-related memory deficits in transgenic mice. *Nature protocols* 1: 1671-1679

Bai A, Lu N, Guo Y, Liu Z, Chen J, Peng Z (2009) All-trans retinoic acid down-regulates inflammatory responses by shifting the Treg/Th17 profile in human ulcerative and murine colitis. *Journal of leukocyte biology* 86: 959-969

Baruch K, Deczkowska A, David E, Castellano J M, Miller O, Kertser A, Berkutzki T, Barnett-Itzhaki Z, Bezalel D, Wyss-Coray T, Amit I, Schwartz M (2014) Aging. Aging-induced type I interferon response at the choroid plexus negatively affects brain function. *Science* 346: 89-93

Baruch K, Kertser A, Porat Z, Schwartz M (2015) Cerebral nitric oxide represses choroid plexus NFkappaB-dependent gateway activity for leukocyte trafficking. *The EMBO journal*

Baruch K, Ron-Harel N, Gal H, Deczkowska A, Shifrut E, Ndifon W, Mirlas-Neisberg N, Cardon M, Vaknin I, Cahalon L, Berkutzki T, Mattson M P, Gomez-Pinilla F, Friedman N, Schwartz M (2013) CNS-specific immunity at the choroid plexus shifts toward destructive Th2 inflammation in brain aging. *Proceedings of the National Academy of Sciences of the United States of America* 110: 2264-2269

Borchelt D R, Ratovitski T, van Lare J, Lee M K, Gonzales V, Jenkins N A, Copeland N G, Price D L, Sisodia S S (1997) Accelerated amyloid deposition in the brains of transgenic mice coexpressing mutant presenilin 1 and amyloid precursor proteins. *Neuron* 19: 939-945

Bos P D, Rudensky A Y (2012) Treg cells in cancer: a case of multiple personality disorder. *Science translational medicine* 4: 164fs144

Bowers E M, Yan G, Mukherjee C, Orry A, Wang L, Holbert M A, Crump N T, Hazzalin C A, Liszczak G, Yuan H, Larocca C, Saldanha S A, Abagyan R, Sun Y, Meyers D J, Marmorstein R, Mahadevan L C, Alani R M, Cole P A (2010) Virtual ligand screening of the p300/CBP histone acetyltransferase: identification of a selective small molecule inhibitor. *Chemistry & biology* 17: 471-482

Breitner J C, Haneuse S J, Walker R, Dublin S, Crane P K, Gray S L, Larson E B (2009) Risk of dementia and AD with prior exposure to NSAIDs in an elderly community-based cohort. *Neurology* 72: 1899-1905

Brestoff J R, Artis D (2013) Commensal bacteria at the interface of host metabolism and the immune system. *Nature immunology* 14: 676-684

Burgess A, Vigneron S, Brioudes E, Labbe J C, Lorca T, Castro A (2010) Loss of human Greatwall results in G2 arrest and multiple mitotic defects due to deregulation of the cyclin B-Cdc2/PP2A balance. *Proceedings of the National Academy of Sciences of the United States of America* 107: 12564-12569

Butovsky O, Koronyo-Hamaoui M, Kunis G, Ophir E, Landa G, Cohen H, Schwartz M (2006) Glatiramer acetate fights against Alzheimer's disease by inducing dendritic-like microglia expressing insulin-like growth factor 1. *Proceedings of the National Academy of Sciences of the United States of America* 103: 11784-11789

Butovsky O, Kunis G, Koronyo-Hamaoui M, Schwartz M (2007) Selective ablation of bone marrow-derived dendritic cells increases amyloid plaques in a mouse Alzheimer's disease model. *The European journal of neuroscience* 26: 413-416

Chen X, Oppenheim J J (2011) Resolving the identity myth: key markers of functional CD4+FoxP3+ regulatory T cells. *International immunopharmacology* 11: 1489-1496

Colombo M P, Piconese S (2007) Regulatory-T-cell inhibition versus depletion: the right choice in cancer immunotherapy. *Nature reviews Cancer* 7: 880-887

Coyne G O, Gulley J L (2014) Adding fuel to the fire: Immunogenic intensification. *Human vaccines & immunotherapeutics* 10: 3306-3312

Dalotto-Moreno T, Croci D O, Cerliani J P, Martinez-Allo V C, Dergan-Dylon S, Mendez-Huergo S P, Stupirski J C, Mazal D, Osinaga E, Toscano M A, Sundblad V, Rabinovich G A, Salatino M (2013) Targeting galectin-1 overcomes breast cancer-associated immunosuppression and prevents metastatic disease. *Cancer research* 73: 1107-1117

Duraiswamy J, Freeman G J, Coukos G (2014) Dual blockade of PD-1 and CTLA-4 combined with tumor vaccine effectively restores T-cell rejection function in tumors-response. *Cancer research* 74: 633-634; discussion 635

Francisco L M, Sage P T, Sharpe A H (2010) The PD-1 pathway in tolerance and autoimmunity. *Immunological reviews* 236: 219-242

Gabrilovich D I, Nagaraj S (2009) Myeloid-derived suppressor cells as regulators of the immune system. *Nature reviews Immunology* 9: 162-174

Galvin K C, Dyck L, Marshall N A, Stefanska A M, Walsh K P, Moran B, Higgins S C, Dungan L S, Mills K H (2013) Blocking retinoic acid receptor-alpha enhances the efficacy of a dendritic cell vaccine against tumours by suppressing the induction of regulatory T cells. *Cancer immunology, immunotherapy: CII* 62: 1273-1282

Ghiringhelli F, Bruchard M, Chalmin F, Rebe C (2012) Production of adenosine by ectonucleotidases: a key factor in tumor immunoescape. *Journal of biomedicine & biotechnology* 2012: 473712

Group A R, Lyketsos C G, Breitner J C, Green R C, Martin B K, Meinert C, Piantadosi S, Sabbagh M (2007) Naproxen and celecoxib do not prevent AD in early results from a randomized controlled trial. *Neurology* 68: 1800-1808

Hardy J, Selkoe D J (2002) The amyloid hypothesis of Alzheimer's disease: progress and problems on the road to therapeutics. *Science* 297: 353-356

He F, Balling R (2013) The role of regulatory T cells in neurodegenerative diseases. *Wiley interdisciplinary reviews Systems biology and medicine* 5: 153-180

Hirayama M, Nishikawa H, Nagata Y, Tsuji T, Kato T, Kageyama S, Ueda S, Sugiyama D, Hori S, Sakaguchi S, Ritter G, Old L J, Gnjatic S, Shiku H (2013) Overcoming regulatory T-cell suppression by a lyophilized preparation of *Streptococcus pyogenes*. *European journal of immunology* 43: 989-1000

Hong J, Li N, Zhang X, Zheng B, Zhang J Z (2005) Induction of CD4+CD25+ regulatory T cells by copolymer-I through activation of transcription factor Foxp3. *Proceedings of the National Academy of Sciences of the United States of America* 102: 6449-6454

Joller N, Peters A, Anderson A C, Kuchroo V K (2012) Immune checkpoints in central nervous system autoimmunity. *Immunological reviews* 248: 122-139

Ju Y, Shang X, Liu Z, Zhang J, Li Y, Shen Y, Liu Y, Liu C, Liu B, Xu L, Wang Y, Zhang B, Zou J (2014) The Tim-3/galectin-9 pathway involves in the homeostasis of hepatic Tregs in a mouse model of concanavalin A-induced hepatitis. *Molecular immunology* 58: 85-91

Jung S, Aliberti J, Graemmel P, Sunshine M J, Kreutzberg G W, Sher A, Littman D R (2000) Analysis of fractalkine receptor CX(3)CR1 function by targeted deletion and green fluorescent protein reporter gene insertion. *Molecular and cellular biology* 20: 4106-4114

Kim J M, Rasmussen J P, Rudensky A Y (2007) Regulatory T cells prevent catastrophic autoimmunity throughout the lifespan of mice. *Nature immunology* 8: 191-197

Kim P S, Jochems C, Grenga I, Donahue R N, Tsang K Y, Gulley J L, Schlom J, Farsaci B (2014) Pan-Bcl-2 inhibitor, GX15-070 (obatoclax), decreases human T regulatory lymphocytes while preserving effector T lymphocytes: a rationale for its use in combination immunotherapy. *Journal of immunology* 192: 2622-2633

Kotsakis A, Harasymczuk M, Schilling B, Georgoulias V, Argiris A, Whiteside T L (2012) Myeloid-derived suppressor cell measurements in fresh and cryopreserved blood samples. *Journal of immunological methods* 381: 14-22

Kunis G, Baruch K, Miller O, Schwartz M (2015) Immunization with a Myelin-Derived Antigen Activates the Brain's Choroid Plexus for Recruitment of Immunoregulatory Cells to the CNS and Attenuates Disease Progression in a Mouse Model of ALS. *The Journal of neuroscience: the official journal of the Society for Neuroscience* 35: 6381-6393

Kunis G, Baruch K, Rosenzweig N, Kertser A, Miller O, Berkutzki T, Schwartz M (2013) IFN-gamma-dependent activation of the brain's choroid plexus for CNS immune surveillance and repair. *Brain: a journal of neurology* 136: 3427-3440

Lebow M, Neufeld-Cohen A, Kuperman Y, Tsoory M, Gil S, Chen A (2012) Susceptibility to PTSD-like behavior is mediated by corticotropin-releasing factor receptor type 2 levels in the bed nucleus of the stria terminalis. *J Neurosci* 32: 6906-6916

Lesokhin A M, Callahan M K, Postow M A, Wolchok J D (2015) On being less tolerant: enhanced cancer immunosurveillance enabled by targeting checkpoints and agonists of T cell activation. *Science translational medicine* 7: 280sr281

Liu Y, Wang L, Predina J, Han R, Beier U H, Wang L C, Kapoor V, Bhatti T R, Akimova T, Singhal S, Brindle P K, Cole P A, Albelda S M, Hancock W W (2013) Inhibition of p300 impairs Foxp3(+) T regulatory cell function and promotes antitumor immunity. Nature medicine 19: 1173-1177

Marabelle A, Kohrt H, Sagiv-Barfi I, Ajami B, Axtell R C, Zhou G, Rajapaksa R, Green M R, Torchia J, Brody J, Luong R, Rosenblum M D, Steinman L, Levitsky H I, Tse V, Levy R (2013) Depleting tumor-specific Tregs at a single site eradicates disseminated tumors. The Journal of clinical investigation 123: 2447-2463

Mellman I, Coukos G, Dranoff G (2011) Cancer immunotherapy comes of age. *Nature* 480: 480-489

Michaud J P, Bellavance M A, Prefontaine P, Rivest S (2013) Real-time in vivo imaging reveals the ability of monocytes to clear vascular amyloid beta. *Cell reports* 5: 646-653

Nishikawa H, Sakaguchi S (2010) Regulatory T cells in tumor immunity. *International journal of cancer Journal international du cancer* 127: 759-767

Oakley H, Cole S L, Logan S, Maus E, Shao P, Craft J, Guillozet-Bongaarts A, Ohno M, Disterhoft J, Van Eldik L, Berry R, Vassar R (2006) Intraneuronal beta-amyloid aggregates, neurodegeneration, and neuron loss in transgenic mice with five familial Alzheimer's disease mutations: potential factors in amyloid plaque formation. *The Journal of neuroscience: the official journal of the Society for Neuroscience* 26: 10129-10140

Ohaegbulam K C, Assal A, Lazar-Molnar E, Yao Y, Zang X (2015) Human cancer immunotherapy with antibodies to the PD-1 and PD-L1 pathway. *Trends in molecular medicine* 21: 24-33

Pardoll D M (2012) The blockade of immune checkpoints in cancer immunotherapy. *Nature reviews Cancer* 12: 252-264

Peng W, Liu C, Xu C, Lou Y, Chen J, Yang Y, Yagita H, Overwijk W W, Lizee G, Radvanyi L, Hwu P (2012) PD-1 blockade enhances T-cell migration to tumors by elevating IFN-gamma inducible chemokines. *Cancer research* 72: 5209-5218

Pere H, Montier Y, Bayry J, Quintin-Colonna F, Merillon N, Dransart E, Badoual C, Gey A, Ravel P, Marcheteau E, Batteux F, Sandoval F, Adotevi O, Chiu C, Garcia S, Tanchot C, Lone Y C, Ferreira L C, Nelson B H, Hanahan D, Fridman W H, Johannes L, Tartour E (2011) A CCR4 antagonist combined with vaccines induces antigen-specific CD8+ T cells and tumor immunity against self antigens. *Blood* 118: 4853-4862

Postow M A, Callahan M K, Wolchok J D (2015) Immune Checkpoint Blockade in Cancer Therapy. *Journal of clinical oncology: official journal of the American Society of Clinical Oncology*

Qin A, Wen Z, Zhou Y, Li Y, Li Y, Luo J, Ren T, Xu L (2013) MicroRNA-126 regulates the induction and function of CD4(+) Foxp3(+) regulatory T cells through PI3K/AKT pathway. *Journal of cellular and molecular medicine* 17: 252-264

Rosenkranz D, Weyer S, Tolosa E, Gaenslen A, Berg D, Leyhe T, Gasser T, Stoltze L (2007) Higher frequency of regulatory T cells in the elderly and increased suppressive activity in neurodegeneration. *Journal of neuroimmunology* 188: 117-127

Roy S, Barik S, Banerjee S, Bhuniya A, Pal S, Basu P, Biswas J, Goswami S, Chakraborty T, Bose A, Baral R (2013) Neem leaf glycoprotein overcomes indoleamine 2,3 dioxygenase mediated tolerance in dendritic cells by attenuating hyperactive regulatory T cells in cervical cancer stage IIIB patients. *Human immunology* 74: 1015-1023

Sakaguchi S, Yamaguchi T, Nomura T, Ono M (2008) Regulatory T cells and immune tolerance. *Cell* 133: 775-787

Saresella M, Calabrese E, Marventano I, Piancone F, Gatti A, Calvo M G, Nemni R, Clerici M (2010) PD1 negative and PD1 positive CD4+ T regulatory cells in mild cognitive impairment and Alzheimer's disease. *Journal of Alzheimer's disease: JAD* 21: 927-938

Schmidt S D, Nixon R A, Mathews P M (2005) ELISA method for measurement of amyloid-beta levels. *Methods in molecular biology* 299: 279-297

Schreiber R D, Old L J, Smyth M J (2011) Cancer immunoediting: integrating immunity's roles in cancer suppression and promotion. *Science* 331: 1565-1570

Schwartz M, Baruch K (2014a) Breaking peripheral immune tolerance to CNS antigens in neurodegenerative diseases: boosting autoimmunity to fight-off chronic neuroinflammation. Journal of autoimmunity 54: 8-14

Schwartz M, Baruch K (2014b) The resolution of neuroinflammation in neurodegeneration: leukocyte recruitment via the choroid plexus. *The EMBO journal* 33: 7-22

Shankar G M, Li S, Mehta T H, Garcia-Munoz A, Shepardson N E, Smith I, Brett F M, Farrell M A, Rowan M J, Lemere C A, Regan C M, Walsh D M, Sabatini B L, Selkoe D J (2008) Amyloid-beta protein dimers isolated directly from Alzheimer's brains impair synaptic plasticity and memory. *Nature medicine* 14: 837-842

Shechter R, London A, Varol C, Raposo C, Cusimano M, Yovel G, Rolls A, Mack M, Pluchino S, Martino G, Jung S, Schwartz M (2009) Infiltrating blood-derived macrophages are vital cells playing an anti-inflammatory role in recovery from spinal cord injury in mice. *PLoS medicine* 6: e1000113

Shechter R, Miller O, Yovel G, Rosenzweig N, London A, Ruckh J, Kim K W, Klein E, Kalchenko V, Bendel P, Lira S A, Jung S, Schwartz M (2013) Recruitment of beneficial M2 macrophages to injured spinal cord is orchestrated by remote brain choroid plexus. *Immunity* 38: 555-569

Shevchenko I, Karakhanova S, Soltek S, Link J, Bayry J, Werner J, Umansky V, Bazhin A V (2013) Low-dose gemcitabine depletes regulatory T cells and improves survival in the orthotopic Panc02 model of pancreatic cancer. International journal of cancer *Journal international du cancer* 133: 98-107

Simpson T R, Li F, Montalvo-Ortiz W, Sepulveda M A, Bergerhoff K, Arce F, Roddie C, Henry J Y, Yagita H, Wolchok J D, Peggs K S, Ravetch J V, Allison J P, Quezada S A (2013) Fc-dependent depletion of tumor-infiltrating regulatory T cells co-defines the efficacy of anti-CTLA-4 therapy against melanoma. *The Journal of experimental medicine* 210: 1695-1710

Smith P M, Howitt M R, Panikov N, Michaud M, Gallini C A, Bohlooly Y M, Glickman J N, Garrett W S (2013) The microbial metabolites, short-chain fatty acids, regulate colonic Treg cell homeostasis. *Science* 341: 569-573

Suffner J, Hochweller K, Kuhnle M C, Li X, Kroczek R A, Garbi N, Hammerling G J (2010) Dendritic cells support homeostatic expansion of Foxp3+ regulatory T cells in Foxp3.LuciDTR mice. *Journal of immunology* 184: 1810-1820

Terme M, Colussi O, Marcheteau E, Tanchot C, Tartour E, Taieb J (2012) Modulation of immunity by antiangiogenic molecules in cancer. *Clinical & developmental immunology* 2012: 492920

Thomas-Schoemann A, Batteux F, Mongaret C, Nicco C, Chereau C, Annereau M, Dauphin A, Goldwasser F, Weill B, Lemare F, Alexandre J (2012) Arsenic trioxide exerts antitumor activity through regulatory T cell depletion mediated by oxidative stress in a murine model of colon cancer. *Journal of immunology* 189: 5171-5177

Tones K C, Araujo Pereira P, Lima G S, Bozzi I C, Rezende V B, Bicalho M A, Moraes E N, Miranda D M, Romano-Silva M A (2013) Increased frequency of T cells expressing IL-10 in Alzheimer disease but not in late-onset depression patients. *Progress in neuro-psychopharmacology & biological psychiatry* 47: 40-45

Vom Berg J, Prokop S, Miller K R, Obst J, Kahn R E, Lopategui-Cabezas I, Wegner A, Mair F, Schipke C G, Peters O, Winter Y, Becher B, Heppner F L (2012) Inhibition of IL-12/IL-23 signaling reduces Alzheimer's disease-like pathology and cognitive decline. *Nature medicine* 18: 1812-1819

Voo K S, Bover L, Harline M L, Vien L T, Facchinetti V, Arima K, Kwak L W, Liu Y J (2013) Antibodies targeting human OX40 expand effector T cells and block inducible and natural regulatory T cell function. *Journal of immunology* 191: 3641-3650

Walsh J T, Zheng J, Smirnov I, Lorenz U, Tung K, Kipnis J (2014) Regulatory T cells in central nervous system injury: a double-edged sword. *Journal of immunology* 193: 5013-5022

Ward F J, Dahal L N, Wijesekera S K, Abdul-Jawad S K, Kaewarpai T, Xu H, Vickers M A, Barker R N (2013) The soluble isoform of CTLA-4 as a regulator of T-cell responses. *European journal of immunology* 43: 1274-1285

Weber J S, Kudchadkar R R, Yu B, Gallenstein D, Horak C E, Inzunza H D, Zhao X, Martinez A J, Wang W, Gibney G, Kroeger J, Eysmans C, Sarnaik A A, Chen Y A (2013) Safety, efficacy, and biomarkers of nivolumab with vaccine in ipilimumab-refractory or -naive melanoma. *Journal of clinical oncology: official journal of the American Society of Clinical Oncology* 31: 4311-4318

Weber M S, Hohlfeld R, Zamvil S S (2007) Mechanism of action of glatiramer acetate in treatment of multiple sclerosis. *Neurotherapeutics: the journal of the American Society for Experimental NeuroTherapeutics* 4: 647-653

Weiskopf K, Ring A M, Schnorr P J, Volkmer J P, Volkmer A K, Weissman I L, Garcia K C (2013) Improving macrophage responses to therapeutic antibodies by molecular engineering of SIRPalpha variants. *Oncoimmunology* 2: e25773

Wyss-Coray T, Rogers J (2012) Inflammation in Alzheimer disease-a brief review of the basic science and clinical literature. *Cold Spring Harbor perspectives in medicine* 2: a006346

Zeng J, See A P, Phallen J, Jackson C M, Belcaid Z, Ruzevick J, Durham N, Meyer C, Harris T J, Albesiano E, Pradilla G, Ford E, Wong J, Hammers H J, Mathios D, Tyler B, Brem H, Tran P T, Pardoll D, Drake C G, Lim M (2013) Anti-PD-1 blockade and stereotactic radiation produce long-term survival in mice with intracranial gliomas. *International journal of radiation oncology, biology, physics* 86: 343-349

Zhao L, Sun L, Wang H, Ma H, Liu G, Zhao Y (2007) Changes of CD4+CD25+ Foxp3+ regulatory T cells in aged Balb/c mice. *Journal of leukocyte biology* 81: 1386-1394

Zheng H, Fridkin M, Youdim M (2015) New approaches to treating Alzheimer's disease. *Perspectives in medicinal chemistry* 7: 1-8

The invention claimed is:

1. A method of treating an Alzheimer's Disease, the method comprising administering to an individual in need thereof a composition comprising an anti-programmed death ligand 1 (PD-L1) antibody, or an anti-PD-L1 antibody fragment thereof having antagonistic or inactivating activity,
   wherein the composition is administered by a dosage regime comprising at least two courses of therapy, each course of therapy comprising in sequence a treatment session where the composition is administered to the individual followed by a non-treatment period where the composition is not administered to the individual, wherein the non-treatment period is longer than the treatment session,
   wherein, if administration of the composition during the treatment session is a repeated administration, the non-treatment period is longer than the period between repeated administrations during the treatment session, and
   wherein administration of the composition transiently reduces levels of systemic immunosuppression and increases choroid plexus gateway activity in facilitating selective recruitment of immune cells into the central nervous system, thereby treating the individual.

2. The method according to claim 1, wherein the administration of the composition during the treatment session is a single administration.

3. The method according to claim 1, wherein the administration of the composition during the treatment session is a repeated administration.

4. The method according to claim 3, wherein the repeated administration occurs once every two, three, four, five or six days.

5. The method according to claim 3, wherein the repeated administration occurs once weekly.

6. The method according to claim 3, wherein the repeated administration occurs once every four weeks.

7. The method according to claim 1, wherein the treatment session is from 3 days to four weeks.

8. The method according to claim 7, wherein the treatment session is from one week to four weeks.

9. The method according to claim 1, wherein the non-treatment period is from one week to six months.

10. The method according to claim 9, wherein the non-treatment period is from two weeks to six months.

11. The method according to claim 10, wherein the non-treatment period is from three weeks to six months.

12. The method according to claim 1, wherein the anti-PD-L1 antibody is a neutralizing anti-PD-L1 antibody.

13. The method according to claim 1, wherein the anti-PD-L1 antibody is a human or humanized anti-PD-L1 antibody.

14. The method according to claim 1, wherein the transient reduction in the level of systemic immunosuppression is associated with an increase in a systemic presence or activity of IFNγ-producing leukocytes and/or an increase in a systemic presence or activity of an IFNγ cytokine.

15. The method according to claim 1, wherein the transient reduction in the level of systemic immunosuppression is associated with an increase in a systemic presence or activity of effector T cells.

16. The method according to claim 1, wherein the transient reduction in the level of systemic immunosuppression is associated with a decrease in a systemic presence or activity of regulatory T cells and/or a decrease in a systemic presence of an IL-10 cytokine.

17. The method according to claim 1, wherein the transient reduction in the level of systemic immunosuppression is associated with a decrease in a systemic presence or myeloid-derived suppressor cells (MDSCs).

18. The method according to claim 1, wherein the transient reduction in the level of systemic immunosuppression occurs by release of a restraint imposed on the immune system by one or more immune checkpoints.

19. The method according to claim 18, wherein administration of the composition blocks the one or more immune checkpoints, thereby causing the transient reduction in the level of systemic immunosuppression.

20. The method according to claim 19, wherein the one or more immune checkpoints includes PD-1-PD-L1.

21. The method according to claim 1, wherein the administration of the composition during the treatment session is maintained at least until a systemic presence or activity of IFNγ-producing leukocytes and/or an IFNγ cytokine rises above a reference, at which point the administration is stopped, and the non-treatment period is maintained as long as the systemic presence or activity of IFNγ-producing leukocytes and/or an IFNγ cytokine is above the reference, wherein the reference includes
  a) a level of a systemic presence or activity of IFNγ-producing leukocytes and/or an IFNγ cytokine measured in the most recent blood sample obtained from the individual before the administering; or
  b) a level of a systemic presence or activity of IFNγ-producing leukocytes and/or an IFNγ cytokine characteristic of a population of individuals afflicted with the Alzheimer's Disease.

22. The method according to claim 1, wherein a cerebral level of soluble amyloid beta peptide is reduced in the individual, a cerebral amyloid beta (Aβ) plaque burden is reduced or cleared in the individual, a hippocampal gliosis is reduced in the individual, a cerebral level of a pro-inflammatory cytokine is reduced in the individual, a brain inflammation is decreased in the individual and/or a cognitive function is improved in the individual.

23. The method according to claim 22, wherein the improved cognitive function is learning, memory, creation of imagery, plasticity, thinking, awareness, reasoning, spatial ability, speech and language skills, language acquisition, capacity for judgment, attention or any combination thereof.

24. The method according to claim 1, wherein the immune cells include monocytes, macrophages, or T cells.

25. The method according to claim 24, wherein the T cells include regulatory T cells.

26. The method according to claim 1, wherein the anti-PD-L1 antibody is the only active ingredient of the composition.

* * * * *

SEQUENCE LISTING

```
<160> NUMBER OF SEQ ID NOS: 56

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ala Ala Ala Tyr Ala Ala Ala Ala Ala Lys Ala Ala Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Ala Glu Lys Tyr Ala Ala Ala Ala Ala Lys Ala Ala Ala Ala
1               5                   10                  15

<210> SEQ ID NO 3
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 3

Ala Lys Glu Tyr Ala Ala Ala Ala Ala Lys Ala Ala Ala Ala Ala
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Ala Lys Lys Tyr Ala Ala Ala Ala Ala Lys Ala Ala Ala Ala Ala
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Ala Glu Ala Tyr Ala Ala Ala Ala Ala Lys Ala Ala Ala Ala Ala
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Lys Glu Ala Tyr Ala Ala Ala Ala Ala Lys Ala Ala Ala Ala Ala
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ala Glu Glu Tyr Ala Ala Ala Ala Ala Lys Ala Ala Ala Ala Ala
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Ala Glu Tyr Ala Ala Ala Ala Ala Lys Ala Ala Ala Ala Ala
 1               5                  10                  15

<210> SEQ ID NO 9
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 9

Glu Lys Ala Tyr Ala Ala Ala Ala Ala Lys Ala Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Ala Ala Lys Tyr Glu Ala Ala Ala Ala Lys Ala Ala Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Ala Ala Lys Tyr Ala Glu Ala Ala Ala Lys Ala Ala Ala Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Glu Ala Ala Tyr Ala Ala Ala Ala Ala Lys Ala Ala Ala Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Glu Lys Lys Tyr Ala Ala Ala Ala Ala Lys Ala Ala Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Glu Ala Lys Tyr Ala Ala Ala Ala Ala Lys Ala Ala Ala Ala
1               5                   10                  15

<210> SEQ ID NO 15
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 15

Ala Glu Lys Tyr Ala Ala Ala Ala Ala Ala Ala Ala Ala Ala Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Ala Lys Glu Tyr Ala Ala Ala Ala Ala Ala Ala Ala Ala Ala Ala
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Ala Lys Lys Tyr Glu Ala Ala Ala Ala Ala Ala Ala Ala Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ala Lys Lys Tyr Ala Glu Ala Ala Ala Ala Ala Ala Ala Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Ala Glu Ala Tyr Lys Ala Ala Ala Ala Ala Ala Ala Ala Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Lys Glu Ala Tyr Ala Ala Ala Ala Ala Ala Ala Ala Ala Ala Ala
1               5                   10                  15

<210> SEQ ID NO 21
<211> LENGTH: 15
<212> TYPE: PRT
<213> ORGANISM: Artificial Sequence
<220> FEATURE:
```

<223> OTHER INFORMATION: Synthetic

<400> SEQUENCE: 21

Ala Glu Glu Tyr Lys Ala Ala Ala Ala Ala Ala Ala Ala Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Ala Ala Glu Tyr Lys Ala Ala Ala Ala Ala Ala Ala Ala Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Glu Lys Ala Tyr Ala Ala Ala Ala Ala Ala Ala Ala Ala Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ala Ala Lys Tyr Glu Ala Ala Ala Ala Ala Ala Ala Ala Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Ala Ala Lys Tyr Ala Glu Ala Ala Ala Ala Ala Ala Ala Ala Ala
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

Glu Lys Lys Tyr Ala Ala Ala Ala Ala Ala Ala Ala Ala Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic

```
<400> SEQUENCE: 27

Glu Ala Lys Tyr Ala Ala Ala Ala Ala Ala Ala Ala Ala Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Ala Glu Tyr Ala Lys Ala Ala Ala Ala Ala Ala Ala Ala Ala Ala
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Ala Glu Lys Ala Tyr Ala Ala Ala Ala Ala Ala Ala Ala Ala Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Glu Lys Tyr Ala Ala Ala Ala Ala Ala Ala Ala Ala Ala Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Ala Tyr Lys Ala Glu Ala Ala Ala Ala Ala Ala Ala Ala Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Ala Lys Tyr Ala Glu Ala Ala Ala Ala Ala Ala Ala Ala Ala Ala
1               5                   10                  15

<210> SEQ ID NO 33
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 33
agcatacagg tcctggcatc ttgt                                              24

<210> SEQ ID NO 34
<211> LENGTH: 24
<212> TYPE: DNA
<213> ORGANISM: Artificial Sequence
<220> FEATURE:
<223> OTHER INFORMATION: Synthetic

<400> SEQUENCE: 34
caaagaccac atgcttgcca tcca                                              24

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
agatcacatt cacggtgctg gcta                                              24

<210> SEQ ID NO 36
<211> LENGTH: 24
<212> TYPE: DNA
<213> ORGANISM: Artificial Sequence
<220> FEATURE:
<223> OTHER INFORMATION: Synthetic

<400> SEQUENCE: 36
agctttggga tggtagctgg aaga                                              24

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
tgtgaaggga ttaacgaggc tgga                                              24

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
ccatgtttcg ggcacatttc caca                                              24

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
aactgcatcc atatcgatga c                                                 21

<210> SEQ ID NO 40
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 40
gtggcaatga tctcaacac                                                      19

<210> SEQ ID NO 41
<211> LENGTH: 18
<212> TYPE: DNA
<213> ORGANISM: Artificial Sequence
<220> FEATURE:
<223> OTHER INFORMATION: Synthetic

<400> SEQUENCE: 41
catccacgtg ttggctca                                                       18

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
gatcatcttg ctggtgaatg agt                                                 23

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gcctcttctc attcctgctt                                                     20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ctcctccact tggtggtttg                                                     20

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
ccaaaagatg aagggctgct t                                                   21

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
```
tgctgctgcg agatttgaag                                          20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gaagttcaac atcaagagca                                          20

<210> SEQ ID NO 48
<211> LENGTH: 19
<212> TYPE: DNA
<213> ORGANISM: Artificial Sequence
<220> FEATURE:
<223> OTHER INFORMATION: Synthetic

<400> SEQUENCE: 48
catagtccct ttggtccag                                           19

<210> SEQ ID NO 49
<211> LENGTH: 24
<212> TYPE: DNA
<213> ORGANISM: Artificial Sequence
<220> FEATURE:
<223> OTHER INFORMATION: Synthetic

<400> SEQUENCE: 49
tgaattccct gggtgagaag ctga                                     24

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
tggccttgta gacaccttgg tctt                                     24

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
aattgctgcc ttcgccctct ttac                                     24

<210> SEQ ID NO 52
<211> LENGTH: 24
<212> TYPE: DNA
<213> ORGANISM: Artificial Sequence
<220> FEATURE:
<223> OTHER INFORMATION: Synthetic

<400> SEQUENCE: 52
tgtacaggct gaggactttg gtgt                                     24

<210> SEQ ID NO 53
<211> LENGTH: 19
<212> TYPE: DNA
<213> ORGANISM: Artificial Sequence

```
<220> FEATURE:
<223> OTHER INFORMATION: Synthetic

<400> SEQUENCE: 53
ccggaccaga gaccctttg                                                    19

<210> SEQ ID NO 54
<211> LENGTH: 23
<212> TYPE: DNA
<213> ORGANISM: Artificial Sequence
<220> FEATURE:
<223> OTHER INFORMATION: Synthetic

<400> SEQUENCE: 54
cctgtgggct tgttgaagta aaa                                               23

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
gatgctcagc agtcaagtgc cttt                                              24

<210> SEQ ID NO 56
<211> LENGTH: 24
<212> TYPE: DNA
<213> ORGANISM: Artificial Sequence
<220> FEATURE:
<223> OTHER INFORMATION: Synthetic

<400> SEQUENCE: 56
gacatgtttg cggcatccag gtaa                                              24
```